US011548946B2

(12) United States Patent
Markovic et al.

(10) Patent No.: US 11,548,946 B2
(45) Date of Patent: *Jan. 10, 2023

(54) CARRIER-PD-L1 BINDING AGENT COMPOSITIONS FOR TREATING CANCERS

(71) Applicant: Mayo Foundation for Medical Education and Research, Rochester, MN (US)

(72) Inventors: Svetomir N. Markovic, Rochester, MN (US); Wendy K. Nevala, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 438 days.

This patent is subject to a terminal disclaimer.

(21) Appl. No.: 16/330,030

(22) PCT Filed: Aug. 31, 2017

(86) PCT No.: PCT/US2017/049746
§ 371 (c)(1),
(2) Date: Mar. 1, 2019

(87) PCT Pub. No.: WO2018/045239
PCT Pub. Date: Mar. 8, 2018

(65) Prior Publication Data
US 2019/0202916 A1  Jul. 4, 2019

Related U.S. Application Data

(60) Provisional application No. 62/382,731, filed on Sep. 1, 2016.

(51) Int. Cl.
| | | |
|---|---|---|
| *C07K 16/28* | (2006.01) | |
| *A61K 9/51* | (2006.01) | |
| *A61K 31/337* | (2006.01) | |
| *A61K 45/06* | (2006.01) | |
| *A61K 39/395* | (2006.01) | |
| *A61P 35/00* | (2006.01) | |
| *A61K 9/19* | (2006.01) | |
| *A61K 39/00* | (2006.01) | |

(52) U.S. Cl.
CPC ............ *C07K 16/2818* (2013.01); *A61K 9/19* (2013.01); *A61K 9/51* (2013.01); *A61K 31/337* (2013.01); *A61K 39/39558* (2013.01); *A61K 45/06* (2013.01); *A61P 35/00* (2018.01); *C07K 16/2827* (2013.01); *A61K 2039/505* (2013.01)

(58) Field of Classification Search
CPC combination set(s) only.
See application file for complete search history.

(56) References Cited

U.S. PATENT DOCUMENTS

| | | |
|---|---|---|
| 4,350,687 A | 9/1982 | Lipton et al. |
| 5,026,772 A | 6/1991 | Kobayashi et al. |
| 5,116,944 A | 5/1992 | Sivam et al. |
| 5,216,130 A | 6/1993 | Line et al. |
| 5,252,713 A | 10/1993 | Morgan, Jr. et al. |
| 5,260,308 A | 11/1993 | Poduslo et al. |
| 5,728,541 A | 3/1998 | Kornblith |
| 5,736,137 A | 4/1998 | Anderson et al. |
| 6,054,297 A | 4/2000 | Carter et al. |
| 6,147,060 A | 11/2000 | Zasloff |
| 6,416,967 B2 | 7/2002 | Kornblith |
| 6,537,579 B1 | 3/2003 | Desai et al. |
| 6,933,129 B1 | 8/2005 | Kornblith |
| 7,041,301 B1 | 5/2006 | Markovic |
| 7,112,409 B2 | 9/2006 | Blumenthal |
| 7,731,950 B2 | 6/2010 | Noessner |
| 7,758,891 B2 | 7/2010 | Desai et al. |
| 7,820,788 B2 | 10/2010 | Desai et al. |
| 7,878,552 B2 | 2/2011 | Freter |
| 7,906,121 B2 | 3/2011 | Chang et al. |
| 7,923,536 B2 | 4/2011 | Desai et al. |
| 8,034,375 B2 | 10/2011 | Desai et al. |
| 8,119,129 B2 | 2/2012 | Jure-Kunkel et al. |

(Continued)

FOREIGN PATENT DOCUMENTS

| | | |
|---|---|---|
| CN | 105828837 A | 8/2016 |
| EP | 1913947 | 4/2008 |

(Continued)

OTHER PUBLICATIONS

International Search Report and Written Opinion corresponding to International Application No. PCT/US2017/049745 dated Dec. 15, 2017.
International Search Report and Written Opinion corresponding to International Application No. PCT/US2017/049746 dated Nov. 27, 2017.
Emens et al.: "(OT1-01-06) A phase III randomized trial of atezolizumab in combination with nab-paclitaxel as first line therapy for patients with metastatic triple-negative breast cancer (mTNBC)", 2015. XP002775313, 2015 San Antonio Breast Cancer Symposium, URL:http://sabcs.org/portals/sabcs2016/documents/sabcs-2015-abstracts.pdf?v=5.

(Continued)

*Primary Examiner* — Laura B Goddard
(74) *Attorney, Agent, or Firm* — Baker Botts L.L.P.

(57) ABSTRACT

Described herein are compositions of binding agents and carrier proteins, and optionally at least one therapeutic agent, and methods of making and using the same, in particular, as a cancer therapeutic. Also described are lyophilized compositions of binding agents and carrier proteins, and optionally at least one therapeutic agent, and methods of making and using the same, in particular, as a cancer therapeutic. Still also described are methods for treating and/or increasing the therapeutic effectiveness of an immunotherapy of a patient suffering from a cancer which expresses PD-L1 or PD-L2 by administering to the patient a nanoparticle composition and a PD-1 immunotherapy.

14 Claims, 13 Drawing Sheets

(56) References Cited

U.S. PATENT DOCUMENTS

| | | |
|---|---|---|
| 8,138,229 B2 | 3/2012 | Desai et al. |
| 8,268,348 B2 | 9/2012 | Desai et al. |
| 8,314,156 B2 | 11/2012 | Desai et al. |
| 8,344,177 B2 | 1/2013 | Neri et al. |
| 8,735,394 B2 | 5/2014 | Desai et al. |
| 8,853,260 B2 | 10/2014 | Desai et al. |
| 9,101,543 B2 | 8/2015 | Desai et al. |
| 9,387,244 B2 | 7/2016 | Markovic |
| 9,427,477 B2 | 8/2016 | Markovic et al. |
| 9,446,148 B2 | 9/2016 | Markovic et al. |
| 9,533,058 B2 | 1/2017 | Markovic et al. |
| 9,555,128 B2 | 1/2017 | Markovic et al. |
| 9,566,350 B2 | 2/2017 | Markovic et al. |
| 9,757,453 B2 | 9/2017 | Markovic et al. |
| 10,279,035 B2 | 5/2019 | Markovic et al. |
| 10,279,036 B2 | 5/2019 | Markovic et al. |
| 10,300,016 B2 | 5/2019 | Markovic et al. |
| 10,307,482 B2 | 6/2019 | Markovic et al. |
| 10,322,084 B2 | 6/2019 | Markovic et al. |
| 10,376,579 B2 | 8/2019 | Markovic et al. |
| 10,376,580 B2 | 8/2019 | Markovic et al. |
| 10,391,055 B2 | 8/2019 | Markovic et al. |
| 10,406,224 B2 | 9/2019 | Markovic et al. |
| 10,413,606 B2 | 9/2019 | Markovic et al. |
| 10,420,839 B2 | 9/2019 | Markovic et al. |
| 10,441,656 B2 | 10/2019 | Markovic et al. |
| 10,471,145 B2 | 11/2019 | Markovic et al. |
| 10,478,495 B2 | 11/2019 | Markovic et al. |
| 10,493,150 B2 | 12/2019 | Markovic et al. |
| 10,507,243 B2 | 12/2019 | Markovic et al. |
| 10,561,726 B2 | 2/2020 | Swiss et al. |
| 10,570,213 B2 * | 2/2020 | Kim .................. C07K 16/3015 |
| 10,596,111 B2 | 3/2020 | Markovic et al. |
| 10,596,112 B2 | 3/2020 | Markovic et al. |
| 10,610,484 B2 | 4/2020 | Markovic et al. |
| 10,618,969 B2 | 4/2020 | Markovic et al. |
| 10,624,846 B2 | 4/2020 | Markovic et al. |
| 10,668,151 B2 | 6/2020 | Markovic et al. |
| 10,765,741 B2 | 9/2020 | Markovic et al. |
| 10,772,833 B2 | 9/2020 | Markovic et al. |
| 10,780,049 B2 | 9/2020 | Markovic et al. |
| 10,780,050 B2 | 9/2020 | Markovic et al. |
| 2002/0111362 A1 | 8/2002 | Rubinfeld |
| 2004/0005318 A1 | 1/2004 | Davis et al. |
| 2004/0077601 A1 | 4/2004 | Adams et al. |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2007/0148135 A1 | 6/2007 | Dang et al. |
| 2007/0166388 A1 | 7/2007 | Desai et al. |
| 2009/0004118 A1 | 1/2009 | Nie et al. |
| 2010/0047234 A1 | 2/2010 | Markovic |
| 2010/0092489 A1 | 4/2010 | Van De Winkel et al. |
| 2010/0112077 A1 | 5/2010 | Desai et al. |
| 2010/0172835 A1 | 7/2010 | Ruoslahti et al. |
| 2010/0260679 A1 | 10/2010 | Shachar et al. |
| 2010/0311679 A1 | 12/2010 | Olson et al. |
| 2011/0014117 A1 | 1/2011 | Wang et al. |
| 2011/0076273 A1 | 3/2011 | Adler et al. |
| 2011/0097340 A1 | 4/2011 | Ramaghandra et al. |
| 2011/0104143 A1 | 5/2011 | Buchsbaum et al. |
| 2011/0150902 A1 | 6/2011 | Markovic |
| 2011/0262525 A1 | 10/2011 | Wang et al. |
| 2012/0263739 A1 | 10/2012 | Langer |
| 2012/0315273 A1 | 12/2012 | Markovic |
| 2013/0028895 A1 | 1/2013 | Wulf |
| 2013/0071403 A1 | 3/2013 | Rolland et al. |
| 2013/0149238 A1 | 6/2013 | Kavlie et al. |
| 2013/0164818 A9 | 6/2013 | Chang et al. |
| 2014/0056909 A1 | 2/2014 | Markovic |
| 2014/0155344 A1 | 6/2014 | Neil et al. |
| 2014/0161819 A1 | 6/2014 | Hann et al. |
| 2014/0178486 A1 * | 6/2014 | Markovic .......... A61K 39/3955 424/499 |
| 2014/0302017 A1 | 10/2014 | Markovic |
| 2014/0314774 A1 | 10/2014 | Zhou et al. |
| 2015/0050356 A1 | 2/2015 | Desai et al. |
| 2015/0246122 A1 | 9/2015 | Markovic et al. |
| 2016/0095942 A1 | 4/2016 | Markovic et al. |
| 2016/0184229 A1 | 6/2016 | Markovic et al. |
| 2016/0184452 A1 | 6/2016 | Markovic et al. |
| 2016/0184453 A1 | 6/2016 | Markovic et al. |
| 2016/0235860 A1 | 8/2016 | Markovic et al. |
| 2016/0250351 A1 | 9/2016 | Markovic et al. |
| 2016/0256431 A1 | 9/2016 | Markovic et al. |
| 2016/0263241 A1 | 9/2016 | Markovic et al. |
| 2016/0310610 A1 | 10/2016 | Markovic et al. |
| 2016/0324964 A1 | 11/2016 | Markovic et al. |
| 2016/0338961 A1 | 11/2016 | Markovic et al. |
| 2016/0339118 A1 | 11/2016 | Markovic et al. |
| 2017/0021023 A1 | 1/2017 | Dikstein |
| 2017/0021032 A1 | 1/2017 | Markovic et al. |
| 2017/0021034 A1 | 1/2017 | Markovic et al. |
| 2017/0071897 A1 | 3/2017 | Markovic et al. |
| 2017/0095574 A1 | 4/2017 | Swiss et al. |
| 2017/0100492 A1 | 4/2017 | Markovic et al. |
| 2017/0106087 A1 | 4/2017 | Markovic et al. |
| 2017/0128408 A1 | 5/2017 | Markovic et al. |
| 2017/0128583 A1 | 5/2017 | Markovic et al. |
| 2017/0128584 A1 | 5/2017 | Markovic et al. |
| 2017/0128585 A1 | 5/2017 | Markovio et al. |
| 2017/0128586 A1 | 5/2017 | Markovic et al. |
| 2017/0128587 A1 | 5/2017 | Markovic et al. |
| 2017/0128588 A1 | 5/2017 | Markovic et al. |
| 2017/0182174 A1 | 6/2017 | Markovic et al. |
| 2017/0182175 A1 | 6/2017 | Markovic et al. |
| 2017/0182180 A1 | 6/2017 | Markovic et al. |
| 2017/0182183 A1 | 6/2017 | Markovic et al. |
| 2017/0182184 A1 | 6/2017 | Markovic et al. |
| 2017/0182186 A1 | 6/2017 | Markovic et al. |
| 2017/0182187 A1 | 6/2017 | Markovic et al. |
| 2017/0196831 A1 | 7/2017 | Markovic et al. |
| 2017/0196832 A1 | 7/2017 | Markovic et al. |
| 2017/0196833 A1 | 7/2017 | Markovic et al. |
| 2017/0216453 A1 | 8/2017 | Markovic et al. |
| 2017/0232102 A1 | 8/2017 | Markovic et al. |
| 2017/0291952 A1 | 10/2017 | Markovic et al. |
| 2017/0326234 A1 * | 11/2017 | Renschler .............. A61K 45/06 |
| 2018/0235886 A1 | 8/2018 | Markovic et al. |
| 2019/0022188 A1 | 1/2019 | Markovic |
| 2019/0038761 A1 | 2/2019 | Markovic et al. |
| 2019/0099498 A1 | 4/2019 | Markovic et al. |
| 2019/0184032 A1 | 6/2019 | Markovic et al. |
| 2019/0201546 A1 | 7/2019 | Markovic et al. |
| 2019/0216944 A1 | 7/2019 | Markovic et al. |
| 2020/0237907 A1 | 7/2020 | Swiss et al. |
| 2020/0268884 A1 | 8/2020 | Markovic et al. |
| 2020/0308294 A1 | 10/2020 | Markovic et al. |

FOREIGN PATENT DOCUMENTS

| | | |
|---|---|---|
| EP | 3204413 | 8/2017 |
| EP | 3533870 | 9/2019 |
| JP | S60146833 | 8/1985 |
| JP | S6178731 | 4/1986 |
| JP | H04504253 | 7/1992 |
| JP | 2001072589 | 3/2001 |
| JP | 2012522809 | 9/2012 |
| JP | 2015-518826 A | 7/2015 |
| KR | 1020090078330 | 7/2009 |
| RU | 2011133819 | 2/2013 |
| RU | 2505315 C2 | 1/2014 |
| WO | 89/10398 | 11/1989 |
| WO | 97/49390 | 12/1997 |
| WO | 99/00113 | 1/1999 |
| WO | 99/51248 | 10/1999 |
| WO | 2004/022097 | 3/2004 |
| WO | 2004/096224 | 11/2004 |
| WO | 2006/034455 | 3/2006 |
| WO | 2006/089290 | 8/2006 |
| WO | 2007/027819 | 3/2007 |
| WO | 2007/027941 | 3/2007 |
| WO | 2008/047272 | 4/2008 |
| WO | 2008/057561 | 5/2008 |

(56) References Cited

FOREIGN PATENT DOCUMENTS

| | | |
|---|---|---|
| WO | 2008/057562 | 5/2008 |
| WO | 2008076373 A1 | 6/2008 |
| WO | 2008/112987 | 9/2008 |
| WO | 2009/043159 | 4/2009 |
| WO | 2009/055343 | 4/2009 |
| WO | 2010/003057 | 1/2010 |
| WO | 2010/017216 | 2/2010 |
| WO | 2010/118365 | 10/2010 |
| WO | 2010/124009 | 10/2010 |
| WO | 2010/136492 | 12/2010 |
| WO | 2012/048223 | 4/2012 |
| WO | 2012/088388 | 6/2012 |
| WO | 2012/154681 | 11/2012 |
| WO | 2012/154861 | 11/2012 |
| WO | 2013/173223 A1 | 11/2013 |
| WO | 2014/009774 | 1/2014 |
| WO | 2014/037422 | 3/2014 |
| WO | 2014/055415 | 4/2014 |
| WO | 2014/105644 | 7/2014 |
| WO | 2014/123612 | 8/2014 |
| WO | 2015/048520 | 4/2015 |
| WO | 2015095418 A1 | 6/2015 |
| WO | 2015/191969 | 12/2015 |
| WO | 2015/195476 | 12/2015 |
| WO | 2016/057554 | 4/2016 |
| WO | 2016/059220 | 4/2016 |
| WO | 2016/089873 | 6/2016 |
| WO | 2017/031368 | 2/2017 |
| WO | 2017/062063 | 4/2017 |
| WO | 2017/120581 | 7/2017 |
| WO | 2017/139698 | 8/2017 |
| WO | 2017/165439 | 9/2017 |
| WO | 2017/165440 | 9/2017 |
| WO | 2017/176265 | 10/2017 |
| WO | 2018/027205 | 2/2018 |
| WO | 2018/045238 | 3/2018 |
| WO | 2018/045239 | 3/2018 |
| WO | 2018/048815 | 3/2018 |
| WO | 2018/048816 | 3/2018 |
| WO | 2018/048958 | 3/2018 |

OTHER PUBLICATIONS

Adams et at, "(P2-11-01) Safety and clinical activity of atezolizumab (anti-PDL1) in combination with nab-paclitaxel in patients with metastatic tripie-negative breast cancer", 2015, XP002775314, 2015 San Antonio Breast Cancer Symposium, URL: http://sabcs.org/portals/sabcs2016/documents/sabcs-2015-abstracts.pdf?v=5.

Inman, "Atezolizumab/Nab-Paclitaxel Combo Shows High Response Rates In TNBC", OneLive, Dec. 10, 2015, 4 pages.

Adams et al., "Phase lb trial of atezolizumab in combination with nab-paclitaxel in patients with metastatic triple-negative breast cancer (mTNBC)" Journal of Clinical Oncology col. 34, No. 15, May 1, 2016, 4 pages.

Anonymous, "A Phase III, Multicenter, Randomized Placebo-Controlled Study of Atezolizumab (Anti-PD-L1 Antibody) in Combination with Nab Paclitaxel Compared with Placebo with Nab Paclitaxel for Patients with Previously Untreated Metastatic Triple Negative Breast Cancer", ClinicalTrials.gov, Apr. 21, 2015, 1 page.

Anonymous, "Atezolizumab Plus Abraxane Promising New Treatment for Triple-Negative Breast Cancer", UNM Comprehensive Cancer Center, Jan. 7, 2016, pages 1-2.

Fabi et al, "Prospective study on nanoparticle albumin-bound paclitaxel in advanced breast cancer: clinical results and biological observations in taxane-pretreated patients", Drug Design, Development and Therapy vol. 9, Nov. 1, 2015, 7 pages.

Hamilton et al, "Nab-Paclitaxel/Bevacizumab/Carboplatin Chemotherapy In First-Line Triple Negative Metastatic Breast Cancer" Clinical Breast Cancer, vol. 13, No. 6, Dec. 2013, 6 pages.

International Search Report and Written Opinion corresponding to International Application No. PCT/US2017/050134 dated Nov. 16, 2017.

International Search Report and Written Opinion corresponding to International Application No. PCT/US2017/050137 dated Nov. 27, 2017.

Mustacchi et al, "The role of taxanes in triple-negative breast cancer, literature review", Drug Design, Development and Therapy, vol. 9, Aug. 5, 2015, 16 pages.

Nahleh et al, "Swog 0800(NCI CDR0000636131): addition of bevacizumba to neoadjuvant nab-paclitaxel with dose-dense doxorubicin and cyclophosphamide improves pathologic complete response (pCR) rates In inflammatory or locally advanced breastcancer". Breast Cancer Research and Treatment, vol. 158, No. 3 Jul. 8, 2016, 12 pages.

Volk-Draper et al, "Novel Model for Basaloid Triple-negative Breast Cancer: Behavior In Vivo and Response to Therapy", vol. 14, No. 10, Oct. 1, 2012, 18 pages.

Anonymous "Paclitaxel Albumin-Stabilized Nanoparticle Formulation and Bevacizumab in Treating Patients With Stage IV Melanoma That Cannot Be Removed by Surgery or Gynecological Cancers", NCT02020707, ClinicalTrials.gov, Dec. 25, 2013 (13 pages).

U.S. Appl. No. 15/187,672, office action dated Sep. 11, 2019.
U.S. Appl. No. 15/225,428, office action dated Jul. 31, 2019.
U.S. Appl. No. 15/225,428, office action dated Dec. 6, 2019.
U.S. Appl. No. 15/225,542, office action dated Jan. 14, 2020.
U.S. Appl. No. 15/286,024, office action dated Aug. 1, 2019.
U.S. Appl. No. 15/359,569, office action dated Jul. 26, 2019.
U.S. Appl. No. 15/359,569; office action dated Jan. 17, 2020.
U.S. Appl. No. 15/430,411; office action dated Oct. 31, 2019.
U.S. Appl. No. 15/456,395; office action dated Aug. 14, 2019.
U.S. Appl. No. 15/456,399; office action dated Aug. 14, 2019.
U.S. Appl. No. 15/460,552; office action dated Aug. 14, 2019.
U.S. Appl. No. 15/460,699; office action dated Aug. 28, 2019.
U.S. Appl. No. 15/461,288; office action dated Aug. 28, 2019.
U.S. Appl. No. 15/675,596; office action dated Dec. 3, 2019.
U.S. Appl. No. 15/752,155; office action dated Sep. 25, 2019.

Cirstoiu-Hapca et al. "Benefit of anti-HER2-coated paciitaxel-loaded immuno-nanpoarticles in the treatment of disseminated ovarian cancer: Therapeutic efficacy and biodistribution in mice", Journal of Controlled Release 144:324-331 (2010).

European Application No. 17771005.0, Extended European Search Report dated Oct. 17, 2019.

European Application No. 17771006.8, Extended European Search Report dated Oct. 10, 2019.

International Preliminary Report on Patentability for Application No. PCT/US2017/050134 dated Mar. 21, 2019.

Liu et al. "Freeze-Drying of Proteins". In: Walkers W., Oldenhof H. (eds) Cryopreservation and Freeze-Drying Protocols. Methods in Molecular Biology (Methods and Protocols), vol. 1257. Springer, New York, NY; published online Nov. 14, 2014.

Reynolds et al. "Phase II Trial of Nanoparticle Albumin-Bound Paclitaxel, Carboplatin, and Bevacizumab in First-Line Patients with Advanced Nonsquamous Non-small Cell Lung Cancer", J Thoracic Oncology 4(12):1537-1543 (2009).

"Concurrent Infusions", J Oncol Pract, 4(4): 171, Jul. 2008.

Abraxanet® for Injectable Suspension (paclitaxel protein-bound particles for injectable suspension) (albumin-bound) [drug label], 22 pages, Sep. 2009.

Abraxis Bioscience, Inc,. "Abraxane: For the adjuvant treatment of node-positive breast cancer administered sequentially to standard doxorubicin-containing combination chemotherapy" Oncologic Drugs Advisory Committee Meeting (available to public Aug. 4. 2006).

Agarwal et al., "Flow Cytornefric analysis of Th1 and Th2 cytokines in PBMCs as a parameter of immunoioigical dysfunction in patients of Superficial Transitional cell carcinoma of bladder", Cancer Immunol. Immunother., 2006, 55(6):734-743.

Agarwala et al., "Randomized phase III study of paclitaxel plus carboplatin with or without sorafenib as second-line treatment in patients with advanced melanoma", J. Clin. Oncol., 2007, 25(18S):8510 (Abstract).

Allen "Ligand-targeted terapeutics in anticancer therapy, Cancer", Oct. 2002, 2(10), pp. 750-763.

Alley et al., "Contribution of Linker Stability to the Advities of Anticancer Immunoconjugates", Bioconjugate Chem., 2008, 19(3), pp. 759-765.

(56) References Cited

OTHER PUBLICATIONS

Anonymous, "A Phase II, multicenter, randomized, double-blind placebo-controlled trial evaluating the efficacy and safety of bevacizumab in combination with carboplatin and paclitaxel chemotherapy for the first-line treatment of patients with metastatic melanoma", U.S. National Institutes of Health, 2007, 3 pages.
Anonymous, "Phase II trial of carboplatin, weekly paclitaxel and biweekly bevacizemab in patients with unresectable stage IV melanoma", U.S. National Institutes of Health, 2007, 4 pages.
Anonymous, "A Study of Bevacizurriab With Carboplatin and Paciltaxel Chemotherapy for the First-Line Treatment of Patients With Metastatic Melanoma (Beam)," ClinicalTrials.gov [online]. Retrieved from the Internet: URL: https://clinicaltrials.gov/archive/NCT00424252/200703 12, dated Mar. 12, 2007, 3 pages.
U.S. Appl. No. 14/116,619 office action dated Feb. 4, 2015.
U.S. Appl. No. 14/116,619, office action dated Apr. 28, 2016.
U.S. Appl. No. 14/116,619, office action dated Sep. 10, 2015.
U.S. Appl. No. 14/432,979, office action dated Jan. 7, 2019.
U.S. Appl. No. 14/432,979, office action dated May 16, 2018.
U.S. Appl. No. 14/432,979, office action dated Jun. 30, 2016.
U.S. Appl. No. 14/432,979, office action dated Oct. 4, 2017.
U.S. Appl. No. 14/432,979, office action dated Dec. 15, 2016.
U.S. Appl. No. 14/882,327, office action dated May 2, 2016.
U.S. Appl. No. 15/030,567, office action dated Sep. 7, 2016.
U.S. Appl. No. 15/030,568, office action dated May 25, 2017.
U.S. Appl. No. 15/030,568, office action dated Jun. 18, 2018.
U.S. Appl. No. 15/030,568, office action dated Dec. 1, 2017.
U.S. Appl. No. 15/052,336, office dated Jan. 22, 2019.
U.S. Appl. No. 15/052,336, office action dated Feb. 9, 2018.
U.S. Appl. No. 15/052,336, office action dated Sep. 4, 2018.
U.S. Appl. No. 15/052,623, office action dated Jan. 7, 2019.
U.S. Appl. No. 15/052,623, office action dated Feb. 9, 2018.
U.S. Appl. No. 15/052,623, office action dated May 19, 2017.
U.S. Appl. No. 15/052,623, office action dated Jul. 9, 2018.
U.S. Appl. No. 15/052,623, office action dated Nov. 25, 2016.
U.S. Appl. No. 15/060,967, office action dated Aug. 2, 2016.
U.S. Appl. No. 15/064,396, office action dated Aug. 9, 2016.
U.S. Appl. No. 15/092,403, office action dated Apr. 2, 2018.
U.S. Appl. No. 15/092,403, office action dated Oct. 4, 2018.
U.S. Appl. No. 15/092,433, office action dated Mar. 21, 2018.
U.S. Appl. No. 15/092,433, office action dated Aug. 10, 2018.
U.S. Appl. No. 15/092,433, office action dated Oct. 11, 2017.
U.S. Appl. No. 15/092,433, office action dated Dec. 12, 2018.
U.S. Appl. No. 15/187,672, office action dated May 31, 2018.
U.S. Appl. No. 15/187,672, office action dated Nov. 28, 2018.
U.S. Appl. No. 15/202,115, office action dated Jan. 20, 2017.
U.S. Appl. No. 15/202,115, office action dated Sep. 26, 2016.
U.S. Appl. No. 15/225,428, office action dated Aug. 14, 2018.
U.S. Appl. No. 15/225,428, office action dated Dec. 20, 2017.
U.S. Appl. No. 15/225,504, office action dated Apr. 4, 2017.
U.S. Appl. No. 15/225,504, office action dated Aug. 1, 2018.
U.S. Appl. No. 15/225,504, office action dated Nov. 9, 2016.
U.S. Appl. No. 15/225,542, office action dated Apr. 4, 2017.
U.S. Appl. No. 15/225,542, office action dated Nov. 22, 2016.
U.S. Appl. No. 15/286,006, office action dated Jan. 9, 2017.
U.S. Appl. No. 15/286,006, office action dated Jan. 18, 2018.
U.S. Appl. No. 15/286,006, office action dated May 16, 2017.
U.S. Appl. No. 15/286,024, office action dated Jan. 6, 2017.
U.S. Appl. No. 15/286,024, office action dated May 19, 2017.
U.S. Appl. No. 15/331,754; office action dated Feb. 22, 2019.
U.S. Appl. No. 15/331,754; office action dated Oct. 11, 2018.
U.S. Appl. No. 15/359,569, office action dated Feb. 22, 2017.
U.S. Appl. No. 15/359,569, office action dated Jun. 23, 2017.
U.S. Appl. No. 15/359,569, office action dated Jul. 12, 2016.
U.S. Appl. No. 15/412,536; office action dated Oct. 1, 2018.
U.S. Appl. No. 15/412,554, office action dated Sep. 27, 2018.
U.S. Appl. No. 15/412,554, office action dated Jul. 10, 2018.
U.S. Appl. No. 15/412,581; office action dated Nov. 13, 2018.
U.S. Appl. No. 15/412,596, office action dated Sep. 4, 2018.
U.S. Appl. No. 15/412,596, office action dated Dec. 27, 2018.
U.S. Appl. No. 15/412,610, office action dated Jul. 9, 2018.
U.S. Appl. No. 15/413,257; office action dated Sep. 25, 2018.
U.S. Appl. No. 15/414,526; office action dated Nov. 16, 2018.
U.S. Appl. No. 15/414,533; office action dated Nov. 19, 2018.
U.S. Appl. No. 15/414,536; office action dated Oct. 11, 2018.
U.S. Appl. No. 15/452,669, office action dated May 5, 2017.
U.S. Appl. No. 15/452,669, office action dated Nov. 16, 2017.
U.S. Appl. No. 15/452,669, office action dated Nov. 26, 2018.
Arakawa et al., "Protein-Solvent Interactions in Pharmaceutical Formulations", Pharm. Res., Mar. 1991, vol. 8, Issue 3, pp. 285-291.
Armitage et al., "New approach to classifying non-Hodgkin's lymphomas: clinical features of the major histologic subtypes. Non-Hodgkin's Lymphoma Classification Project" J Clin Oncol 16, 2780-2795 (1998).
Asadullah et al., "Interleukin-10 therapy—a review of a new approach", Pharmacol Rev., 2003, 55(2):241-269.
Atkins et al., "High-dose recombinant interleukin-2 therapy in patients with metastatic melanoma: long-term survival update", Cancer J Sci Am., 2000, Suppl 6:SII-14.
Atkins, "Interleukin-2: clinical applications", Semin Oncol., 2002, 29(3 Suppl 7):12-27.
Avastin® Bevacizumab, Roche, [drug label], 24 pages, Sep. 2008.
Baba, Oleo Science 10(1):15-18 (Jan. 2010).
Bairagi et al., Albumin: A versatile Drug Carrier, Austin Therapeutics, (Nov. 17, 2015) vol. 2, No. 2, p. 1021 (pp. 1-6).
Balch et al., "The new melanoma staging system", Semin Cutan Med Surg., 2003, 22(1):42-54.
Balch et al., "Update on the melanoma staging system: The importance of sentinel node staging and primary tumor mitotic rate", Journal of Surgical Oncology, Aug. 19, 2011, vol. 104, Issue 4, pp. 379-385.
Bauer et al., "Rituximab, ofatumumab, and other monoclonal anti-CD20 antibodies for chronic lymphocytic leukaemia (Review)," Cochrane Database of Systematic Reviews, Issue 11, 125 pages (copyright 2012).
Baumgartner et al., "Melanoma induces immunosuppression by up-regulating FOXP3(+) regulatory T cells", J Surg Res., 2007, 141(1): 72-77.
Belani et al., "Multicenter randomized trial for stage IIIB or IV non-small-cell lung cancer using weekly paclitaxel and carboplatin followed by maintenance weekly paclitaxel or observation", J. Clin. Oncol., 2003, 21:2933-2939.
Bird et al., "Single-chain antigen-binding proteins", Science, Oct. 1988, 242(4877), pp. 423-426.
Boasberg at al., "Nab-paclitaxel and bavacizurnab as first-line therapy in patients with unresectable stage III and IV melanoma", J Clinical Oncology, 2009, 27, No. 15S, abstract#9071.
Boasberg et al., "Phase II trial of nab-paclitaxel and bevacizumab as first-line therapy in patients with unresectable melanoma", Journal of Clinical Oncology, May 20, 2011, vol. 29, No. 15 Supp. 8543.
Bolstad et al., "A comparison of normalization methods for high density oligonucleotide array data based on variance and bias", Bioinformatics, 2003, 19:185-193.
Cao et al., "Response of resistant melanoma to combination of weekly paclitaxel and bevacizumab", Clin Transl Oncol, 2007, 9:119-120.
Carson at al., "A phase 2 trial of recombinant humanized monoclonal anti-vascular endothelial growth factor (VEGF) antibody in patients with malignant melanoma", Proceedings of the ASCO vol. 22, No. 2873, General Poster Session, Thirty-Ninth Annual Meeting of the American Society of Clinical Oncology, May 31-Jun. 3, 2003, Chicago, IL, 2 pages.
Celis, "Overlapping human leukocyte antigen class I/II binding peptide vaccine for tile treatment of patients with stage IV melanoma: evidence of systemic immune dysfunction", Cancer, 2007, 110(1):203-214.
Chapman et al., "Improved Survival with Vemurafenib in Melanoma with BRAF V6006 Mutation", The New England Journal of Medicine, Jun. 30, 2011, vol. 364, Issue 26, pp. 2507-2516.
Chisholm et al., "Response to influenza immunizat on during treatment for cancer", Arch Dis Child, 2001, 84 (5):496-500.
Chong at al., "Combining cancer vaccines with chemotherapy", Expert Opin Pharmacother., 2006, 6(16):2813-2820.

(56) References Cited

OTHER PUBLICATIONS

Cleland et al., "The Development of Stable Protein Formulations. A close look at protein aggregation deamidation, and oxidation", Therapeutic Drug Carrier Systems, 1990, 10(4), pp. 307-377.

Colman, "Effects of amino acid sequence changes on antibody-antigen interactions," Reserach in Immunology (145(1):33-36, (1994).

Davis, "Affinity separation of antibody-toxin conjugate ffrom albumim-stabilized mutation" Am Biotechnol Lab., 12 (4):60-64, Mar. 1994.

Degrasse,"A Single-Stranded DNA Aptamer That Selectively Binds to *Staphylococcus aureus* Enterotox B", PLos One, 2012, 7(3) E33410, pp. 1-7.

Deguchi et al., "Effect of Methotrexate-Monoclonal Anti-Prostatic Acid Phosphates Antibody Conjugate on Human Prostate Tumor", Cancer Research, Aug. 1986, 46, pp. 3751-3755.

Demirkesen et al., "The correlation of angiogenesis with metastasis in primary cutaneous melanoma: a comparative analysis of microvessel denslty, expression of vascular endothelial growth factor and basic fibroblastic growth factor", Pathology, 2006, 38:132-137.

Denardo et al., "Inflammation and breast cancer. Balancing immune response: crosstalk between adaptive and innate immune cells dui ng breast cancer progression", Breast Cancer Res., 2007, 9(4):212.

Desai et al., "Enhanced antitumor activity and safety of albumin-bound nab-docetaxel versus polysotbate 80-based docetaxel", Eur. J. Cancer, Suppl.; 18th Symposium on molecular targets and cancer therapeutics; Prague, Czech Republic; Nov. 7-10, 2006, vol. 4, No. 12, Nov. 2006 *Nov. 2006), p. 49.

Desai et al., "Increased antitumor activity, intratumor paclitaxel concentrations, end endothelial cell transport of cremophor-free, albumin-bound paclitaxei, ABI-007, compared with cremopher-based paclitaxel", Clin Cancer Res., 2006, 12(4): 1317-24.

Deweers et al., "Daratumumab, a novel therapeutic human CD38 monoclonal antibody, induces killing of multiple myeloma and other hematological tumors", J. Immunol., 186(3): 1840-1848, Feb. 1, 2011.

Dudek et al., "Autologous large multivalent immunogen vaccine in patients with metastatic melanoma and renal cell carcinoma", Am. J. Clin. Oncol., Apr. 1, 2008, 31(2):173-181.

Edison, "MorphoSys," 16 pages (Aug. 8, 2013).

Elbayoumi et al., "Tumor-Targeted Nanomedicines: Enhanced Antitumor Efficacy In vivo of Doxorubicin-Loaded Long-Circulating Liposomes Modified with Cancer-Specific Monoclonal Antibody", Clin Cancer Res., 2009, 15 (6):1973-1980.

Ellyard et al., "Th2-mediated anti-tumor Immunity: friend or foe?", Tissue Antigens, 2007, 70(1):1-11.

Elsadek et al., "Impact of albumin on drug delivery—New applications on the horizon", J of Controlled Release, 2011, 1-25.

Elst et al. "Epidermal Growth Factor Receptor Expression a Activity in Route Myeloid Leukemia", Blood 116:3144 (2010), abstract.

European Application No. 08743903.0, Extended European Serach Report dated Jan. 24, 2011.

European Application No. 09774506.1, Extended European Search Report dated Mar. 22, 2012.

European Application No. 12781802.9, Extended European Search Report dated Dec. 18, 2014.

European Application No. 13843209.1 Extended European Search Report dated Sep. 5, 2016.

European Application No. 15806443.6, Extended European Search Report dated Dec. 11, 2017.

European Application No. 15809075.3, Extended European Search Report dated Dec. 21, 2017.

Ferrara et al., "The biology of VEGF and its receptors", Nat. Med., 2003, 9:669-676.

Flaherty et al., "Final Results of E2603: a double-blind, randomized phase III trial comparing carboplatin (CV) paclitaxel(P) with or without sorafenib(S) in metastic melanoma", J. Clin Oncol., 2010, 28: 15s (suppl: abstr 8511).

Flores et al., "Novel oral taxane therapies: recent Phase I results", Clin. Invest. vol. 3, No. 4, Apr. 1, 2013 (Apr. 1, 2013), pp. 333-341, XP055426571, UK, ISSN: 2041-6792, DOI: 10.4155/cli.13.18.

Folkman, "Angiogenesis in cancer, vascular, rheumatoid and other disease", Nat. Med., 1995,1, 27-31.

Fricke et al., "Vascular endothelial growth factor-trap ovecomes defects in dendritic cell differentiation but does not improve antigen-specific immune responses", Clin. Cancer Res., 2007, 13:4840-4848.

Gabrilovioh et al., "Production of vascular endothelial growth factor by human tumors inhibits the functional maturation of dendritic cells", Nat. Med., 1996, 2: 1096-1103.

Gao et al. "In vivo cancer targeting and imaging with semiconductor quantum dots", Nat Biotech, 2004, 22 (8):969-976.

Gogas et al., "Chemotherapy for metastatic melanoma: time for a change?", Cancer, 2007, 109(3): 455-464.

Golay et al., "Mechanism of action of therapeutic monoclonal antibodies: promises and pitfalls of in vitro and in vivo assay," Arch. Biochem. Biophys. 526(2):146-153 (2012).

Graells et al., Overproduction of VEGF165 concomitantly expressed with its receptors promotes growth and survival of melanoma cells through MAPK and P13K signaling, J. Invest. Dermatol., 2004, 123:1181-1161.

Gupta et al., "Ofatumumab, the first human anti-CD20 monoclonal antibody for the treatment of 13 cell hematologic malignancies," Ann. N.Y. Acad. Sci., 1253, pp. 43-56 (Jul. 25, 2012).

Haley et al., "Nanoparticles for drug delivery in cancer treatment", Urol. Oncol.: Seminars and Original Invest., 2008, 26:57-64.

Hara, "What is anti-ER2 antibody tubulin polymerization inhibiter complex T-DM1?," Pharm. Monthly 58(5):734-739 (May 2014).

Harlow et al., Antibodies: A Laboratory Manual. Cold Spring Harbor Laboratory, New York, NY 1988 (9 pages).

Hassan et al: "Comparison of Different Crosslinking Methods for Preparation of Docetaxel-loaded Albumin Nanoparticles", Iranian Journal of Pharmaceutical Research, vol. 14, No. 2, Apr. 2015 (Apr. 2015), pp. 385-394.

Hauschild et al., "Individualized therapy of disseminated cancer using malignant melanoma as a model", Cancer and Metastasis Reviews, 2006, 25(2): 253-256.

Hauschild at al., "Results of a Phase III, Randomized, Placebo-Controlled Study of Sorafenib in Combination with Carboplatin and Paclitaxel as Second-Line Treatment in Patients with Unresectable Stage III or IV Melanoma", Journal of Clinical Oncology, Jun. 10, 2009, vol. 27, No. 17, pp. 2823-2830.

Hegde et al. "Predictive Impact of Circulating Vascular Endothelial Growth Factor in Four Phase III Trials Evaluating Bevacizurnab," Clinical Cancer Research, Feb. 15, 2013 (Feb. 15, 2013) vol. 19, pp. 929-937.

Hersh et al., "A Phase 2 Clinical Thal of nab-Paclitaxel in Previously Treated and Chemotherapy-Naive Patients With Metastatic Melanoma", Cancer, Jan. 1, 2010, 118:155, pp. 155-163.

Hersh et al. "A randomized, controlled phase III trial of nab-Paclitaxel caress dacarbazine in chemotherapy-naive patients with metastatic melanoma", Ann Oncol. 2015, epub Sep. 26, 2015.

Hersh et al., "Open-label, multicenter, phase II trial of ABI-007 in previously treated and previously untreated patients with metastatic malignant melanoma", J. Clin. Oncol., 2005, 23(16S):7568 (Abstract).

Hobbs et al., "Regulation of Transport pathways in tumor vessels: role of tumor type and microenvironment", Proc Nati Aced Sci USA, Apr. 1996, 95, pp. 4607-4812.

Hodi et al., "Improved survival with ipilimumab in patients with metastatic melanoma", The New England Journal of Medicine, Aug. 19, 2010, vol. 363, No. 8, pp. 711-723.

Hodi et al., "Phase II study of paclitaxel and carboplatin for malignant melanoma", Am J. Clin. Oncol., 2002, 25:283-286.

Hood et al., Immunology, 1984, Benjamin, N.Y., 2nd edition.

Huncharek et al., "Single-agent DTIC versus combination chemotherapy with or without immunotherapy in metastatic melanoma: a meta-analysis of 3273 patents from 20 randomized trials", Melanoma Research, 11:75-81 (2001).

Hunkapiller et al., "Immunology: The growing immunoglobulin gene superfamily", Nature, Sep. 1986, 323, pp. 15-16.

Huston et al., "Protein engineering of antibody binding siren: Recovery of specific activity in an anti-digoxin sirgle-chain Fv analogue produced in *Escherichia coli*", Proc. Nat. Acad. Sci. USA, Aug. 1985, vol. 85, pp. 5879-5883.

(56) References Cited

OTHER PUBLICATIONS

Ibrahim et al., "Phase I and Pharmacokinetic Study of ABI-007, a Cremophor-free, Protein-stabilized, Nanoparticla Formulation of Paclitaxel", Clinical Cancer Research, May 2002, vol. 8, pp. 1038-1044.
Inagaki et al., "Clinical sgraficance of serum Thl-, Th2- and regulatory T cells-associated cytoknes in adult T-cell leukemia/lymphoma: High interleukin-5 and -10 levels are significant unfavorable prognostic factors". Int. J. Cancer, 2006, 118(12):3054-3061.
International Preliminary Report on Patentability for Application No. PCT/US2008/057025, dated Sep. 15, 2009.
International Preliminary Report on Patentability for Applicaton No. PCT/US2009/049511, dated Jan. 5, 2011.
International Preliminary Report on Patentability for Application No. PCT/US2012/037137, dated Nov. 12, 2013.
International Preliminary Report on Patentability for Application No. PCT/US2013/062638, dated Apr. 16, 2015.
International Preliminary Report on Patentability for Application No. PCT/US2015/035505, dated Dec. 22, 2016.
International Preliminary Report on Patentability for Application No. PCT/US2015/035515, dated Dec. 29, 2016.
International Preliminary Report on Patentability for Application No. PCT/US2015/054295 dated Oct. 13, 2016.
International Preliminary Report on Patentability for Application No. PCT/US2016/026270, dated Oct. 18, 2018.
International Preliminary Report on Patentability for Application No. PCT/US2017/012580, dated Jul. 19, 2018.
International Preliminary Report on Patentability for Application No. PCT/US2017/023442, dated Oct. 4, 2018.
International Preliminary Report on Patentability for Applicatlon No. PCT/US2017/023443, dated Oct. 4, 2018.
International Preliminary Report on Patentability for Application No. PCT/US2016/026267, dated Apr. 10, 2018.
International Search Report on Patentability for Application No. PCT/US2017/017653, dated Aug. 23, 2018.
International Search Report and Written Opinion for Application No. PCT/US2008/057025, dated Jul. 1, 2008.
International Search Report and Written Opinion for Application No. PCT/US2009/049511, dated Feb. 2, 2010.
International Search Report and Written Opinion for Application No. PCT/US2012/037137, dated Sep. 28, 2012.
International Search Report and Written Opinion for Application No. PCT/US2013/062638, dated Jan. 23, 2014.
International Search Report and Written Opinion for Application No. PCT/US2015/035505, dated Nov. 24, 2015.
International Search Report and Written Opinion for Application No. PCT/US2015/035515, dated Sep. 21, 2015.
International Search Report and Written Opinion for Application No. PCT/US2015/054295, dated Jan. 25, 2016.
International Search Report and Written Opinion for Application No. PCT/US2016/026267, dated Jul. 12, 2016.
International Search Report and Written Opinion for Application No. PCT/US2016/026270, dated Oct. 12, 2017.
International Search Report and Written Opinion for Application No. PCT/US2016/047641, dated Oct. 31, 2016.
International Search Report and Written Opinion for Application No. PCT/US2017/012580, dated Mar. 17, 2017.
International Search Report and Written Opinion for Applicaton No. PCT/US2017/017553, dated Feb. 10, 2017.
International Search Report and Written Opinion for Application No. PCT/US2017/045643, date Oct. 25, 2017.
International Search Report and Written Opinion for Application No. PCT/US2017/050355, dated Jan. 30, 2018.
Jaime et al., "Paclitaxel antibody cojugates and trehalose for preserving the immunological activity after freeze- drying," Curr Med Chem, 2004, 11(4):439-46 Abstract Only.
Jain et al., "Delivering nanomedicine to solid tumors", Nature Reviews Clinical Oncology, Nov. 7, 2010, pp. 653-664.
Jan et al., "Normalizing tumor vasculature with anti-angiogenic therapy: a new paradigm for combination therapy," Nat. Med. 7(9):987-989 (2001).
Jain, "Normalization of tumor vasculature: an emerging concept in antiangiogenic therapy," Science 307(5706):58-62 (2005).
Jazirehi et al., "Rituximab (anti-CD20) selectively modifies Bcl-xl and apoptosis protease activating factor-1 (Apaf-1) expression and sensitizes human non-Hodgkin's lymphoma a cell lines to paclitaxel-induced apoptosis," Mol. Cancer Ther. 2(11):118-93 (2003).
Jiang et al., "Regulation of Immune Responses by T Cells", N Engl J Med., 2006, 354(11): 1166-1176.
Jin et al., "Paclitaxel-loaded nanopartioles decorated with anti-CD133 antibody: a targeted therapy for liver cancer stem cells," J. Nanopart. Rest. 2014, 16:2157 (2014).
Jin et al: "Docetaxel-loaded PEG-albumin nanoparticles with improved antitumor efficiency against non-small cell lung cancer", Oncology Reports, vol. 36, No. 2, Aug. 8, 2016 (Aug. 8, 2016), pp. 871-878, XP055425487, ISSN: 1021-335X, DOI: 10.3892/or.2016.4863.
Julien et al., "Utilization of monoclonal antibody-targeted nanomaterials in the treatment of cancer", 2011, MAbs, 3:467-478.
Kamat et al., "Metronomic chemotherapy enhances the efficacy of antivascular therapy in ovarian cancer", Cancer Res., 2007, 67(1):281-288.
Kawai et al., "VEGF121 promotes lymphangiogenesis in the sentinel lymph nodes of non-sm cell lung carcinoma patients", Lung Cancer, 2008, 59(1):41-47.
Kelly et al. "Shape-Specific, Monodisperse Nano-Molding of Protein Particles," J. Am. Chem. Soc. 130:5438-5439 (2008).
Kikuchi et al., "Vascular endothelial growth factor and dendritic cells in human squamous cell carcinoma of the oral cavity", Anticancer Res., 2006, 26(3A):1833-1848.
Kim et al., "A dual target-directed agent against interleukin-6 receptor and tumor necrosis factor a ameliorates experimental arthritis", Scientitc Rep. 6:20150 (2016).
Kim et al., "BEAM: A Randomized Phase II Study Evaluating the Activity of Bevacizumab in Combination with Carboplatin Plus Paclitaxel in Patients With Previously Untreated Advanced Melanoma", Journal of Clinical Oncology, official journal of the American Society of Clinical Oncology, Jan. 1, 2012, vol. 30, No. 1, pp. 34-41.
Kirkwood et al., "A pooled analysis of eastern cooperative oncology gorup and intergroup trials of adjuvant high-dose interferon for melanoma", Clin Cancer Res., 2004, 10(5):1670-1677.
Kondejewski et al., "Synthesis and characterization of carbohydrate-linked murine monoclonal antibody K20-human serum albumin conjugates", Bioconjug Chem., 5(6):602-611, Nov.-Dec. 1994.
Korman et al., "Tumor immunotherapy: preclinical and clinical activity of anti-CTLA4 antibodies"; Curr Opin Invest Drugs, 2005, 6(6):582-591.
Kottschade et al., "A Phase II Trial of Nab-Paclitaxel (ABI-007) and Carboplatin in Patients with Unresectable Stage IV Melanoma"Cancer, Apr. 15, 2011, 117(8), pp. 1704-1710.
Kottschade et al., "A Randomized Phase 2 Study of Temozolomide and Bevacizumab or nab-Paclitaxel, Carboplatin, and Bevacizumab in Patients with Unresectable Stage IV Melanoma",Cancer, 2013, vol. 119, Issue 3, pp. 586-592.
Kratz et al., "Serum proteins as drug carriers of anticancer angents: a review", Drug Deliv., 5(4):281-299, 1998.
Kratz, "Albumin as a drug carrier: design of prodrugs, drug conjugates and nanopartictes", J Control Release, 132 (3):171-183, Epub May 17, 2008.
Krishnan et al., "Programmed death-1 receptor and interlenkin-10 in liver transplant recipient at high risk for late cytomegalovirus disease", Transpl Infect Dis., 12(4):353-70, print Aug. 2010, ePub Jan. 2010.
Kukowska-Latallo et al, "Nanoparticle Targeting of Anticancer Drug Improves Therapeutic Response in Animal Model of Human Epithelial Cancer", Cancer Res, 2005, 65(12):5317-5324.
Kumar et al., Thl/Th2 cytokine imbalance in meningloma, anaplastic astrocytoma and glioblastoma multiforme patients, Oncol. Ren., 2006, 15(6):1513-1516.
Lanzavecchia et al., "The use of hybrid hybridomas to target human cytotox T lymphocytes", Eur. J. Immunol., 1987, 17, pp. 105-111.

(56) References Cited

OTHER PUBLICATIONS

Lau et al., "Is inhibition of cancer angiogenesis and growth by paciltaxel schedule dependent?", Anti- Cancer Drugs, 2004,1 5:871-875.
Lee et al., "The co-delivery of pactitaxel and Herceptin using cationic micellar nanoparticles", Biomaterials vol. 30, No. 5, Feb. 1. 2009, pp. 919-927.
Lei et al., "Companng cellular uptake and cytotoxicity of targeted drug carriers in cancer cell lines with ifferent drug resistance mechanisms", Nanomed: Nanotech, Biol, and Med., 2011, 7:324-332.
Lev et al., "Dacarbazine causes transcriptional up-regulation of interleukin 8 and vascular endothelial growth factor in melanoma cells: a possible escape mechanism from chemotherapy", Mot. Cancer Thor., 2003, 2:753-763.
Lev et al., "Exposure of melanoma cells to dacarbazine results in enhanced tumor growth and metastasis in vivo", J. Clin. Oncol., 2004, 22:2092-2100.
Liang et al., "IFN-alpha regulates NK cell cytotoxicity through STAT1 pathway," Cytokine, Aug. 13, 2003 (Aug. 13, 2013), vol. 23, pp. 190-199.
Lin, "Salmon Calcitonin: Conformational Changes and Stabilizer Effects", AIMS Biophysics, 2015, 2(4): 695-723.
Lloyd et al. "Modelling the human immune response: performance of a 1011 human antibody repertoire against a broad panel of therapeutically relevant antigens", Protein Eng. , Design & Selectoon 22(3):159-168 (2009).
Lundin et al., "Phase 2 study of alemtuzumab (anti-CD52 monoclonal antibody) in patients with advanced mycosis fungoides/Sezary syndrome", Blood (2003) vol. 101, No. 11, pp. 4267-4272.
Makridis, et al., "MHC class I and II antigen expression and interferon ? treatment of human midgut carcinoid tumors," World Journal of Surgery, Aug. 1, 1993 (Aug. 1, 1993), vol. 16, Iss. 4, pp. 481-486.
Marcoval et al., "Angrogenesis and malignant melanoma. Angiogenesis is related to the development of vetical (tumorigenic) growth phase", J. Cutan. Pathol., 1997, 24:212-218.
Markovic et al., "A phase II study of ABT-510 (thrombospondin-1 analog) for the treatment of metastatic melanoma", Am. J. Clin. Oncol., 2007, 30(3):303-309.
Markovic at al., "A reproducible method for the enumeration of functional ( cytckine producing) versus non-functional peptide-specific cytotoxic T lymphocytes in human peripheral blood", Clin. Exo. Immnol., 2006, 145:438-447.
Markovic et al. "Peptide vaccination of patents with metastatic melanoma: improved clinical outcome in patients demonstrating effective immunization", Am J Clin Oncol., 2006, 29(4):352-360.
Matejtschuk, "Lyophilization of Proteins", Methods in Molecular Biology, Cryopreservation and Freeze-Drying Protocols: Second Edition, Edited by: J.G. Day and G.N. Stacey, Humana Press Inc., Totowa, NJ, 2007, vol. 368, pp. 59-72.
Matsuda et al., Preoperative oral immune-enhancing nutritional supplementation corrects TH1/TH2 imbalance in patients undergoing elective surgery for colorectal cancer, Dis. Colon Rectum, 2008, 49(4):507-518.
Mayo Clinic, "Paclitaxel Albumin-Stabilized Nanoparticle Formulation and Bevacizumab in Treating Patients With Stage IV Melanoma That Cannot Be Removed by Surgery", Dec. 19, 2013, ClinicalTrials.gov, URL:https://www.clinicaltrials.gov/ct2/show/NCT02020707 (Four (4) pages).
McElroy et al., "Imaging of Primary and Metatastic Pancreatic Cancer Using a Flurophore-Conjugated Anti-CA19-9 Antibody for Surgical Navigation", World J Surg., 2008. 32: 1057-1066.
Meadows et al. "Anti-VEGF Therapies in the Clinic," Cold Spring Harbor Perspectives in Medicine, Oct. 1, 2012 (Oct. 1, 2012), vol. 2, pp. 1-27.
Melcher, "Recommendatlons for influenza and pneumococcal vaccinations in people receiving chemotherapy", Clin Oncol (R Coll Radion), 2005, 17(1): 12-15.

Merchan et al., "Increased endothelial uptake of paclitaxel as a potential mechanism for its antiangiogenic effects: potentiation by Cox-2 inhibition", Int. J. Cancer, 2005, 113, pp. 490-498.
Mezzaroba et al., "New potential therapeutic approach for the treatment of B-Cell malignancies using chlorambucil/Hydroxychlorequine-Loaded Anti-CD20 Nanoparticles", Sep. 2103, PLoS One VOI. No. 8, Issue 9 pp. 1-10, e74216.
Middleton et al., "Randomized phase III study of temozolomide versus dacarbazine in the treatment of patients with advanced metastatic malignant melanoma", J. Clin. Oncol., 2000, 18, pp. 158-166.
Miller et al., "Paclitaxel plus Bevacizumab versus Paclitaxel Alone for Metastatic Breast Cancer," N Engl. J Med., (2007) vol. 357:2668-2676.
Mimura et al., Vascular endothelial growth factor inhibits the function of human mature dendritic cells mediated by VEGF receptor-2, Cancer Immunol Immunother., 2007, 56(6). pp. 761-770.
Mirtsching et al., "A Phase II Study of Weekly Nanoparticie Albumin-Bound Paclitaxel With or Without Trastuzumab in Metastatic Breast Cancer", Clinical Breast Cancer, 2011, 11(2):121-128.
Mocellin et al., "Cytokines and immune response in the tumor microenvironment", J Immunother., 2001, 24(5), pp. 392-407.
Motl, "Bevacizumab in combination chemotherapy for colorectal and other cancers", Am. J. Health-Svst. Pharm 2005, 62, pp. 1021-1032.
Nevala et al, "Abstract B77: Targeted nano-immune conjugates to melanoma: Preciinical testing of bevacizumab targeted nab-paclitaxel", Cancer Immunology Research, vol. 3, Oct. 1, 2015, 3 pages.
Nevala et al, "Antibody-targeted paclitaxel loaded nanoparticles for the treatment of CD20 B-cell lymphoma", Scientific Reports, vol. 7, Apr. 5, 2017, 9 pages.
Nevala et al, "Antibody-Targeted Chemotherapy for the Treatment of Melanoma", Cancer Research, vol. 76, No. 13, Jul. 1, 2016, pp. 3954-3964.
Nevala et al, "Targeted nano-immune conjugates to melanoma: Preclinical testing of bevacizumab targeted nab-paclitaxel", Proceedings of the AACR Special Conference: Tumor Immunology and Immunotherapy: A New Chapter, Dec. 1, 2014, 2 pages.
Ng et al., "Influence of formulation vehicle on metronomic taxane chemotherapy: albumin-bound versus cremophor EL-based paclitaxel", Clin. Cancer Res., 2006, 12, pp. 4331-4338.
Ng et al., "Taxane-mediated antiangiogenesis in vitro: influence of formulation vehicles and binding proteins", Cancer Res., 2004, 64, pp. 821-824.
Nilvebrant el al., "The Albumin-Binding Domain as a Scaffold for Protein Engineering". Computational and Structural Biotechnology Journal, Mar. 2013, vol. 6, Issue 7, e201303099, http://dx.doi.org/10.5936/csbj.201303099.
Nishida et al. English Translation of "Clinical Trials of New Drugs Cytotoxic Effect against Multiple Myeloma with High Expression of a CD38 Antigen and a Human CD38 Monoclonal Antibody Daratumumab:CD38 Antigen", history of Medicine, Sep. 29, 2012, vol. 242, No. 13, pp. 1176-1181.
International Search Report and Written Opinion corresponding to International Application No. PCT/US2017/023442 dated Jun. 16, 2017.
International Search Report and Written Opinion corresponding to International Application No. PCT/US2017/023443 dated Jul. 11, 2017.
Oku et al., "Tumor growth modulation by sense and antisense vascular endothelial growth factor gene expression: effects on angiogenesis, vascular permeability, blood volume, blood flow, fluorodeoxyglucose uptake and proliferation human melanoma intracerebral xenografts", Cancer Res., 1998, 58, pp. 4185-4192.
Ortaldo et al., "Effects of several species of human leukocyte interferon on cytotoxic activity o fNK cells and monocytes," International Journal of Cancer, Mar. 15, 1983 (Mar. 15, 1983) vol. 31, No. 3, pp. 285-289.
Ouichi, "Antibody delivery—from basics to clinical test—Clinical development of antibody-drug conjugate." Drug Deliv. Sys. 28(5):424-429 (2013).

(56) References Cited

OTHER PUBLICATIONS

Parikh et al., "The vascular endothelial growth factor famiy and its receptors", Hematol. Oncol. Clin. N. Am., 2004, 18, pp. 951-971.
Park et al., "Anti-HER2 Immunoliposomes: Enhanced Efficacy Attributable to Targeted Delivery", Clin. Cancer Res., 2002, 8, pp. 1172-1181.
Parker et al., "Targeting CLL Cells Using Rituximab-Conjugated Surface Enhanced Raman Scattering (SERS) Gold Nanoparticles," Blood vol. 116, No. 21, Nov. 1, 2010, pp. 1109.
Perez et al., "Phase 2 Trial of Carboplatin, Weekly Paclitaxel, and Biweekly Bevacizomab in Patents with Unresectable Stage IV Melanoma", Cancer, 2009, vol. 115, Issue 1, pp. 119-127.
Petrelli et al., "Targeted Delivery for Breast Cancer Therapy: the History of Nanopartide-Albumin-Bound Paclitaxel," Expert Opinion on Pharmacotherapy, Jun. 1, 2010 (Jun. 1, 2010), vol. 11, pp. 1413-1432.
Pikal., "Freeze-drying of proteins. Part II: Formulation selection", Biopharm, 1990, 9, pp. 26-30.
Polak et al., "Mechanisms of local immunosuppression in cutaneous melanoma", Br. J Lancer, 2007, 96(12), pp. 1879-1887.
Porrata et al., "Early lymphocyte recovery predicts superior survival after autologous hematepoletic stem cell transplantation in multiple myeloma or non-Hodgkin lymphoma", Blood, 2001, 98(3), pp. 579-585.
Porrata et al., "Timely reconstitution of immune competence affects clinical outcome following autologous stem cell transplantation", Clin Exp Med., 2004, 4(2):78-85.
Powell et al., "Adoptive transfer of vaccine-induced peripheral blood mononuclear cells to patients with metastatic melanoma following lymphodepletien", J Immnol., 2006, 177(9), pp. 6527-6539.
Pries et al. "Cytokines in head and neck cancer", Cytokine Growth Factor Rev., 2006, 17(3), pp. 141-146.
Qu Na et al; "Cabazitaxel-loaded human serum alhumin nanopartioles as a therapeutic agent against prostate cancer", International Journal of Nanomedicine, vol. 11, Jul. 25, 2016 (Jul. 26, 2016), pp. 3451-3459.
Ranieri et al., "Vascular endothelial growth factor (VEGF) as a target of bevacizumab in cancer, from the biology to the clinic", Curr. Med. Chem., 2006, 13, 1845-1857.
Rao et al., "Combination of Paclitaxel and Carboplatin as Second-Line Therapy Patients with Metastatic Melanoma", Cancer, Jan. 15, 2006, vol. 106, No. 2, pp. 375-382.
Ribas et al., "Anfitumor activity in melanoma and anti-self responses in a phase I trial with the anti-cytotoxic T lymphocyte-associated antigen 4 monoclonal antibody CP-675,206", J Clin Oncol., Dec. 10, 2005, 23(35), pp. 8968-8977.
Rosenberg et al., "Tumor progression can occur despite the induction of very high levels of self/tumor antigen- specific CD8+ T cells in patients with melanoma", J. Immunol., 2005, 175(9), pp. 6169-6176.
Roy et al., "Turner associated release of interleukin-10 alters the prolantin receptor and down-regulates prolactin responsiveness of immature cortical thymocytes", J Neuroimmunol., 2007, 186(1-2), pp. 112-120.
Rudikoff et al., "Single amino acid substitution altering antigen-binding specificity," Proc Natl Acad Sci USA 1962 vol. 79 pp. 1979-1983.
Rudnicka et al., "Rituximab causes a polarization of B cells that augments its therapeutic function of NK-cell-mediated antibody-dependent cellular cytotoxicity", Blood, 2013, 121(23):4694-4702.
Sadat et al., "Nano-pharmaceutical Formulations for Targeted Drug Delivery against HER2 in Breast Cancer", Current Cancer Drug Targets, 2015, 15(1):71-86.
Salven et al., "Enhanced expression of vascular endothelial growth factor in metastatic melanoma", Br. J. Cancer, 1997, 76(7), pp. 930-934.

Samaranayake et al., "Modified taxols. 5.1 Reaction of taxol with electrophilic reagents and preparation of a rearranged taxol derivative with tubulin assembly activity", J. Org. Chem., vol. 56, 1991, pp. 5114-5119.
Sandler et al., "Paclitaxel-carboplatin alone or with bevacizumab for non-small-cell lung cancer", N. Engl. J. Med., 2006, 355:2542-2550.
Sato et al., "Intraepithelial CD8+ tumor-infiltrating lymphocytes and a high CD8+/regulatory T cell ratio are associated with favorite prognosis in ovarian cancer", Proc Natl Acad Sci USA, 2005, 102(51):18538-18543.
Schrama et al. "Antibody targeted drugs as ancer therapeutics", Nature Reviews 5:147-159 (2006).
Sester et al., "Differonces in CMV-specific T-cell levels and long-term susceptibility to CMV infection after kidney, heart and king transplantation", Am J Transplant, 5(6):1483-1489, Jun. 2005.
Soda et al., "Latest topics of new medicine Albumin-bound paclitaxel," Mol. Respiratory Dis. 17(1):100-103 (Mar. 1, 2013).
Srivastava et al., "Angionesis in cutaneous melanoma: pathogenesis and clinical implications", Microsc. Res. Tech., 2003, 60:208-224.
Stancovski et al., "Mechanistic aspects of the opposing effects of monoclonal antibodies to the ERBB2 receptor on tumor growth," Proc Natl Acad Sci USA, 88: 8691-8695, (1991).
Streit et al., "Angiogenesis, lymohangiogenesis, and melanoma metastasis", Oncogene, 2003, 22. pp. 3172-3179.
Taieb et al., "Chemoimmunotherapy of tumors: Cyclophosphamide synergizes with exoxome based vaccines", J. Immunol., Mar. 1, 2006, 176(5):2722-2729.
Tao et al., "inhibiting the growth of malignant melanoma by blocking the expression of vascular endothelial growth factor using an RNA interference approach", Br. J. Dermatol., 2005, 153:715-724.
Tas et al,. "Circulating serum levels of angiogenic factors and vascular endothelial growth factor receptors 1 and 2 in melanoma patients", Melanoma Res., 2006, 16:405-411.
Terheyden at al., "Anti-vascular endothelial growth factor antibody bevacizumab in conjunction with chemotherapy in metastasizing melanoma", J Cancer Res Clin Oncol, 2007, 133(1), pp. 897-901.
Terui, English Translation of Molecular-Targeted Therapy for Cancer: Progresses and Challenges, "Daratumumab, Antibody Drug against Myeloma", Pharma Med., Nov. 10, 2013. vol. 31, No. 11, p. 27-30.
Ugurel et al., "Increased serum concentration a angiogenic factors in malignant melanoma patients correlates with tumor progression and survival", J. Clin. Oncol., 2001, 19:577-583.
Vacca et al., "Docetaxel versus paclitaxel for antiangiogenesis", J. Hematother. Stem Cell Res., 2002, 11:103-118.
Varker et al., "A randomized phase 2 trial of bevaclzumab with or without daily low-dose interferon alfa-2b in metastatic malignant melanoma", Ann Srug Oncol., 14(8)L2367-2376, print Aug. 2007, Epub May 2007.
Vence et al., "Circulating tumor antigen-specific regulatory T cells in patients with metastatic melanoma", Prop Natk Acad Sci USA, 2007, 104(52), pp. 20854-20889.
Vishnu et al., "Safety and Efficacy of nab-Paclitaxel in the Treatment of Patients with Breast cancer," Breast Cancer: Basic and Canical Research. 2011. vol. 5, pp. 53-65.
Volk et al., "Nab-paclitaxel efficacy in the orthotopic model of human breast cancer is signigicantly enhanced by concurrent anti-vascular endothelial growth factor A therapy," Neoplasia 10(6):613-623 (2008).
Wagner et al., "Enhanced drug targeting by attachment of an anti alphav integrin antibody to doxorubicin loaded with human serum albumin nanoparticles", Biomaterials, 31(8):2388-2398, Epub Dec. 23, 2009.
Walker et al., "Monitoring Immune response in cancer patients receiving tumor vaccines", Int Rev Immunol., 2003, 22(3-4):283-319.
Wang et al., "Biofunctionalized targeted nanopartieies for therapeutic applications", Expert Opin. Biol. Ther., 2008, 8(8): 1063-1070.
Wang et al., "Paclitaxel at ultra low concentrations inhibits angi-egenesis without affecting cellular microtubule assembly", Anti-Cancer Drugs, 2003, vol. 14, Issue 1, pp. 13-19.

(56) References Cited

OTHER PUBLICATIONS

Washington University School of Medicine "Phase I/II Study of Abraxane in Recurrent and Refractory Lymphoma", ClinicalTrials.gov, Dec. 6, 2016, 7 pages.
Weber, "Review anti-CTLA-4 antibody ipilimumab, case studies of clinical response and immune-related adverse events", Oncologist, Jul 2007, 12(7), pp. 864-872.
Wiernik et al., "Phase I trial of taxel given as a 24-hour infusion every 21 days: responses observed in metastatic melanoma", Journal of Clinical Oncology, Aug. 1987, vol. 5, No. 8, pp. 1232-1239.
Wong et al., "Programmed death-1 blockade enhances expansion and functional capacity of human melanoma antigen-specific CTLs", Int. Immunol., 2007, vol. 19 No. 10, pp. 1223-1234.
Wu et al., "Aptamers: Active Targeting Ligands for Cancer Diagnosis and Therapy", Theranostics, 2015 5(4):322-344.
Yardley et al., "A pilot study of adjuvant nanoparticle albumin-bound (nab) paclitaxel and cyclophosphamide, with trastuzumab in HER2-positive patients, in the treatment of early-stage breast cancer", Breast Cancer Res Treat, 2010, 123:471-475.
Yee at al., "Adoptive T cell therapy using antigen-specitic CD8+ T cell clones for the treatment of patients with metastatic melanoma: in vivo persistence, migration, and antitumor effect of transferred T cells", Proc Natl Acad Sci USA, 2002, 99(25):16168-16173.
Yu et al., "Interaction between bevacizumab and murine VEGF-A: a reassessment," Invest. Ophthalmol. Visual Sci. 49(2): 522-527, Feb. 2008.
Yuan et al., "Vascular Permeability in a Human Tumor Xenograft: Molecular Size Dependence and Cutoff Size", Cancer Research, Sep. 1. 1995, 55. pp. 3752-3756.
Yuan et al., "Time-dependent vascular regress on and permeability changes in established human tumor xenografts induced by an anti-vascular endothelial growth factor/vascular permeability factor antibody," Proc. Natl. Acad. Sci. USA 93(25):14765-14770 (1996).
Zimpfer-Rechner et al., "Randomized phase II study of weekly paclitaxel versus paclitaxel and carboplatin as second-line therapy in disseminated melanoma: a multicentre trial of the Dermatclogic Co-operative Oncology Group (DeCOG)", Melanoma Res., 2003, 13:531-536.
Anonymous, "Phase I/II Study of Abraxane in Recurrent and Refractory Lymphoma", NCT01555853, ClinicalTrials.gov, Jun. 6, 2014 (8 pages).
U.S. Appl. No. 15/092,403, office action dated May 23, 2019.
U.S. Appl. No. 15/092,433, office action dated May 30, 2019.
U.S. Appl. No. 15/225,542, office action dated Jul. 18, 2019.
U.S. Appl. No. 15/412,581, office action dated Mar. 8, 2019.
U.S. Appl. No. 15/412,610, office action dated Mar. 14, 2019.
U.S. Appl. No. 15/414,526, office action dated Mar. 12, 2019.
U.S. Appl. No. 15/414,533, office action dated Mar. 8, 2019.
U.S. Appl. No. 15/430,411, office action dated May 1, 2019.
U.S. Appl. No. 15/452,669; office action dated Jun. 24, 2019.
U.S. Appl. No. 15/456,377; office action dated Mar. 19, 2019.
U.S. Appl. No. 15/456,377; office action dated Jul. 5, 2019.
U.S. Appl. No. 15/456,382; office action dated Mar. 18, 2019.
U.S. Appl. No. 15/456,382; office action dated Jul. 8, 2019.
U.S. Appl. No. 15/456,391; office action dated Mar. 15, 2019.
U.S. Appl. No. 15/456,391: office action dated Jul. 24, 2019.
U.S. Appl. No. 15/456,395; office action dated Mar. 28, 2019.
U.S. Appl. No. 15/456,399; office action dated Mar. 28, 2019.
U.S. Appl. No. 15/460,552; office action dated Apr. 1, 2019.
U.S. Appl. No. 15/460,699; office action dated Mar. 28, 2019.
U.S. Appl. No. 15/461,288; office action dated Apr. 1, 2019.
Bedu-Addo "Understanding Lyophilization Formulation Development", Pharamceutical Technology Lyophilization. pp. 10-18 (2004).
Beers et al. "CD20 as a Target for Therapeutic Type I and II Monocolonal Antibodies", Seminars in Hematology 47(2):107-114 (2010).
Belldegrun et al. "Human Renal Carcinoma Line Transfected with Interleukin-2 and/or Interferon alpha Gene(s): Implications for Live Cancer Vaccines", J Natonal Cancer Institute 85(3):207-216 (1993).
Buechner "Intralesional interferon alfa-2b in the treatment of basal cell carcinoma", J Am Acad Dermatol 24:731-734 (1991).
Dheng et al, Molecularly targeted drugs formetastatic colorectal cancer. Drug Des Devel Ther. Nov. 1, 2013;7: 1315-22 (Year: 2013).
Coiffier "The Role of Rituximab in Lymphomas", Rev. Bras. Hematol. Hemoter., 2002, vol. 24, No: 3, ISSN: 1516-8484 (6 pages).
Doveil et al. "Adjuvant Therapy of Stage IIIb Melanoma with interferon Alfe-2b:Clinical and Immunological Relevance", Dermatology 191:234-239 (1995).
Edwards at al. The Remarkable Flexibility of the Human Antibody Repertoire: Isolation of Over One Thousand Different Antibodies to a Single Protein, BLyS J. Mol. Biol 334: 103-118 (2003).
European Application No. 16837869.3, Extended European Search Report dated Apr. 4, 2019.
European Application No. 17736453.6, Extended European Search Report dated Jul. 8, 2019.
International Preliminary Report on Patentability for Application No. PCT/US2017/045643, dated Feb. 14, 2019.
International Preliminary Report on Patentability for Application No. PCT/US2017/049745, dated Mar. 14, 2019.
International Preliminary Report on Patentability for Application No. PCT/US2017/049746, dated Mar. 14, 2019.
International Preliminary Report on Patentability for Application No. PCT/US2017/050137 dated Mar. 21, 2019.
lqbal et al. Anti-Cancer Actions of Denosumab. Curr Osteoporos Rep. Dec. 2011;9(4): 173-6 (Year: 2011).
Khallouf et al. "5-Fluorouracil and Interferon-alpha Immunochemotherapy Enhances Immunogenicity of Murine Pancreatic Cancer Through Upregulation of NKG2D Ligands and MHC Class 1", Immunother 35(3):245-293 (2012).
Korthals et al. "Monocyte derived dendritic cells generated by IFN-alpha acquire mature dendritic and natural killer cell properties as shown by gene expression analysis", J Transiated Medicine 5:46 (2007) (11 pages).
Matthay et al. Promising therapeutic targets in neuroblastoma. Clin Cancer Res. May 15, 2012;18(10):2740-53. (Year: 2012).
Package Insert, Campath® (ALEMTUZUMAB), Millennium and ILEX Partners, LP, 13 pages, available May 2001.
Reck et al. "Ipllimumab in combination with paolitaxel and carboplatin as first-line therapy in extensive-disease-small-cell lung cancer results from a randomized, double-blind, multicenter phase 2 trial", Ann Oncol. 24(1):75-83 (2013).
Robak T. Emerging monoclonal antibodies and related agents for the treatment of chronic lymphocytic leukemia. Future Oneal. Jan. 2013:9(1):69-91. Abstract Only. (Year: 2013).
Verma et al. "Effect of surface properties on nenoparticle-cell interactions" , Small. 6(1 ): 12-21. (2010).
Summons to attend oral proceeding in European patent application 17778387.5 dated Aug. 20, 2021, 5 pages.
Office Action in copending Japanese Patent Application 2019-511962, dated Jun. 2, 2021, 9 pages (with translation).
First Office Action dated Jan. 24, 2022, for Chinese Application No. 201780067542.2 Filing Date Aug. 31, 2017, 6 pages.
Search Report dated Jan. 12, 2022 for Chinese Application No. 201780067542.2 Filing Date Aug. 31, 2017, 3 pages.
Notice of Preliminary Rejection dated Jan. 10, 2022, for Korean Patent Application No. 10-2019-7009302, with Translation (16 pages).
Final Office Action in copending Japanese Patent Application 2019-511962, dated Dec. 10, 2021, 2 pages.
Hasan Kouchakzadeh et al., "Efficient Delivery of Therapeutic Agents by Using Targeted Albumin Nanoparticles", Advances in Protein Chemistry and Structural Biology, 2015, vol. 98, p. 121-143.
U.S. Appl. No. 15/225,542; office action dated Jul. 30, 2020.
U.S. Appl. No. 15/286,024, office action dated Feb. 10, 2020.
U.S. Appl. No. 15/286,024, office action dated Jul. 29, 2020.
U.S. Appl. No. 15/359,569; office action dated Aug. 10, 2020.
U.S. Appl. No. 15/430,411, office action dated Apr. 17, 2020.
U.S. Appl. No. 15/452,669; office action dated Mar. 3, 2020.
U.S. Appl. No. 15/456,377; office action dated Mar. 12, 2020.
U.S. Appl. No. 15/456,391; office action dated Feb. 4, 2020.

(56) References Cited

OTHER PUBLICATIONS

U.S. Appl. No. 15/460,699; office action dated Mar. 3, 2020.
U.S. Appl. No. 15/461,288; office action dated Feb. 28, 2020.
U.S. Appl. No. 15/675,596; office action dated May 28, 2020.
U.S. Appl. No. 15/752,155; office action dated Feb. 7, 2020.
U.S. Appl. No. 16/328,146; office action dated Feb. 26, 2020.
U.S. Appl. No. 16/328,146; office action dated Jul. 28, 2020.
Barua et al. "Particle shape enhances specificity of antibody-display nanoparticles", PNAS 110(9):3270-3275 (2013).
Chuang et al. "Recombinant human serum albumin", Drugs Today 43(8):547-561 (2007) (Abstract Only) (2 pages).
European Application No. 17750912.2 Extended European Search Report dated Jan. 2, 2020.
Miele et al. "Albumin-bound formulation of paclitaxel (Abraxane® ABI-007) in the treatment of breast cancer", International Journal of Nanomedicine 4:99-105 (2009).
Warner et al. "Alemtuzumab use in relapsed and refractory chronic lymphocytic leukemia: a history and discussion of future rational use", Ther Adv Hematol 3(6):375-389 (2012).
Zhao et al. "Abraxane, the Nanoparticle Formulation of Paclitaxel Can Induce Drug Resistance by Ip-Regulation of P-gp", PLoS One 10(7):e0131429 (2015) (19 pages).
Office Action for Israel Patent Application 265087 dated Feb. 17, 2022, 9 pages, with English Summary of office action (redacted).
"U.S. Appl. No. 15/430,411, office action dated Nov. 2, 2020".
"U.S. Appl. No. 15/452,669; office action dated Oct. 21, 2020".
"U.S. Appl. No. 15/456,377; office action dated Sep. 1, 2020".
"U.S. Appl. No. 15/675,596; office action dated Oct. 20, 2020".
"U.S. Appl. No. 16/086,977; office action dated Sep. 3, 2020".
"U.S. Appl. No. 16/330,028; office action dated Nov. 24, 2020".

* cited by examiner

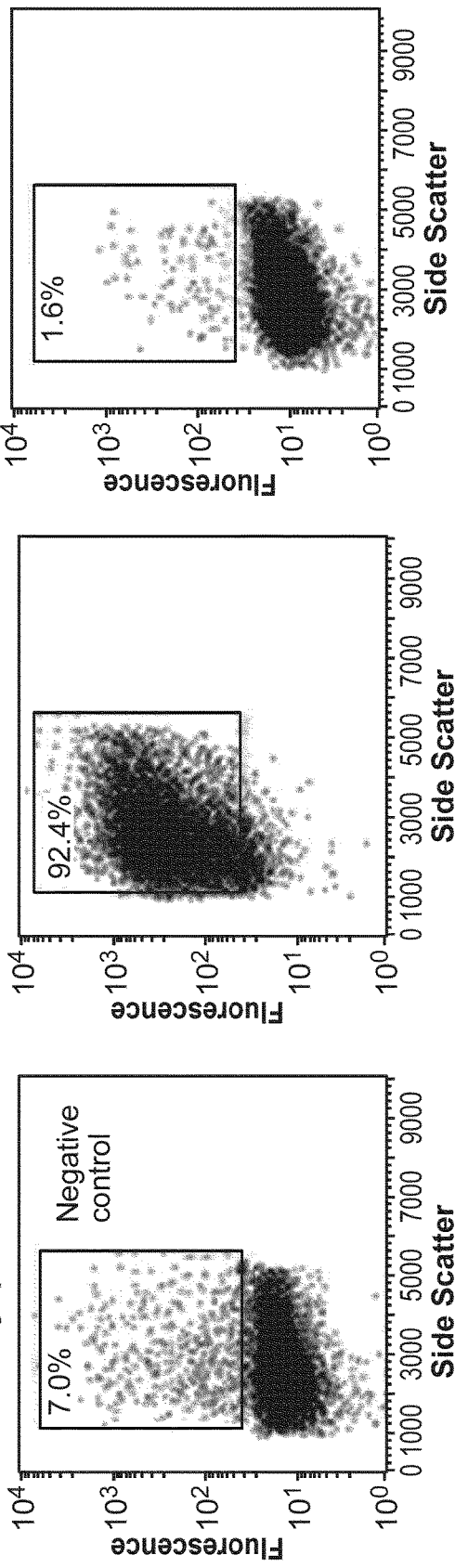
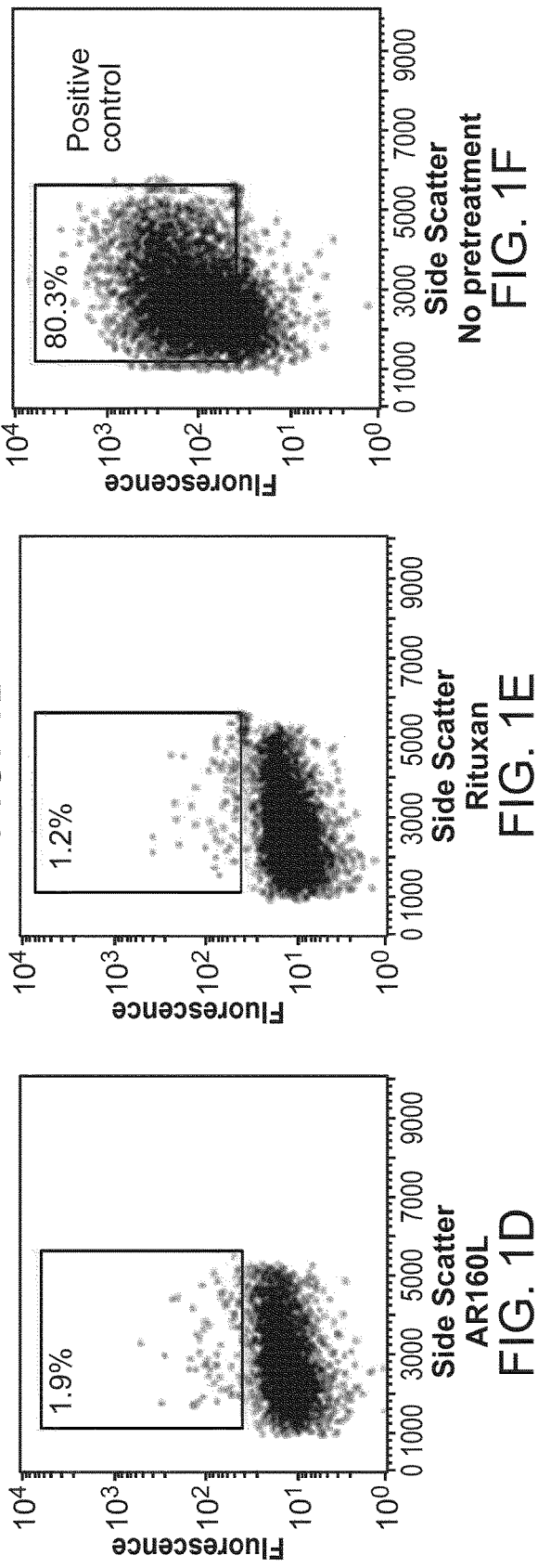

CARRIER-PD-L1 BINDING AGENT COMPOSITIONS FOR TREATING CANCERS

CROSS REFERENCE TO RELATED APPLICATIONS

This application is a 35 U.S.C. § 371 national phase application of PCT Application PCT/US2017/049746 filed Aug. 31, 2017, which claims the benefit of the priority date of U.S. Provisional Application No. 62/382,731, filed Sep. 1, 2016; the entire contents of each of which are incorporated by reference herein in its entirety.

FIELD OF THE INVENTION

This application relates to novel compositions of binding agents and carrier proteins and methods of making and using the same, in particular, as a cancer therapeutic.

BACKGROUND

Chemotherapy remains a mainstay for systemic therapy for many types of cancer, including melanoma. Most chemotherapeutic agents are only slightly selective to tumor cells, and toxicity to healthy proliferating cells can be high (Allen T M. (2002) *Cancer* 2:750-763), often requiring dose reduction and even discontinuation of treatment. In theory, one way to overcome chemotherapy toxicity issues as well as improve drug efficacy is to target the chemotherapy drug to the tumor using antibodies that are specific for proteins selectively expressed (or overexpressed) by tumors cells to attract targeted drugs to the tumor, thereby altering the biodistribution of the chemotherapy and resulting in more drug going to the tumor and less affecting healthy tissue. Despite 30 years of research, however, specific targeting rarely succeeds in the therapeutic context.

Conventional antibody dependent chemotherapy (ADC) is designed with a toxic agent linked to a targeting antibody via a synthetic protease-cleavable linker. The efficacy of such ADC therapy is dependent on the ability of the target cell to bind to the antibody, the linker to be cleaved, and the uptake of the toxic agent into the target cell. Schrama, D. et al. (2006) *Nature reviews. Drug discovery* 5:147-159.

Antibody-targeted chemotherapy promised advantages over conventional therapy because it provides combinations of targeting ability, multiple cytotoxic agents, and improved therapeutic capacity with potentially less toxicity. Despite extensive research, clinically effective antibody-targeted chemotherapy remains elusive: major hurdles include the instability of the linkers between the antibody and chemotherapy drug, reduced tumor toxicity of the chemotherapeutic agent when bound to the antibody, and the inability of the conjugate to bind and enter tumor cells. In addition, these therapies did not allow for control over the size of the antibody-drug conjugates.

There remains a need in the art for antibody-based cancer therapeutics that retain cytotoxic effect for targeted drug delivery to provide reliable and improved anti-tumor efficacy over prior therapeutics.

The programmed cell death protein-1 (PD-1, also known as CD279, hereinafter "PD-1") receptor is expressed on the surface of activated T cells, B cells, as well as myeloid cells. PD-1 ligands include programmed death ligand-1 (PD-L1, also known as B7-H1, CD274, hereinafter "PD-L1") and programmed death ligand-2 (PD-L2, also known as B7-DC and CD273, hereinafter "PD-L2"), and are commonly expressed on the surface of dendritic cells or macrophages. PD-L1 is expressed on many tumors including cancers developing in various organs such as head and neck, lung, stomach, colon, pancreas, breast, kidney, bladder, ovary, cervix, as well as melanoma, glioblastoma, multiple myeloma, lymphoma, and various leukemias. PD-L1 is commonly over-expressed on the surface of tumor cells, for example, metastatic non-small cell lung carcinomas (NSLC).

When binding to the PD-1 receptors of activated T cells, the PD-L1 expressing tumor cells can exploit the inhibitory signaling of the PD-1 pathway, thereby limiting or even halting a host's own anti-tumor immune responses from T cells. On the flip side of this inhibitory signaling, the blocking or interference of the interaction of PD-1 to PD-L1/PD-L2 would disrupt the inhibition signaled by the pathway. As such, immunotherapies based on antibodies against PD-1, PD-L1 or PD-L2 aim to overcome such immune response resisting ability of tumors and to restore or re-stimulate a host's own immune mechanism against tumors.

Accordingly, there is a need for increasing the therapeutic effectiveness of an immunotherapy treatment of a patient suffering from a cancer which expresses PD-L1 or PD-L2.

SUMMARY

It has been unexpectedly and surprisingly found that the therapeutic effectiveness of an immunotherapy treatment of a patient suffering from a cancer which expresses PD-L1 or PD-L2 can be increased by the administration of (a) a therapeutically effective amount of nanoparticles or a nanoparticle composition as described herein, wherein the nanoparticles are capable of binding to PD-L1 or PD-L2, and (b) a PD-1 immunotherapy.

Both anti-PD-1 and anti-PD-L1 antibodies have been developed and approved for treating various cancers. Anti-PD-1 antibodies include, but are not intended to be limited to, Nivolumab (OPDIVO®), developed by Bristol-Myers Squibb U.S. and approved in the U.S. for treatment of metastatic melanoma and squamous NSCL cancer; Pembrolizumab (KEYTRUDA®), developed by Merck U.S. and approved for treatment of metastatic melanoma. Anti-PD-L1 antibodies include, but are not intended to be limited to, atezolizumab (TECENTRIQ®), developed by Roche, Switzerland (Genentech U.S.) and approved for treatment of the most common type of bladder cancer, i.e., urothelial carcinoma; BMS-936559/MDX-1105 (Bristol Myers Squibb), MeDI4736 (MedImmune/AstraZeneca), and MSB00100718C (EMD Serono). See, e.g., Philips and Atkins "Therapeutic uses of anti-PD-1 and anti-PD-L1 antibodies" International Immunology Vol. 27(1) pp. 39-46.

Atezolizumab is a humanized monoclonal antibody targeting the PD-1 pathway so as to block the immune checkpoint inhibition signaled thereby. The PD-1 pathway refers herein to the signaling of the inhibition of T cell immune responses upon the interaction of the PD-1 and PD-L1/PD-L2. Therapies using other anti-PD-L1 antibodies (e.g., avelumab, durvalumab, BMS 936559,) for treating various other types of cancers including, for example, non-squamous NSCLC, renal cell carcinoma and bladder cancer, are under investigation and development as well.

Like PD-L1, PD-L2 binds to PD-1. Human PD-L1 and PD-L2 are reported to share about 41 percent of amino acid sequence identity with each other and have similar functionality. The binding of PD-L2 with PD-1 also inhibits T cell proliferation as well as cytokine production, demonstrating a similar inhibitory regulation of T cell immune responses. Therapies using anti-PD-L2 antibodies for treating various other types of cancers including, for example, non-squamous NSCLC, renal cell carcinoma and bladder cancer, are also under investigation and development.

According to the present invention, the nanoparticles comprise (a) carrier protein (b) a first binding agent, and (c) optionally a therapeutic agent, wherein the nanoparticles are capable of binding to PD-L1 or PD-L2. In a preferred embodiment, the nanoparticles are held together by non-covalent bonds between one or more of the components of the nanoparticles (carrier protein, binding agents, and/or therapeutic agent).

In one aspect, a method for treating a patient suffering from a cancer which expresses PD-L1 or PD-L2 is provided, where the method comprises administering to the patient (a) nanoparticles (or a nanoparticle composition comprising nanoparticles), wherein each of the nanoparticles comprise a carrier protein, first binding agents having an antigen binding portion, wherein said antigen is PD-L1 or PD-L2, and optionally at least one therapeutic agent, wherein the nanoparticles are capable of binding to PD-L1 or PD-L2, and (b) a PD-1 immunotherapy. In one embodiment, the PD-1 immunotherapy comprises a second binding agent capable of binding to PD-1.

In another aspect, the present invention relates to a method for increasing the therapeutic effectiveness of an immunotherapy treatment of a patient suffering from a cancer which expresses PD-L1 or PD-L2, the method comprising administering to the patient (a) a therapeutically effective amount of a nanoparticle composition as described herein, and (b) a PD-1 immunotherapy. In one embodiment, the PD-1 immunotherapy comprises administering a second binding agent capable of binding to PD-1.

In one aspect, the present invention relates to a method for treating a patient suffering from a cancer which expresses PD-L1 or PD-L2, where the method comprises administering to the patient (a) nanoparticles (or a nanoparticle composition comprising nanoparticles), wherein each of the nanoparticles comprise albumin, antibodies having an antigen-binding portion, wherein said antigen is PD-L1 or PD-L2, and paclitaxel; such that the nanoparticles are capable of binding to PD-L1 or PD-L2, and (b) a PD-1 immunotherapy. In one embodiment, the PD-1 immunotherapy comprises a second antibody capable of binding to PD-1 (an anti-PD-1 antibody). In one embodiment, the antibody is an anti-PD-L1 antibody. In one embodiment, the antibody is an anti-PD-L2 antibody.

In some embodiments, a CTLA-4 immunotherapy is administered to the patient in combination with the nanoparticles that are capable of binding PD-L1 or PD-L2. In one embodiment, the CTLA-4 immunotherapy is administered in addition to the PD-1 immunotherapy. In one embodiment, the CTLA-4 immunotherapy is administered instead of the PD-1 immunotherapy. In one embodiment, the CTLA-4 immunotherapy is an anti-CTLA-4 antibody.

In one aspect, each of the nanoparticles of the nanoparticle composition comprises between about 400 to about 1000 said first binding agents.

In some aspects, the first binding agents are aptamers. In some aspects, the second binding agent of the PD-1 immunotherapy is an aptamer.

In some aspects, the first binding agents are antibodies (e.g., anti-PD-L1 antibodies or anti-PD-L2 antibodies). In some aspects, the second binding agent of the PD-1 immunotherapy is an antibody (e.g., an anti-PD-1 antibody). In some aspects, the anti-PD-1 antibody comprises nivolumab, pembrolizumab, pidilizumab, PDR001, or biosimilars thereof. In some aspects, the anti-PD-L1 antibody is atezolizumab, avelumab, durvalumab, or BMS 936559 (MDX1105). In some aspects, the binding agent of the CTLA-4 immunotherapy is an anti-CTLA-4 antibody. In one embodiment, the anti-CTLA-4 antibody is ipilimumab.

In some aspects, the first binding agent and/or the second binding agent is a fusion protein. In one embodiment, the fusion protein is AMP-224 (PD-L2 IgG2a fusion protein; Amplimmune/GlaxoSmith Klein); AMP-514 (MEDI0680) (PD-L2 fusion protein; Amplimmune/GlaxoSmith Klein), or a biosimilar thereof.

In some aspects, the nanoparticles or nanoparticle composition is lyophilized.

In some aspects, the second binding agent of the PD-1 immunotherapy is a free binding agent, wherein the free binding agent is not complexed with or otherwise integrated onto and/or into a nanoparticle composition.

In some aspects, PD-1 immunotherapy is an immunotherapy nanoparticle composition comprising the second binding agent complexed with or integrated onto and/or into a nanoparticle composition, wherein the immunotherapy nanoparticle composition comprises a carrier protein and said second binding agent.

In some aspects, the second binding agent of the immunotherapy nanoparticle composition is an antibody. In some aspects, the second binding agent of the immunotherapy nanoparticle composition is an anti-PD-1 antibody. In some aspects, the antibody of the immunotherapy nanoparticle composition comprises atezolizumab, nivolumab, pembrolizumab, avelumab or durvalumab, pidilizumab, BMS 936559, PDR001, or a biosimilar thereof.

In some aspects, the second binding agent of the immunotherapy nanoparticle composition is a fusion protein. In one embodiment, the fusion protein is AMP-224 (PD-L2 IgG2a fusion protein; Amplimmune/GlaxoSmith Klein); AMP-514 (MEDI0680) (PD-L2 fusion protein; Amplimmune/GlaxoSmith Klein), or a biosimilar thereof.

In some aspects, the second binding agent of the immunotherapy nanoparticle composition is an aptamer. In some aspects, the second binding agent of the immunotherapy nanoparticle composition is a PD-1 aptamer.

In some aspects, the immunotherapy nanoparticle and/or nanoparticle composition is lyophilized.

In some aspects, the nanoparticle composition and the PD-1 immunotherapy are administered sequentially. In some aspects, the nanoparticle composition is administered prior to administration of the PD-1 immunotherapy. In some aspects, the PD-1 immunotherapy is administered prior to administration of the nanoparticle composition. In some aspects, the nanoparticle composition and the PD-1 immunotherapy are administered concurrently.

In some embodiments, the present invention relates to a method for increasing the therapeutic effectiveness of an immunotherapy treatment of a patient suffering from a cancer which expresses PD-L1 or PD-L2. In one embodiment, the method comprises administering to the patient a therapeutically effective amount of the nanoparticles or nanoparticle composition as described herein, and a PD-1 or CTLA-4 immunotherapy comprising a second binding agent. In one embodiment, the second binding agent is capable of binding to PD-1 or CTLA-4. In one embodiment, PD-1 or CTLA-4 immunotherapy comprises nanoparticles comprising a carrier protein (e.g., albumin) and the second binding agent, and optionally a therapeutic agent (e.g., paclitaxel).

In some embodiments, the present invention relates to a method for treating a patient suffering from a cancer which expresses PD-L1 or PD-L2. In some embodiments, the method comprises administering to the patient a therapeutically effective amount of a nanoparticle composition as described herein, and administering top the patient an immunotherapy comprising a second binding agent, wherein the binding agents of the nanoparticle composition are capable of binding to PD-L1, PD-L2, or PD-1, and the second binding agent of the immunotherapy is capable of binding to PD-L1, PD-L2, or PD-1.

Without being bound by theory, the binding agent is believed to be bound by the carrier protein through hydrophobic interactions, which, by their nature, are weak. Yet the activity of the individual components, as well as their relative relationship in the nanoparticle are preserved despite lyophilization and reconstitution of the composition. It is still further contemplated that binding to the carrier protein, e.g., complexation of the binding agent to the carrier protein, occurs through an albumin binding motif on the binding agent, and/or an antibody-binding motif on the carrier protein. Albumin-binding motifs and antibody-binding motifs are described in PCT Application No. PCT/US17/45643, filed Aug. 4, 2017, which is incorporated herein by reference in its entirety. In some embodiments, the binding agent is a non-therapeutic and non-endogenous human antibody, a fusion protein, or an aptamer.

Further challenges are imposed because the nanoparticles are used in therapy.

While rearrangement of the hydrophobic components in the nanoparticle may be mitigated through covalent bonds between the components, such covalent bonds pose challenges for the therapeutic use of nanoparticles in cancer treatment. The binding agent, carrier protein, and additional therapeutic agent typically act at different locations in a tumor and through different mechanisms. Non-covalent bonds permit the components of the nanoparticle to dissociate at the tumor. Thus, while a covalent bond may be advantageous for lyophilization, it may be disadvantageous for therapeutic use.

The size of nanoparticles, and the distribution of the size, is also important. Nanoparticles may behave differently according to their size. At large sizes, nanoparticles or the agglomeration of the particles may block blood vessels either of which can affect the performance and safety of the composition.

When administered intravenously, large particles (e.g. greater than 1 µm) are typically disfavored because they can become lodged in the microvasculature of the lungs. At the same time, larger particles can accumulate in the tumor or specific organs. For example, TheraSphere® 20-60 micron glass particles that are injected into the hepatic artery feeding a tumor of the liver for the delivery of a radioactive element, also known as radioembolization, are in clinical use for liver cancer.

Therefore, for intravenous administration, particles under 1 µm are used. Particles over 1 µm are, more typically, administered directly into a tumor ("direct injection") or into an artery feeding into the site of the tumor.

Finally, cryoprotectants and agents that assist in the lyophilization process must be safe and tolerated for therapeutic use.

Without wishing to be bound by theory, the binding agent is believed to be bound to the carrier protein through hydrophobic interactions which, by their nature, are weak. Yet, the activity of the individual components, and their relative relationship in the nanoparticle are still achieved despite lyophilization and reconstitution of the composition.

In one aspect, provided herein are nanoparticle compositions comprising nanoparticles wherein each of the nanoparticles comprises a carrier protein, binding agents, and optionally at least one therapeutic agent, wherein the binding agents are arranged outward from the surface of the nanoparticles and wherein the nanoparticles are capable of binding to PD-L1, PD-L2, or PD-1 in vivo.

In another aspect, provided herein are nanoparticle compositions comprising nanoparticles wherein each of the nanoparticles comprises a carrier protein that is not albumin, binding agents, and optionally at least one therapeutic agent, wherein the binding agents are arranged on an outside surface of the nanoparticles and wherein the nanoparticles are capable of binding to PD-L1, PD-L2, or PD-1 in vivo. In one embodiment, the nanoparticles comprise between about 100 to about 1000 binding agents, preferably about 400 to about 800 binding agents. When nanoparticles multimerize, the number of binding agents is increased proportionally. For example, if a 160 nm nanoparticle contains 400 binding agents, a 320 nm dimer contains about 800 binding agents.

In another aspect, provided herein are nanoparticle compositions comprising nanoparticles, wherein each of the nanoparticles comprises carrier protein binding agents, and optionally at least one therapeutic agent that is not paclitaxel, wherein the nanoparticles are capable of binding to PD-L1, PD-L2, or PD-1 in vivo. In one embodiment, the nanoparticles further comprise paclitaxel. In one embodiment, the binding agents are arranged on a surface of the nanoparticles such that a binding portion of the binding agent (e.g., variable region of an antibody) is directed outward from that surface.

In other embodiments, the nanoparticles multimerize, e.g. dimerize. Multimerization may be observed as multiples of the weight or size of the unit molecule, e.g. 160 nm particles multimerize to about 320 nm, 480 nm, 640 nm, etc. In some embodiments, less than 20% of the nanoparticles in a population are multimers. In some embodiments, more than 80% of the nanoparticles in a population are multimers.

In one embodiment, the weight ratio of carrier-bound drug to binding agent (e.g., albumin-bound paclitaxel and anti-PD-L1 or anti-PD-L2 antibody) is between about 5:1 to about 1:1. In one embodiment, the weight ratio of carrier-bound drug to binding agent is about 10:4. In one embodiment, the binding agents are a substantially single layer on all or part of the surface of the nanoparticle. In one embodiment, less than 0.01% of nanoparticles in the composition have a size selected from greater than 200 nm, greater than 300 nm, greater than 400 nm, greater than 500 nm, greater than 600 nm, greater than 700 nm and greater than 800 nm. Larger sizes are believed to be the result of multimerization of several nanoparticles, each comprising a core and binding agent coating on all or part of the surface of each nanoparticle.

The invention further includes lyophilized compositions, and lyophilized compositions that do not materially differ from, or are the same as, the properties of freshly-prepared nanoparticles. In particular, the lypholized composition, upon resuspending in aqueous solution, is similar or identical to the fresh composition in terms of particle size, particle size distribution, toxicity for cancer cells, binding agent affinity, and binding agent specificity. Surprisingly, lyophilized nanoparticles after resuspension retain the properties of freshly-made nanoparticles, notwithstanding the presence of two different protein components in these particles.

In one aspect, this invention relates to lyophilized nanoparticles or a lyophilized nanoparticle composition comprising nanoparticles, wherein each of the nanoparticles comprises a carrier-bound drug core and an amount of binding agent that binds PD-L1, PD-L2 or PD-1. In one embodiment, the binding agent is arranged on a surface of the core such that a binding portion of the binding agent is directed outward from that surface, wherein the binding agents retain their association with the outside surface of the nanoparticle upon reconstitution with an aqueous solution. In one embodiment, the lyophilized composition is stable at room temperature for at least about 3 months, 4 months, 5 months, 6 months, 7 months, 8 months, 9 months, 10 months, 11 months, 12 months, or longer. In one embodiment, the lyophilized composition is stable at room temperature for at least 3 months. In one embodiment, the reconstituted nanoparticles retain the activity of the therapeutic agent and are capable of binding to the target in vivo. In another embodiment, the composition is stable at about 20° C. to about 25° C. for up to about 12 months or longer.

In one embodiment, the average reconstituted nanoparticle size is from about 90 nm to about 1 μm. In a preferred embodiment, the average reconstituted nanoparticle size is from about 100 nm to about 200 nm, and more preferably about 100 nm to about 160 nm. In one embodiment, in the average reconstituted nanoparticle size is from greater than 800 nm to about 3.5 μm, comprising multimers of smaller nanoparticles, e.g. multimers of 90-200 nm nanoparticles. In one embodiment, the weight ratio of core to binding agent is from greater than 1:1 to about 1:3. In one embodiment, in the average reconstituted nanoparticle size is about 90 nm to about 225 nm.

In one aspect, this disclosure relates to lyophilized nanoparticles or a lyophilized nanoparticle composition comprising nanoparticles, wherein each of the nanoparticles comprises: (a) an albumin-bound paclitaxel core and (b) a binding agent that binds PD-L1, PD-L2 or PD-1 arranged on a surface of the albumin-bound paclitaxel core such that the binding portion of the binding agent is directed outward from that surface, wherein the binding agents retain their association with the surface of the nanoparticle upon reconstitution with an aqueous solution, and said lyophilized composition is stable at about 20° C. to about 25° C. for at least 3 months and the reconstituted nanoparticles are capable of binding to PD-L1, PD-L2 or PD-1 in vivo.

In one embodiment, the average reconstituted nanoparticle size is not substantially different from the particle size of the freshly prepared nanoparticles. In some embodiments, the average particle sizes are between 90 nm and 800 nm, including 90, 100, 110, 130, 150, 160, 200, 300, 400, 500, 600, 700 or 800 nm. In other embodiments, the average particles are larger, e.g. from greater than 800 nm to about 3.5 μm. In some embodiments, the particles are multimers of nanoparticles. In some embodiments the nanoparticles have average particle sizes of about 90 nm to about 225 nm either freshly made or after lyophilization and resuspension in an aqueous solution suitable for injection.

In some embodiments, the weight ratio of albumin-bound paclitaxel to binding agents is between about 5:1 to about 1:1. In other embodiments, the weight ratio of albumin-bound paclitaxel to binding agent is about 10:4. In further embodiments, the weight ratio of albumin-bound paclitaxel to binding agent is from greater than 1:1 to about 1:3.

In some embodiments, the core is albumin-bound paclitaxel (e.g., ABRAXANE®), and the binding agents are selected from binding agents that selectively recognize PD-L1 or PD-L2. In some embodiments, the core is albumin-bound paclitaxel (e.g., ABRAXANE®), and the binding agents selectively recognize PD-1. In some embodiments, the core is albumin-bound paclitaxel (e.g., ABRAXANE®), and the binding agents selectively recognize CTLA-4.

In some embodiments, the at least one therapeutic agent is located inside the nanoparticle. In other embodiments, the at least one therapeutic agent is located on the outside surface of the nanoparticle. In yet other embodiments, the at least one therapeutic agent is located inside the nanoparticle and on the outside surface of the nanoparticle.

In some embodiments, the nanoparticle contains more than one type of therapeutic agent. For example, a taxane and a platinum drug, e.g. paclitaxel and cisplatin.

In some embodiments, the binding agents comprise atezolizumab, nivolumab, pembrolizumab, avelumab or durvalumab, pidilizumab, BMS 936559, or biosimilars thereof. In some embodiments, the binding agents are a substantially single layer of binding agents on all or part of the surface of the nanoparticle.

In further embodiments, the antibodies are less glycosylated than normally found in natural human antibodies. Such glycosylation can be influenced by e.g. the expression system, or the presence of glycosylation inhibitors during expression. In some embodiments, the glycosylation status of an antibody or other binding agent is altered through enzymatic or chemical action.

In some embodiments, the at least one therapeutic agent is selected from abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, and cyclophosphamide.

In some embodiments, the binding agents, carrier protein and, when present, therapeutic agent, are bound through non-covalent bonds.

In some embodiments, the carrier protein is selected from gelatin, elastin, gliadin, legumin, zein, a soy protein, a milk protein, and a whey protein. In other embodiments, the carrier protein is albumin, for example, human serum albumin. In some embodiments, the carrier protein is a recombinant protein, e.g., recombinant human serum albumin.

In some embodiments, the nanoparticle composition is formulated for intravenous delivery. In other embodiments, the nanoparticle composition is formulated for direct injection or perfusion into a tumor.

In some embodiments, the second binding agent of the immunotherapy is formulated for intravenous delivery. In other embodiments, the second binding agent of the immunotherapy is formulated for direct injection or perfusion into a tumor.

In some embodiments, the average nanoparticle size in the nanoparticle composition is from greater than 800 nm to about 3.5 μm.

In some embodiments, the nanoparticles have a dissociation constant between about $1\times10^{-11}$M and about $1\times10^{-9}$M.

In another aspect, provided herein are methods of making nanoparticle compositions, wherein said methods comprise contacting the carrier protein and the optionally at least one therapeutic agent with the antibodies in a solution having a pH of between 5.0 and 7.5 and a temperature between about 5° C. and about 60° C., between about 23° C. and about 60° C., or between about 55° C. and about 60° C. under conditions and ratios of components that will allow for formation of the desired nanoparticles. In one embodiment, the nanoparticle is made at 55-60° C. and pH 7.0. In another aspect, provided herein are methods of making the nanoparticle compositions, wherein said method comprises (a) contacting the carrier protein and optionally the at least one therapeutic agent to form a core and (b) contacting the core with the antibodies in a solution having a pH of about 5.0 to about 7.5 at a temperature between about 5° C. and about 60° C., between about 23° C. and about 60° C., or between about 55° C. and about 60° C. under conditions and ratios of components that will allow for formation of the desired nanoparticles.

The amount of components (e.g., carrier protein, antibodies, therapeutic agents, combinations thereof) is controlled in order to provide for formation of the desired nanoparticles. A composition wherein the amount of components is too dilute will not form the nanoparticles as described herein. In a preferred embodiment, weight ratio of carrier protein to binding agent is 10:4. In some embodiments, the amount of carrier protein is between about 1 mg/mL and about 100 mg/mL. In some embodiments, the amount of binding agent is between about 1 mg/mL and about 30 mg/mL. For example, in some embodiments, the ratio of carrier protein:binding agent:solution is approximately 9 mg of carrier protein (e.g., albumin) to 4 mg of binding agent in 1 mL of solution (e.g., saline). An amount of therapeutic agent (e.g., paclitaxel) can also be added to the carrier protein.

The nanoparticles as described herein are pre-formed, meaning that the carrier protein (e.g., albumin), therapeutic agent (e.g., paclitaxel) and binding agents (e.g., antibodies) are mixed in vitro under conditions that allow formation of the nanoparticles, prior to administration to the patient (and/or prior to lyophilization of the nanoparticles). In some embodiments, the pre-formed nanoparticles are diluted in an aqueous solution prior to administration to the patient. By way of non-limiting example, the pre-formed nanoparticles may be diluted for administration no more than 5, 10, 20, 30, 45 minutes, or 60 minutes, or 1, 2, 3, 4, 5, 6, 7, 8, 9, 10, 12, or 24 hours prior to administration to the patient.

In further embodiments, the nanoparticles are made as above, and then lyophilized.

In another aspect, provided herein are methods for treating a cancer cell, the method comprising contacting the cell with an effective amount of a nanoparticle composition and an immunotherapy disclosed herein to treat the cancer cell.

In another aspect, provided herein are methods for treating a tumor in a patient in need thereof, the method comprising contacting the tumor with an effective amount of a nanoparticle composition and an immunotherapy disclosed herein to treat the tumor. In some embodiments, the size of the tumor is reduced.

Generally, the immunotherapy (PD-1 immunotherapy and/or CTLA-4 immunotherapy) is administered in a manner consistent with standard clinical protocols, e.g., consistent with an FDA- (or other regulatory body) approved label.

In some embodiments, the methods provided herein include the steps of: a) administering the nanoparticle composition and immunotherapy once a week for three weeks; b) ceasing administration of the nanoparticle composition and immunotherapy for one week; and c) repeating steps a) and b) as necessary to treat the cancer or tumor.

In related embodiments, the treatment comprises administration of the nanoparticle composition prior to administration of the immunotherapy. In one embodiment, the nanoparticle composition is administered between about 6 and 48, or 12 and 48 hours prior to administration of the immunotherapy. In another embodiment, the nanoparticle composition is administered between 6 and 12 hours prior to administration of the immunotherapy. In yet another embodiment, the nanoparticle composition is administered between 2 and 8 hours prior to administration of the immunotherapy. In still other embodiments, the nanoparticle composition is administered a week prior to administration of the immunotherapy.

In related embodiments, the treatment comprises administration of the immunotherapy prior to administration of the nanoparticle composition. In one embodiment, the immunotherapy is administered between about 6 and 48, or 12 and 48 hours prior to administration of the nanoparticle composition. In another embodiment, the immunotherapy is administered between 6 and 12 hours prior to administration of the nanoparticle composition. In yet another embodiment, the immunotherapy is administered between 2 and 8 hours prior to administration of the nanoparticle composition. In still other embodiments, the immunotherapy is administered a week prior to administration of the nanoparticle composition.

In some embodiments, the therapeutically effective amount of the nanoparticle composition comprises about 75 mg/m$^2$ to about 175 mg/m$^2$ of the carrier protein (i.e., milligrams carrier protein per m$^2$ of the patient). In other embodiments, the therapeutically effective amount comprises about 75 mg/m$^2$ to about 175 mg/m$^2$ of therapeutic agent (e.g., paclitaxel). In other embodiments, the therapeutically effective amount comprises about 30 mg/m$^2$ to about 70 mg/m$^2$ of the binding agent. In yet other embodiments, the therapeutically effective amount comprises about 30 mg/m$^2$ to about 70 mg/m$^2$ bevacizumab.

In one embodiment, the lyophilized composition comprises from about 75 mg/m$^2$ to about 175 mg/m$^2$ of the carrier protein which is preferably albumin; from about 30 mg/m$^2$ to about 70 mg/m$^2$ of the binding agent; and from about 75 mg/m$^2$ to about 175 mg/m$^2$ of paclitaxel.

In some embodiments, the present invention relates to a kit comprising: (a) an amount of the nanoparticle composition as described herein, (b) an amount of an immunotherapy agent capable of binding to PD-1, and optionally (c) instructions for use.

BRIEF DESCRIPTION OF THE DRAWINGS

The following figures are representative only of the invention and are not intended as a limitation. For the sake of consistency, nanoparticles using ABRAXANE® and rituximab employ the acronym "AR" and the number after AR such as AR160 is meant to confer the average particle size of these nanoparticles (in nanometers, based on Mastersizer 2000 analysis). Likewise, when the binding agent is atezolizumab, the acronym is "AA" and the number thereafter is the average particle size of the nanoparticles (in nanometers, based on Malvern Nanosight analysis).

FIGS. 1A-1F depicts the results of an experiment in which CD20 positive Daudi lymphoma cells were labeled with fluorescent tagged anti-human CD20 or isotype matched control in panels F and A, respectively, and analyzed by flow cytometry. In the other panels, the Daudi cells were pretreated with ABRAXANE® (ABX; FIG. 1B), ABX/rituximab nanoparticles (AR160; FIG. 1C), lyophilized and resuspended AR160 (AR160L; FIG. 1D), or Rituxan (FIG. 1E) prior to CD20 labeling. CD20 binding was specifically blocked by the AR160 nanoparticles and Rituxan, but not ABX alone, indicating that AR160 and AR160L binds CD20 on these cells and block binding of the fluorescent anti-CD20 antibody.

FIG. 3A) and ABX/trastuzumab nanoparticles (AT; FIG. 3B), both freshly made and lyophilized/resuspended.

FIG. 5A depicts the fluorescence accumulation in regions of interest (ROI) in each tumor (ROI 2, 3, and 4) and in background areas (ROI 1, 5, and 6). ROI 1, 5 and 6 serve as background references. FIG. 5B is a bar graph of the average fluorescence per unit of tumor area of mice in all three treatment groups and shows gross tumor delivery. FIG. 5C is a bar graph of the average fluorescence per unit of tumor area, normalized by background ROI, to give proportion of drug delivered to tumor versus body. The data demonstrate that administration of AR160 nanoparticles results in an increased fluorescence as compared to ABRAXANE® alone or ABRAXANE® coated with non-specific antibodies.

FIG. 11B), ABX alone (45 mg/kg; FIG. 11C) and AA130 (18 mg/kg atezolizumab and 45 mg/kg ABX; FIG. 11D) one time. Tumor growth was monitored 3 times per week. Tumor size was calculated with the equation: (length× width$^2$)/2.

DETAILED DESCRIPTION

Figure 2:
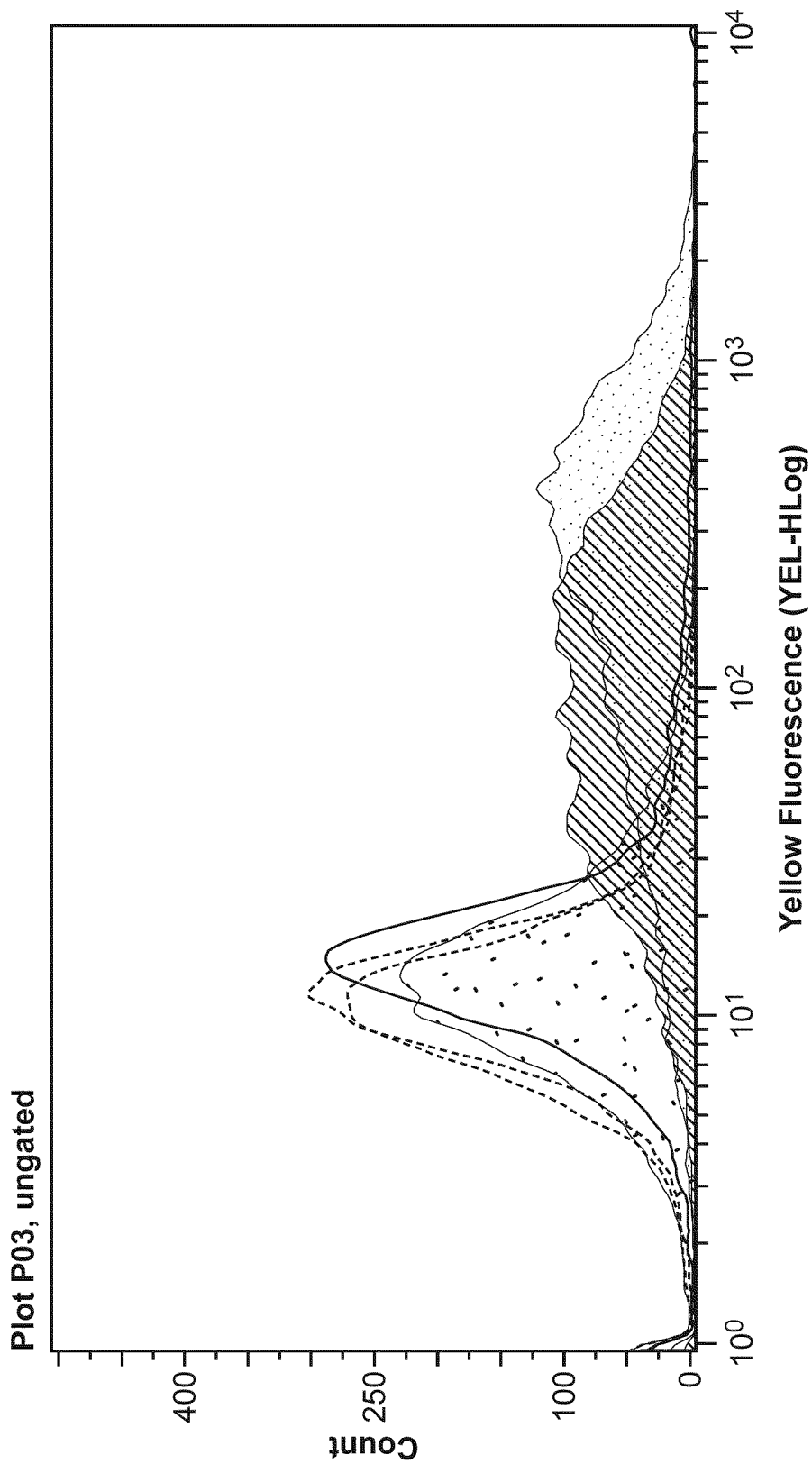
FIG. 2 is a histogram overlay of the scatterplots of FIG. 1.

After reading this description it will become apparent to one skilled in the art how to implement the invention in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

Definitions

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%. For example, "about 400 to about 800 binding agents" indicates that an outside surface of a nanoparticles contain an amount of binding agent between 360 and 880 particles.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps.

Embodiments defined by each of these transition terms are within the scope of this invention.

The term "nanoparticle" or "nanoparticle complex" as used herein refers to particles having at least one dimension which is less than 5 microns. In preferred embodiments, such as for intravenous administration, the nanoparticle has at least one dimension which is less than 1 micron. For direct administration, the nanoparticle is larger. Even larger particles are expressly contemplated by the invention.

In a population of particles, the sizes of individual particles are distributed about a mean. Particle sizes for the population can therefore be represented by an average, and also by percentiles. D50 is the particle size below which 50% of the particles fall. 10% of particles are smaller than the D IO value and 90% of particles are smaller than D90. Where unclear, the "average" size is equivalent to D50. So, for example, AB160 and AR160 refer to nanoparticles having an average size of 160 nanometers.

The term "nanoparticle" may also encompass discrete multimers of smaller unit nanoparticles. For example, a 320 nm particle comprises a dimer of a unit 160 nm nanoparticle. For 160 nm nanoparticles, multimers would therefore be approximately 320 nm, 480 nm, 640 nm, 800 nm, 960 nm, 1120 nm, and so on.

The term "carrier protein" as used herein refers to proteins that function to transport binding agents and/or therapeutic agents. The binding agents of the present disclosure can reversibly bind to the carrier proteins. Examples of carrier proteins are discussed in more detail below.

The term "core" as used herein refers to central or inner portion of the nanoparticle which may be comprised of a carrier protein, a carrier protein and a therapeutic agent, or other agents or combination of agents. In some embodiments, a portion of the binding agent may be associated with (e.g., non-covalently bound to) the core.

The term "therapeutic agent" as used herein means an agent which is therapeutically useful, e.g., an agent for the treatment, remission or attenuation of a disease state, physiological condition, symptoms, or etiological factors, or for the evaluation or diagnosis thereof. A therapeutic agent may be a chemotherapeutic agent, for example, mitotic inhibitors, topoisomerase inhibitors, steroids, anti-tumor antibiotics, antimetabolites, alkylating agents, enzymes, proteasome inhibitors, or any combination thereof.

As used herein, the term, "binding agent", "binding agent specific for," or "binding agent that specifically binds" refers to an agent that binds to a target antigen and does not significantly bind to unrelated compounds. Examples of binding agents that can be effectively employed in the disclosed methods include, but are not limited to, lectins, proteins, and antibodies, such as monoclonal antibodies, e.g. humanized monoclonal antibodies, chimeric antibodies, or polyclonal antibodies, or antigen-binding fragments thereof, as well as aptamers, fusion proteins, and aptamers. In an embodiment the binding agent is an exogenous antibody. An exogenous antibody is an antibody not naturally produced in a particular mammal, e.g. in a human, by the mammalian immune system.

The term "antibody" or "antibodies" as used herein refers to immunoglobulin molecules and immunologically active portions of immunoglobulin molecules (i.e., molecules that contain an antigen binding site that immuno-specifically bind an antigen). The term also refers to antibodies comprised of two immunoglobulin heavy chains and two immunoglobulin light chains as well as a variety of forms including full length antibodies and portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., *Eur. J Immunol.* 17, 105 (1987)) and single chains (e.g., Huston et al., *Proc. Natl. Acad. Sci. US.A.,* 85, 5879-5883 (1988) and Bird et al., *Science* 242, 423-426 (1988), which are incorporated herein by reference). (See, generally, Hood et al., *Immunology,* Benjamin, N.Y., 2ND ed. (1984); Harlow and Lane, *Antibodies. A Laboratory Manual*, Cold Spring Harbor Laboratory (1988); Hunkapiller and Hood, *Nature,* 323, 15-16 (1986), which are incorporated herein by reference). The antibody may be of any type (e.g., IgG, IgA, IgM, IgE or IgD). Preferably, the antibody is IgG. An antibody may be non-human (e.g., from mouse, goat, or any other animal), fully human, humanized, or chimeric. Antibody or antibodies include any biosimilar(s) of the antibodies disclosed herein. Biosimilars, as used herein, refers to a biopharmaceutical which is deemed to be comparable in quality, safety, and efficacy to a reference product marketed by an innovator company (Section 351(i) of the Public Health Service Act (42 U.S.C. 262(i)).

The term "dissociation constant," also referred to as "$K_d$," refers to a quantity expressing the extent to which a particular substance separates into individual components (e.g., the protein carrier, antibody, and optional therapeutic agent).

The terms "lyophilized," "lyophilization" and the like as used herein refer to a process by which the material (e.g., nanoparticles) to be dried is first frozen and then the ice or frozen solvent is removed by sublimation in a vacuum environment. An excipient is optionally included in pre-lyophilized formulations to enhance stability of the lyophilized product upon storage. In some embodiments, the nanoparticles can be formed from lyophilized components (carrier protein, antibody and optional therapeutic) prior to use as a therapeutic. In other embodiments, the carrier protein, binding agent, e.g., antibody, and optional therapeutic agent are first combined into nanoparticles and then lyophilized. The lyophilized sample may further contain additional excipients.

The term "bulking agents" comprise agents that provide the structure of the freeze-dried product. Common examples used for bulking agents include mannitol, glycine, lactose and sucrose. In addition to providing a pharmaceutically elegant cake, bulking agents may also impart useful qualities in regard to modifying the collapse temperature, providing freeze-thaw protection, and enhancing the protein stability over long-term storage. These agents can also serve as tonicity modifiers. In some embodiments, the lyophilized compositions described herein comprise bulking agents. In some embodiments, the lyophilized compositions described herein do not comprise bulking agents.

The term "buffer" encompasses those agents which maintain the solution pH in an acceptable range prior to lyophilization and may include succinate (sodium or potassium), histidine, phosphate (sodium or potassium), Tris(tris (hydroxymethyl)aminomethane), diethanolamine, citrate (sodium) and the like. The buffer of this invention has a pH in the range from about 5.5 to about 6.5; and preferably has a pH of about 6.0. Examples of buffers that will control the pH in this range include succinate (such as sodium succinate), gluconate, histidine, citrate and other organic acid buffers.

The term "cryoprotectants" generally includes agents which provide stability to the protein against freezing-induced stresses, presumably by being preferentially excluded from the protein surface. They may also offer protection during primary and secondary drying, and long-term product storage. Examples are polymers such as dextran and polyethylene glycol; sugars such as sucrose, glucose, trehalose, and lactose; surfactants such as polysorbates; and amino acids such as glycine, arginine, and serine.

The term "lyoprotectant" includes agents that provide stability to the protein during the drying or 'dehydration' process (primary and secondary drying cycles), presumably by providing an amorphous glassy matrix and by binding with the protein through hydrogen bonding, replacing the water molecules that are removed during the drying process. This helps to maintain the protein conformation, minimize protein degradation during the lyophilization cycle and improve the long-term products. Examples include polyols or sugars such as sucrose and trehalose.

The term "pharmaceutical formulation" refers to preparations which are in such form as to permit the active ingredients to be effective, and which contains no additional components that are toxic to the subjects to which the formulation would be administered.

"Pharmaceutically acceptable" excipients (vehicles, additives) are those which can reasonably be administered to a subject mammal to provide an effective dose of the active ingredient employed.

"Reconstitution time" is the time that is required to rehydrate a lyophilized formulation into a solution.

A "stable" formulation is one in which the protein therein essentially retains its physical stability and/or chemical stability and/or biological activity upon storage. For example, various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period.

The term "epitope" as used herein refers to the portion of an antigen which is recognized by a binding agent, e.g., an antibody. Epitopes include, but are not limited to, a short amino acid sequence or peptide (optionally glycosylated or otherwise modified) enabling a specific interaction with a protein (e.g., an antibody) or ligand. For example, an epitope may be a part of a molecule to which the antigen-binding site of a binding agent attaches.

The term "treating" or "treatment" covers the treatment of a disease or disorder (e.g., cancer), in a subject, such as a human, and includes: (i) inhibiting a disease or disorder, i.e., arresting its development; (ii) relieving a disease or disorder, i.e., causing regression of the disease or disorder; (iii) slowing progression of the disease or disorder; and/or (iv) inhibiting, relieving, or slowing progression of one or more symptoms of the disease or disorder. In some embodiments "treating" or "treatment" refers to the killing of cancer cells.

The term "kill" with respect to a cancer treatment is directed to include any type of manipulation that will lead to the death of that cancer cell or at least of portion of a population of cancer cells.

The term "aptamer" refers to a nucleic acid molecule that is capable of binding to a target molecule, such as a polypeptide. For example, an aptamer of the invention can specifically bind to PD-L1, PD-L2, PD-1, or CTLA-4. The generation of antibodies with a particular binding specificity and the therapeutic use of aptamers are well established in the art. See, e.g., U.S. Pat. Nos. 5,475,096, 5,270,163, 5,582,981, 5,840,867, 6,011,020, 6,051,698, 6,147,204, 6,180,348 and 6,699,843, and the therapeutic efficacy of Macugen® (Eyetech, N.Y.) for treating age-related macular degeneration, each of which is incorporated herein by reference in its entirety.

The term "oligomer" or "oligomeric" or "oligomerized" as used herein refers to oligomers composed of two or more monomers.

Fusion proteins are bioengineered polypeptides that join one peptide (e.g., the crystallizable fragment (Fc) domain of an antibody) with another biologically active agent, e.g., a protein domain, peptide, or nucleic acid or peptide aptamer, to generate a molecule with desired structure-function properties and significant therapeutic potential. The gamma immunoglobulin (IgG) isotype is often used as the basis for generating Fc-fusion proteins because of favorable characteristics such as recruitment of effector function and increased plasma half-life. Given the range of aptamers, both peptide and nucleic acids, that can be used as fusion partners, fusion proteins have numerous biological and pharmaceutical applications.

The term "sequentially," as used herein, refers to the administration of two or more treatments one after another in any order. In some embodiments, the treatments are administered within more than 48 hours of each other. In some embodiments, the treatments are administered within about 48 hours of each other, within about 36 hours of each other, within about 24 hours of each other, within about 12 hours of each other, within about 10 hours of each other, within about 8 hours of each other, within about 6 hours of each other, within about 4 hours of each other, within about two hours of each other, or within about 1 hour of each other.

The term "concurrently," as used herein, refers two or more treatments administered at substantially about the same time in any order.

The term "PD-1," as used herein, refers to programmed cell death protein-1, also known as CD279, which is expressed on the surface of activated T cells, B cells, as well as myeloid cells.

The term "PD-L1", as used herein, refers to programmed death-ligand 1, also known as B7-H1 or CD274, is a PD-1 ligand which is commonly expressed on the surface of dendritic cells or macrophages.

The term "PD-L2," as used herein, refers to programmed death ligand-2, also known as B7-DC or CD273, is a PD-1 ligand which is commonly expressed on the surface of dendritic cells or macrophages.

The terms "biosimilar" or "biosimilar," also known as "follow-on biologic" or "subsequent entry biologic", as used herein, refers to a biologic product which is substantially an identical copy of a product approved by a regulatory agency.

The terms "synergistic" or "synergistic effect" or "synergistically effective amount" or "synergistic efficacy", as used herein, refer to a greater-than-additive therapeutic effect which is produced by the administration of at least two agents, and which exceeds that which would otherwise result from administration of one of the agents without the administration of the other agent. For example, the therapeutic effect of the nanoparticle composition is increased when administered sequentially or concurrently with a binding agent to provide a synergistic effect, provided that the increase is greater than the additive effectiveness of the binding agent and the nanoparticle composition when administered alone. The term "synergistically therapeutic amount" typically refers to a less than standard therapeutic amount of one or both therapeutic agents, meaning that the amount required for the desired therapeutic effectiveness is lower than when the therapeutic agent is used alone. A synergistically therapeutic amount also includes when one therapeutic agent is given at a standard therapeutic dose and another therapeutic agent is administered in a less than standard therapeutic dose The term "therapeutically effective amount" or "therapeutic effectiveness," as used herein, of a nanoparticle composition or binding agent refers to nanoparticle composition or binding agent levels in which the physiological effects of a disease or disorder are, at a minimum, ameliorated. A therapeutically effective amount can be given in one or more administrations using one or more tablets, capsules or other pharmaceutical units. The amount of a nanoparticle composition or binding agent which constitutes a therapeutically effective amount will vary depending on the nanoparticle composition or binding agent, the disorder and its severity, and the general health, age, sex, body weight and tolerance to drugs of the subject to be treated, but can be determined routinely by one of ordinary skill in the art. In some embodiments, the term "therapeutically effective amount" refers to a synergistically effective amount or synergistically therapeutic amount.

Additionally, some terms used in this specification are more specifically defined below.

Overview

The current invention is predicated, in part, on the surprising discovery that optionally lyophilized nanoparticles comprising a carrier protein, a binding agent, e.g., an antibody, an aptamer, or a fusion protein, having a PD-L1 or PD-L2 binding domain, and a therapeutic agent provide targeted therapy to a tumor while minimizing toxicity to the patient. The nanoparticles as described herein are thus a significant improvement versus conventional ADCs.

The invention is further predicated, in part, on the synergy of immune checkpoint inhibitor immunotherapy (e.g., PD-1 immunotherapy and/or CTLA-4 immunotherapy) with the nanoparticles. Without being bound by theory, it is contemplated that binding of PD-L1 or PD-L2 by the binding agents (e.g., antibodies) as described herein will deplete or diminish the amount of PD-L1 or PD-L2 available to bind PD-1 on T cells, thereby increasing the therapeutic effectiveness of PD-1-based immunotherapy. Administration of the nanoparticles, alone or in combination with PD-1 immunotherapy, may increase the number of T cells that are free from PD-1 pathway-mediated inhibition, and restore the patient's immune response against a PD-L1- or PD-L2-expressing cancer.

For conventional ADCs to be effective, it is critical that the linker be stable enough not to dissociate in the systemic circulation but allow for sufficient drug release at the tumor site. Alley, S. C., et al. (2008) *Bioconjug Chem* 19:759-765. This has proven to be a major hurdle in developing effective drug conjugate (Julien, D. C., et al. (2011) *MAbs* 3:467-478; Alley, S. C., et al. (2008) *Bioconjug Chem* 19:759-765); therefore, an attractive feature of the nanoparticles described herein is that a biochemical linker is not required.

Another shortcoming of current ADCs is that higher drug penetration into the tumor has not been substantively proven in human tumors. Early testing of ADCs in mouse models suggested that tumor targeting with antibodies would result in a higher concentration of the active agent in the tumor (Deguchi, T. et al. (1986) *Cancer Res* 46: 3751-3755); however, this has not correlated in the treatment of human disease, likely because human tumors are much more heterogeneous in permeability than mouse tumors. Jain, R. K. et al. (2010) *Nat Rev Clin Oncol* 7:653-664. Also, the size of the nanoparticle is critical for extravasation from the vasculature into the tumor. In a mouse study using a human colon adenocarcinoma xenotransplant model, the vascular pores were permeable to liposomes up to 400 nm. Yuan, F., et al. (1995) *Cancer Res* 55: 3752-3756. Another study of tumor pore size and permeability demonstrated that both characteristics were dependent on tumor location and growth status, with regressing tumors and cranial tumors permeable to particles less than 200 nm. Hobbs, S. K., et al. (1998) *Proc Natl Acad Sci USA* 95:4607-4612. The nano-immune conjugate (nanoparticles) described herein overcomes this issue by the fact that the large complex, which is less than 200 nm intact, is partially dissociated in systemic circulation into smaller functional units that are easily able to permeate tumor tissue. Furthermore, once the conjugate arrives to the tumor site, the smaller toxic payload can be released and only the toxic portion needs to be taken up by tumor cells, not the entire conjugate.

The advent of antibody- (i.e. AVASTIN®) coated albumin nanoparticles containing a therapeutic agent (i.e., ABRAXANE®) has led to a new paradigm of directional delivery of two or more therapeutic agents to a predetermined site in vivo. See PCT Patent Publication Nos. WO 2012/154861 and WO 2014/055415, each of which is incorporated herein by reference in its entirety.

When compositions of albumin and a binding agent, e.g., antibody, are admixed together in an aqueous solution at specific concentrations and ratios, the binding agents useful in this invention spontaneously self-assemble into and onto the albumin to form nanoparticles having multiple copies of the binding agent (up to 500 or more). Without being limited to any theory, it is contemplated that binding agents (e.g., antibodies) non-covalently bind to the carrier protein (e.g., albumin) via one or more albumin-binding motifs of the binding agent, and one or more antibody-binding motifs on the carrier protein. Examples of such motifs can be found in PCT Application No. PCT/US17/45643, which is incorporated herein by reference in its entirety.

While protein compositions comprising a single source protein are commonly stored in lyophilized form where they exhibit significant shelf-life, such lyophilized compositions generally do not contain a self-assembled nanoparticle of two different proteins integrated together by hydrophobic-hydrophobic interactions. Moreover, the nanoparticle configuration wherein a majority of the binding portions of the binding agent are exposed on the surface of the nanoparticles lends itself to being susceptible to dislodgement or reconfiguration by conditions which otherwise would be considered benign. For example, during lyophilization, ionic charges on the proteins are dehydrated thereby exposing the underlying charges. Exposed charges allow for charge-charge interactions between the two proteins which can alter the binding affinity of each protein to the other. In addition, the concentration of the nanoparticles increases significantly as the solvent (e.g., water) is removed. Such increased concentrations of nanoparticles could lead to irreversible oligomerization. Oligomerization is a known property of proteins that reduces the biological properties of the oligomer as compared to the monomeric form and increases the size of the particle, sometimes beyond 1 micron.

On the other hand, a stable form of a nanoparticle composition is required for clinical and/or commercial use, where a shelf-life of at least 3 months is required and shelf-lives of greater than 6 months or 9 months are preferred. Such a stable composition must be readily available for intravenous injection, must retain its self-assembled form upon intravenous injection so as to direct the nanoparticle to the predetermined site in vivo, must have a maximum size of less than 1 micron so as to avoid any ischemic event when delivered into the blood stream, and finally must be compatible with the aqueous composition used for injection.

In some aspects, the first binding agent and/or the second binding agent is a fusion protein. In one embodiment, the fusion protein is AMP-224 (PD-L2 IgG2a fusion protein; Amplimmune/GlaxoSmith Klein); AMP-514 (MEDI0680) (PD-L2 fusion protein; Amplimmune/GlaxoSmith Klein), or a biosimilar thereof. AMP-224 and AMP-514 target PD-1.

In some embodiments, the antibodies are a substantially single layer of antibodies on all or part of the surface of the nanoparticle.

Table 1 depicts a list of non-limiting list of antibodies.

TABLE 1

Example Antibodies

| Generic Name | Brand Name | Type | Example of Possible Indication |
| --- | --- | --- | --- |
| Avelumab (MSB0010718C) | BAVENCIO ® | anti-PD-L1; human IgG1 mAb | Solid tumor, gastric cancer, Merkel cell carcinoma, non-small cell lung cancer |
| Durvalumab (MEDI4736) | IMFINZI ™ | anti-PD-L1; human IgG1κ mAb | NSCLC, head and neck, bladder, gastric, pancreatic, HCC and blood cancers |
| Pidilizumab (CT-011) | | anti-Delta-like 1 (secondary binding to some forms of PD-1); humanized IgG1 mAb | Lymphoma, myeloma, diffuse intrinsic pontine glioma |
| BMS 936559/ MDX-1105 | | anti-PD-L1 mAb | melanoma, non-small cell lung cancer |
| Nivolumab (BMS-936558) | OPDIVO ® | Anti-PD-1; human IgG4 mAb | metastatic melanoma; squamous non-small cell lung cancer; renal cell carcinoma |
| atezolizumab (RG7446; MPDL3280A) | TECENTRIQ ® | anti-PD-L1 mAb | bladder cancer, NSCLC, melanoma, breast, renal cell carcinoma, lymphoma |
| Ipilimumab | YERVOY ® | Anti-CTLA-4; Human IgG1 mAb | Melanoma |
| Pembrolizumab | KEYTRUDA ® | Anti-PD-1; Human IgG4 mAb | Melanoma |

Compounds

As will be apparent to the skilled artisan upon reading this disclosure, the present disclosure relates to compositions of nanoparticles containing a carrier protein, binding agents, and optionally at least one therapeutic agent, wherein said compositions are optionally lyophilized.

In some embodiments, the carrier protein can be albumin, gelatin, elastin (including topoelastin) or elastin-derived polypeptides (e.g., α-elastin and elastin-like polypeptides (ELPs)), gliadin, legumin, zein, soy protein (e.g., soy protein isolate (SPI)), milk protein (e.g., β-lactoglobulin (BLG) and casein), or whey protein (e.g., whey protein concentrates (WPC) and whey protein isolates (WPI)). In preferred embodiments, the carrier protein is albumin. In preferred embodiments, the albumin is egg white (ovalbumin), bovine serum albumin (BSA), or the like. In even more preferred embodiments, the carrier protein is human serum albumin (HSA). In some embodiments, the carrier protein is a recombinant protein, e.g. recombinant human serum albumin. In some embodiments, the carrier protein is a generally regarded as safe (GRAS) excipient approved by the United States Food and Drug Administration (FDA).

In some embodiments, the binding agents are antibodies.

In some embodiments, the anti-PD-1 antibody comprises nivolumab, pembrolizumab, pidilizumab, PDR001, or biosimilars thereof. In some aspects, the anti-PD-L1 antibody is atezolizumab, avelumab, durvalumab, or BMS 936559 (MDX1105). In some aspects, the binding agent of the CTLA-4 immunotherapy is an anti-CTLA-4 antibody. In one embodiment, the anti-CTLA-4 antibody is ipilimumab.

In some embodiments, the at least one therapeutic agent is selected from abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, and cyclophosphamide. Preferably, the therapeutic agent is paclitaxel. Additional therapeutic agents are known, for example those listed in PCT Publication No. WO2017/031368, which is incorporated herein by reference in its entirety.

It is to be understood that the therapeutic agent may be located inside the nanoparticle, on the outside surface of the nanoparticle, or both. The nanoparticle may contain more than one therapeutic agent, for example, two therapeutic agents, three therapeutic agents, four therapeutic agents, five therapeutic agents, or more. Furthermore, a nanoparticle may contain the same or different therapeutic agents inside and outside the nanoparticle.

In one aspect, the nanoparticle comprises at least 100 binding agents non-covalently bound to the surface of the nanoparticle. In one aspect, the nanoparticle comprises at least 200 binding agents non-covalently bound to the surface of the nanoparticle. In one aspect, the nanoparticle comprises at least 300 binding agents non-covalently bound to the surface of the nanoparticle. In one aspect, the nanoparticle comprises at least 400 binding agents non-covalently bound to the surface of the nanoparticle. In one aspect, the nanoparticle comprises at least 500 binding agents non-covalently bound to the surface of the nanoparticle. In one aspect, the nanoparticle comprises at least 600 binding agents non-covalently bound to the surface of the nanoparticle.

In one aspect, the nanoparticle comprises between about 100 and about 1000 binding agents non-covalently bound to the surface of the nanoparticle. In one aspect, the nanoparticle comprises between about 200 and about 1000 binding agents non-covalently bound to the surface of the nanoparticle. In one aspect, the nanoparticle comprises between about 300 and about 1000 binding agents non-covalently bound to the surface of the nanoparticle. In one aspect, the nanoparticle comprises between about 400 and about 1000 binding agents non-covalently bound to the surface of the nanoparticle. In one aspect, the nanoparticle comprises between about 500 and about 1000 binding agents non-covalently bound to the surface of the nanoparticle. In one aspect, the nanoparticle comprises between about 600 and about 1000 binding agents non-covalently bound to the surface of the nanoparticle. In one aspect, the nanoparticle comprises between about 200 and about 800 binding agents non-covalently bound to the surface of the nanoparticle. In one aspect, the nanoparticle comprises between about 300 and about 800 binding agents non-covalently bound to the surface of the nanoparticle. In preferred embodiments, the nanoparticle comprises between about 400 and about 800 binding agents non-covalently bound to the surface of the nanoparticle. Contemplated values include any value or subrange within any of the recited ranges, including endpoints.

In one aspect, the average particle size in the nanoparticle composition is less than about 1 μm. In one aspect, the average particle size in the nanoparticle composition is between about 90 nm and about 1 μm. In one aspect, the average particle size in the nanoparticle composition is between about 90 nm and about 900 nm. In one aspect, the average particle size in the nanoparticle composition is between about 90 nm and about 800 nm. In one aspect, the average particle size in the nanoparticle composition is between about 90 nm and about 700 nm. In one aspect, the average particle size in the nanoparticle composition is between about 90 nm and about 600 nm. In one aspect, the average particle size in the nanoparticle composition is between about 90 nm and about 500 nm. In one aspect, the average particle size in the nanoparticle composition is between about 90 nm and about 400 nm. In one aspect, the average particle size in the nanoparticle composition is between about 90 nm and about 300 nm. In one aspect, the average particle size in the nanoparticle composition is between about 90 nm and about 200 nm. In a preferred embodiment, the average particle size in the nanoparticle composition is between about 100 nm and about 180 nm. In an especially preferred embodiment, the mean particle size in the nanoparticle composition is about 130 nm or about 160 nm. Contemplated values include any value, subrange, or range within any of the recited ranges, including endpoints. In one embodiment, the nanoparticle size is determined using a Mastersizer 2000. In one embodiment, the nanoparticle size is determined using a Malvern Nanosight.

In one aspect, the nanoparticle composition is formulated for intravenous injection. In order to avoid an ischemic event, the nanoparticle composition formulated for intravenous injection should comprise nanoparticles with an average particle size of less than about 1 μm.

In one aspect, the average particle size in the nanoparticle composition is greater than about 1 μm. In one aspect, the average particle size in the nanoparticle composition is between about 1 μm and about 5 μm. In one aspect, the average particle size in the nanoparticle composition is between about 1 μm and about 4 μm. In one aspect, the average particle size in the nanoparticle composition is between about 1 μm and about 3 μm. In one aspect, the average particle size in the nanoparticle composition is between about 1 μm and about 2 μm. In one aspect, the average particle size in the nanoparticle composition is between about 1 μm and about 1.5 μm. Contemplated values include any value, subrange, or range within any of the recited ranges, including endpoints.

In one aspect, the nanoparticle composition is formulated for direct injection into a tumor. Direct injection includes injection into or proximal to a tumor site, perfusion into a tumor, and the like. When formulated for direct injection into a tumor, the nanoparticle may comprise any average particle size. Without being bound by theory, it is believed that larger particles (e.g., greater than 500 nm, greater than 1 μm, and the like) are more likely to be immobilized within the tumor, thereby providing a beneficial effect. Larger particles can accumulate in the tumor or specific organs. See, e.g., 20-60 micron glass particle that is used to inject into the hepatic artery feeding a tumor of the liver, called "TheraSphere®" (in clinical use for liver cancer). Therefore, for intravenous administration, particles under 1 μm are typically used. Particles over 1 μm are, more typically, administered directly into a tumor ("direct injection") or into an artery feeding into the site of the tumor.

In one aspect, less than about 0.01% of the nanoparticles within the composition have a particle size greater than 200 nm, greater than 300 nm, greater than 400 nm, greater than 500 nm, greater than 600 nm, greater than 700 nm, or greater than 800 nm. In one aspect, less than about 0.001% of the nanoparticles within the composition have a particle size greater than 200 nm, greater than 300 nm, greater than 400 nm, greater than 500 nm, greater than 600 nm, greater than 700 nm, or greater than 800 nm. In a preferred embodiment, less than about 0.01% of the nanoparticles within the composition have a particle size greater than 800 nm. In a more preferred embodiment, less than about 0.001% of the nanoparticles within the composition have a particle size greater than 800 nm.

In a preferred aspect, the sizes and size ranges recited herein relate to particle sizes of the reconstituted lyophilized nanoparticle composition. That is, after the lyophilized nanoparticles are resuspended in an aqueous solution (e.g., water, other pharmaceutically acceptable excipient, buffer, etc.), the particle size or average particle size is within the range recited herein.

In one aspect, at least about 50%, 60%, 70%, 80%, 90%, 95%, 96%, 97%, 98%, 99%, 99.5%, or 99.9% of the nanoparticles are present in the reconstituted composition as single nanoparticles. That is, fewer than about 50%, 40%, 30%, etc. of the nanoparticles are dimerized or oligomerized.

In some embodiments, the nanoparticles in the composition have less than 20% by number dimerization, less than 10% by number dimerization and preferably less than 5% by number dimerization.

In some embodiments, the size of the nanoparticle can be controlled by the adjusting the amount (e.g., ratio) of carrier protein to binding agent. The size of the nanoparticles, and the size distribution, is also important. The nanoparticles of the invention may behave differently according to their size.

At large sizes, an agglomeration may block blood vessels. Therefore, agglomeration of nanoparticles can affect the performance and safety of the composition. On the other hand, larger particles may be more therapeutic under certain conditions (e.g., when not administered intravenously).

In one aspect, the nanoparticle composition comprises at least one additional therapeutic agent. In one embodiment, the at least one additional therapeutic agent is non-covalently bound to the outside surface of the nanoparticle. In one embodiment, the at least one additional therapeutic agent is arranged on the outside surface of the nanoparticle. In one embodiment, the at least one additional therapeutic agent is selected from abiraterone, bendamustine, bortezomib, carboplatin, cabazitaxel, cisplatin, chlorambucil, dasatinib, docetaxel, doxorubicin, epirubicin, erlotinib, etoposide, everolimus, gemcitabine, gefitinib, idarubicin, imatinib, hydroxyurea, imatinib, lapatinib, leuprorelin, melphalan, methotrexate, mitoxantrone, nedaplatin, nilotinib, oxaliplatin, pazopanib, pemetrexed, picoplatin, romidepsin, satraplatin, sorafenib, vemurafenib, sunitinib, teniposide, triplatin, vinblastine, vinorelbine, vincristine, and cyclophosphamide. In one embodiment, the at least one additional therapeutic agent is an anti-cancer binding agent, e.g., an anti-cancer antibody. Additional anti-cancer antibodies are known, for example those listed in PCT Publication No. WO2017/031368, which is incorporated herein by reference in its entirety.

Methods of Making Nanoparticles

In some aspects, the current invention relates to methods of making nanoparticle compositions as described herein.

In one aspect, the nanoparticles of the nanoparticle composition are formed by contacting the carrier protein or carrier protein-therapeutic agent particle with the binding agent at a ratio of about 10:1 to about 10:30 carrier protein particle or carrier protein-therapeutic agent particle to binding agent. In one embodiment, the ratio is about 10:2 to about 10:25. In one embodiment, the ratio is about 10:2 to about 1:1. In a preferred embodiment, the ratio is about 10:2 to about 10:6. In an especially preferred embodiment, the ratio is about 10:4. Contemplated ratios include any value, subrange, or range within any of the recited ranges, including endpoints.

In one embodiment, the amount of solution or other liquid medium employed to form the nanoparticles is particularly important. No nanoparticles are formed in an overly dilute solution of the carrier protein (or carrier protein-therapeutic agent) and the antibodies. An overly concentrated solution will result in unstructured aggregates. In some embodiments, the amount of solution (e.g., sterile water, saline, phosphate buffered saline) employed is between about 0.5 mL of solution to about 20 mL of solution. In some embodiments, the amount of carrier protein is between about 1 mg/mL and about 100 mg/mL. In some embodiments, the amount of binding agent is between about 1 mg/mL and about 30 mg/mL. For example, in some embodiments, the ratio of carrier protein:binding agent:solution is approximately 9 mg of carrier protein (e.g., albumin) to 4 mg of binding agent, e.g., antibody (e.g., BEV) in 1 mL of solution (e.g., saline). An amount of therapeutic agent (e.g., taxol) can also be added to the carrier protein. For example, 1 mg of taxol can be added 9 mg of carrier protein (10 mg carrier protein-therapeutic) and 4 mg of binding agent, e.g., antibody, Fc fusion molecule, or aptamer, in 1 mL of solution. When using a typical i.v. bag, for example, with the solution of approximately 1 liter one would need to use 1000× the amount of carrier protein/carrier protein-therapeutic agent and antibodies compared to that used in 1 mL. Thus, one cannot form the present nanoparticles in a standard i.v. bag. Furthermore, when the components are added to a standard i.v. bag in the therapeutic amounts of the present invention, the components do not self-assemble to form nanoparticles.

In one embodiment, the carrier protein or carrier protein-therapeutic agent particle is contacted with the binding agent in a solution having a pH between about 4 and about 8. In one embodiment, the carrier protein or carrier protein-therapeutic agent particle is contacted with the binding agent in a solution having a pH of about 4. In one embodiment, the carrier protein or carrier protein-therapeutic agent particle is contacted with the binding agent in a solution having a pH of about 5. In one embodiment, the carrier protein or carrier protein-therapeutic agent particle is contacted with the binding agent in a solution having a pH of about 6. In one embodiment, the carrier protein or carrier protein-therapeutic agent particle is contacted with the binding agent in a solution having a pH of about 7. In one embodiment, the carrier protein or carrier protein-therapeutic agent particle is contacted with the binding agent in a solution having a pH of about 8. In a preferred embodiment, the carrier protein or carrier protein-therapeutic agent particle is contacted with the binding agent in a solution having a pH between about 5 and about 7.

In one embodiment, the carrier protein particle or carrier protein-therapeutic agent particle is incubated with the binding agent at a temperature of about 5° C. to about 60° C., or any range, subrange, or value within that range including endpoints. In a preferred embodiment, the carrier protein particle or carrier protein-therapeutic agent particle is incubated with the binding agent at a temperature of about 23° C. to about 60° C.

Without being bound by theory, it is believed that the stability of the nanoparticles within the nanoparticle composition is, at least in part, dependent upon the temperature and/or pH at which the nanoparticles are formed, as well as the concentration of the components (i.e., carrier protein, binding agent, and optionally therapeutic agent) in the solution. In one embodiment, the $K_d$ of the nanoparticles is between about $1\times10^{-11}$M and about $2\times10^{-5}$M. In one embodiment, the $K_d$ of the nanoparticles is between about $1\times10^{-11}$ M and about $2\times10^{-8}$ M. In one embodiment, the $K_d$ of the nanoparticles is between about $1\times10^{-11}$ M and about $7\times10^{-9}$M. In a preferred embodiment, the $K_d$ of the nanoparticles is between about $1\times10^{-11}$M and about $3\times10^{-8}$M. Contemplated values include any value, subrange, or range within any of the recited ranges, including endpoints.

Lyophilization

Lyophilization, or freeze-drying, removes water from a composition. In the process, the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3(9) 26-30 (1990) and Arakawa et al., Pharm. Res. 8(3):285-291 (1991).

While proteins may be lyophilized, the process of lyophilization and reconstitution may affect the properties of the protein. Because proteins are larger and more complex than traditional organic and inorganic drugs (i.e. possessing multiple functional groups in addition to complex three-dimensional structures), the formulation of such proteins poses special problems. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (i.e. any process which involves modification of the protein by bond formation or cleavage resulting in a new chemical entity) or physical instability (i.e. changes in the higher order structure of the protein). Chemical instability can result from deamidation, racemization, hydrolysis, oxidation, beta elimination or disulfide exchange. Physical instability can result from denaturation, aggregation, precipitation or adsorption, for example. The three most common protein degradation pathways are protein aggregation, deamidation and oxidation. Cleland, et al., Critical Reviews in Therapeutic Drug Carrier Systems 10(4): 307-377 (1993).

The lyophilized compositions of this invention are prepared by standard lyophilization techniques with or without the presence of stabilizers, buffers, etc. Surprisingly, these conditions do not alter the relatively fragile structure of the nanoparticles. Moreover, at best, these nanoparticles retain their size distribution upon lyophilization and, more importantly, can be reconstituted for in vivo administration (e.g., intravenous delivery) in substantially the same form and ratios as if freshly made.

Formulations

In one aspect, the nanoparticle composition is formulated for systemic delivery, e.g., intravenous administration.

In one aspect, the nanoparticle composition is formulated for direct injection into a tumor. Direct injection includes injection into or proximal to a tumor site, perfusion into a tumor, and the like. Because the nanoparticle composition is not administered systemically, a nanoparticle composition is formulated for direct injection into a tumor may comprise any average particle size. Without being bound by theory, it is believed that larger particles (e.g., greater than 500 nm, greater than 1 µm, and the like) are more likely to be immobilized within the tumor, thereby providing what is believed to be a better beneficial effect.

In another aspect, provided herein is a composition comprising nanoparticles as provided herein, and at least one pharmaceutically acceptable excipient.

In general, the compositions provided herein can be formulated for administration to a patient by any of the accepted modes of administration. Various formulations and drug delivery systems are available in the art. See, e.g., Gennaro, A. R., ed. (1995) *Remington's Pharmaceutical Sciences*, 18th ed., Mack Publishing Co.

In general, nanoparticles as provided herein will be administered as pharmaceutical compositions by any one of the following routes: oral, systemic (e.g., transdermal, intranasal or by suppository), or parenteral (e.g., intramuscular, intravenous or subcutaneous) administration.

The compositions are comprised of, in general, a nanoparticle of the present invention in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18th ed., 1990).

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a nanoparticle of the invention formulated in a compatible pharmaceutical carrier may also be prepared, placed in an appropriate container, and labeled for treatment of an indicated condition.

Treatment Methods

The nanoparticle compositions as described herein are useful in treating cancer cells and/or tumors in a mammal having a cancer or tumor that expresses PD-L1 and/or PD-L2. In a preferred embodiment, the mammal is a human (i.e., a human patient). Preferably, the lyophilized nanoparticle composition is reconstituted (suspended in an aqueous excipient) prior to administration.

In one aspect is provided a method for treating a cancer cell, the method comprising contacting the cell with an effective amount of nanoparticles and an immunotherapy (e.g., PD-1 or CTLA-4) as described herein to treat the cancer cell. Treatment of a cancer cell includes, without limitation, reduction in proliferation, killing the cell, preventing metastasis of the cell, and the like.

"Immune therapy", "immune therapies", "immunotherapy" or "immunotherapies," as used herein, generally refer to treatments of a disease by inducing, enhancing, or suppressing an immune response. In some cases, immune therapies or immunotherapies can either elicit or activate or amplify immune responses (also known as "activation immunotherapies"), or reduce or suppress immune responses (also known as "suppression immunotherapies"). For example, cancer immune therapy or cancer immunotherapy attempts to stimulate or activate the immune responses against tumors or cancer cells. As would be understood by one skilled in the art, immune therapy or immunotherapy can utilize a variety of approaches or mechanisms including, but not limited to, antibodies, antigens, use and/or activation of immune responsive cells such as lymphocytes, macrophages, dendritic cells, other antigen presenting cells, natural killer cells (NK Cells; e.g., NK-92), T-cells (e.g., helper T-cells, cytotoxic T lymphocytes (CTL), etc.), therapies involving immune modulators (including, but not limited to: interleukins (e.g., IL-2, IL-7, IL-12, etc.), cytokines (e.g., interferons, G-CSF, imiquimod, etc.), chemokines (e.g., CCL3, CCL26, CXCL7, etc.), immunomodulatory imide drugs, etc.) and the like. Immune therapy or immunotherapy can be administered by the use of one type of antibody or multiple types of antibodies. Immune therapy or immunotherapy approaches can also be administered alone or in combination with other therapeutic agents or mechanisms, such as, for example, chemotherapy agents, and the like, in order to enhance immune responses against, for example, tumors.

In one aspect is provided a method for treating a tumor in a patient in need thereof, the method comprising administering to the patient a therapeutically effective amount of a nanoparticle composition and an immunotherapy as described herein to treat the tumor. In one embodiment, the size of the tumor is reduced. In one embodiment, the tumor size does not increase (i.e. progress) for at least a period of time during and/or after treatment.

In one embodiment, the nanoparticle composition is administered intravenously. In one embodiment, the nanoparticle composition is administered directly to the tumor. In one embodiment, the nanoparticle composition is administered by direct injection or perfusion into the tumor.

In one embodiment, the immunotherapy is administered intravenously. In one embodiment, the immunotherapy is administered directly to the tumor. In one embodiment, the immunotherapy is administered by direct injection or perfusion into the tumor.

In one aspect, a method for treating a patient suffering from a cancer which expresses PD-L1 or PD-L2 is provided, where the method comprises administering to the patient a nanoparticle composition comprising nanoparticles, wherein each of the nanoparticles comprise a carrier protein, binding agents having a PD-L1 or PD-L2 binding portion, and optionally at least one therapeutic agent, wherein the nanoparticles are capable of binding to PD-L1 or PD-L2. In some embodiments, the method further comprises administering a PD-1 immunotherapy to the patient. In one embodiment, the PD-1 immunotherapy comprises administering a second binding agent capable of binding to PD-1.

In another aspect, the present invention relates to a method for increasing the therapeutic effectiveness of an immunotherapy treatment of a patient suffering from a cancer which expresses PD-L1 or PD-L2, the method comprising administering to the patient a therapeutically effective amount of the nanoparticle composition described herein. In some embodiments, the method further comprises administering a PD-1 immunotherapy to the patient. In one embodiment, the PD-1 immunotherapy comprises administering a second binding agent capable of binding to PD-1.

In one embodiment, the method comprises:
 a) administering the nanoparticle composition once a week for three weeks;
 b) ceasing administration of the nanoparticle composition for one week; and
 c) optionally repeating steps a) and b) as necessary to treat the tumor.

In one aspect, the PD-1 immunotherapy is administered concurrently with the nanoparticle composition. In one aspect, the PD-1 immunotherapy is administered before the nanoparticle composition. In one aspect, the PD-1 immunotherapy is administered subsequent to the nanoparticle composition. In one aspect, the PD-1 immunotherapy is administered according to the regulatory entity (e.g., FDA)-approved label.

In some aspects, each of the nanoparticles of the nanoparticle composition comprises between about 400 to about 800 said binding agents.

In some aspects, the first binding agents (binding agents in the nanoparticles) are aptamers. In some aspects, the second binding agent of the PD-1 immunotherapy is an aptamer.

In some aspects, the first binding agents (binding agents in the nanoparticles) are antibodies. In some aspects, the second binding agent of the PD-1 immunotherapy is an antibody.

In some aspects, the anti-PD-1 antibody comprises nivolumab, pembrolizumab, pidilizumab, PDR001, or biosimilars thereof. In some aspects, the anti-PD-L1 antibody is atezolizumab, avelumab, durvalumab, or BMS 936559 (MDX1105), or biosimilar thereof. In some aspects, the binding agent of the CTLA-4 immunotherapy is an anti-CTLA-4 antibody. In one embodiment, the anti-CTLA-4 antibody is ipilimumab, or biosimilar thereof.

In some aspects, the first binding agent and/or the second binding agent is a fusion protein. In one embodiment, the fusion protein is AMP-224 (PD-L2 IgG2a fusion protein; Amplimmune/GlaxoSmith Klein); AMP-514 (MEDI0680) (PD-L2 fusion protein; Amplimmune/GlaxoSmith Klein), or a biosimilar thereof. In some aspects, the nanoparticle composition is lyophilized.

In some aspects, the second binding agent of the PD-1 immunotherapy is a free binding agent, wherein the free binding agent is not complexed with or otherwise integrated onto and/or into a nanoparticle composition.

In some aspects, PD-1 immunotherapy is an immunotherapy nanoparticle composition comprising the second binding agent complexed with or integrated onto and/or into a nanoparticle composition, wherein the immunotherapy nanoparticle composition comprises a carrier protein and said second binding agent. In some aspects, the immunotherapy nanoparticle composition is lyophilized.

In some aspects, the second binding agent of the immunotherapy nanoparticle composition is an antibody. In some aspects, the second binding agent of the immunotherapy nanoparticle composition is an anti-PD-1 antibody. In some aspects, the anti-PD-1 antibody comprises nivolumab, pembrolizumab, pidilizumab, PDR001, or biosimilars thereof.

In some aspects, the second binding agent of the immunotherapy nanoparticle composition is an aptamer. In some aspects, the second binding agent of the immunotherapy nanoparticle composition is a PD-1 aptamer.

In some aspects, the second binding agent of the immunotherapy nanoparticle composition is a fusion protein. some aspects, the second binding agent of the immunotherapy nanoparticle composition is a PD-1-targeting fusion protein. In one embodiment, the fusion protein is AMP-224 (PD-L2 IgG2a fusion protein; Amplimmune/GlaxoSmith Klein); AMP-514 (MEDI0680) (PD-L2 fusion protein; Amplimmune/GlaxoSmith Klein), or a biosimilar thereof.

In some aspects, the nanoparticle composition and the PD-1 immunotherapy are administered sequentially. In some aspects, the nanoparticle composition is administered prior to administration of the PD-1 immunotherapy. In some aspects, the PD-1 immunotherapy is administered prior to administration of the nanoparticle composition. In some aspects, the nanoparticle composition and the PD-1 immunotherapy are administered concurrently.

In some embodiments, the present invention relates to a method for increasing the therapeutic effectiveness of an immunotherapy treatment of a patient suffering from a cancer which expresses PD-L1 or PD-L2. The method comprises administering to the patient a therapeutically effective amount of the nanoparticle composition as described herein, and a PD-1 immunotherapy comprising a second binding agent, wherein when the binding agents of the nanoparticle composition are capable of binding to PD-L1 and/or PD-L2, the second binding agent of the immunotherapy is capable of binding to PD-1, and wherein when the binding agents of the nanoparticle composition are capable of binding to PD-1, the second binding agent of the immunotherapy is capable of binding to PD-L1 and/or PD-L2.

In some embodiments, the present invention relates to a method for treating a patient suffering from a cancer which expresses PD-L1 or PD-L2. The method comprises administering to the patient a therapeutically effective amount of the nanoparticle composition as described herein, and an immunotherapy comprising a second binding agent, wherein the binding agents of the nanoparticle composition are capable of binding to PD-L1, PD-L2, or PD-1, and the second binding agent of the immunotherapy is capable of binding to PD-L1, PD-L2, or PD-1, respectively.

In one embodiment, a method for treating a patient suffering from a cancer which expresses PD-L1 or PD-L2 comprises administering to the patient a nanoparticle composition comprising nanoparticles and a PD-1 immunotherapy. Each of the nanoparticles of the nanoparticle composition comprises: (a) a carrier protein, (b) binding agents having a PD-L1 or PD-L2 binding portion and (c) optionally at least one therapeutic agent. Upon reconstitution with an aqueous solution, the binding agents of the nanoparticles are capable of binding to PD-L1 or PD-L2.

In one embodiment, a method for increasing the therapeutic effectiveness of an immunotherapy treatment of a patient suffering from a cancer which expresses PD-L1 or PD-L2 comprises administering to the patient (a) a therapeutically effective amount of the nanoparticle composition described herein and (b) a PD-1 immunotherapy. In some embodiments, the nanoparticle composition is lyophilized, and upon reconstitution with an aqueous solution, the binding agents of the nanoparticles are capable of binding to PD-L1 or PD-L2.

In some aspects, the amount of the nanoparticles and the amount of the second binding agents are determined in a relative ratio with each other.

In some aspects, a ratio of synergistically effective amounts of the nanoparticle composition and the second binding agent of the immunotherapy increases the therapeutic effectiveness of the immunotherapy such that the effectiveness of the immunotherapy is substantially greater than an administration thereof alone. In one aspect, the ratio of the amount of the nanoparticle composition to the second binding agent can range from about 1:1, 1:1.5, 1:2, 1:2.5, 1:3, 1:4, 1:5, 1:6, 1:7, 1:8, 1:9 or 1:10 to about 1:4, 1:5, 1:6, 1:7, 1:8, 1:9, 1:10, 1:11, 1:12, 1:15 or about 1:20.

In another aspect, the method for increasing the therapeutic efficacy of an immunotherapy reduces the therapeutically effective dose of the second binding agent required or preferred in the immunotherapy by administering the nanoparticles as described herein above to the patient. The ratio of the amount of the nanoparticle composition and the amount of the second binding agent is in a range of from about 1:1 to about 1:10 and/or wherein the synergistic therapeutic effectiveness of administration of such combination can achieve a synergistic therapeutic effectiveness that is at least about 5%, or about 10%, or about 15%, or about 20%, or about 25%, or about 30%, or about 35%, or about 40%, or about 45%, or about 50%, or about 55%, or about 60%, or about or about 65%, or about 70%, or about 80%, or about 90% or about 100% greater than the therapeutic effectiveness of mono-administration of the second binding agent. In another aspect, the synergistic therapeutic effectiveness of administration of such combination is at least about 25%, or about 30%, or about 35%, or about 40%, or about 45%, or about 50%, greater than the therapeutic effectiveness of mono-administrations of either the nanoparticle composition or the second binding agent.

In one embodiment, the second binding agent of the immunotherapy comprises about 60 mg/mL for intravenous delivery over a period of from about 30 minutes to about 60 minutes (e.g., atezolizumab).

In one embodiment, the second binding agent of the immunotherapy comprises about 1.0 mg/kg to about 3.0 mg/kg for intravenous delivery for a period of about 60 minutes (e.g., nivolumab).

In one embodiment, the second binding agent of the immunotherapy comprises about, 2 mg/kg for intravenous delivery for a period of about 30 minutes (e.g., pembrolizumab).

In some embodiments, the present invention relates to a method for increasing the therapeutic effectiveness of an immunotherapy treatment of a patient suffering from a cancer which expresses PD-L1 or PD-L2. The method comprises administering to the patient a therapeutically effective amount of the nanoparticle composition as described herein above, and an immunotherapy comprising a second binding agent, wherein when the binding agents of the nanoparticles are capable of binding to PD-L1 and/or PD-L2, the second binding agent of the immunotherapy is capable of binding to PD-1, and wherein when the binding agents of the nanoparticles are capable of binding to PD-1, the second binding agent of the immunotherapy is capable of binding to PD-L1 and/or PD-L2.

In some embodiments, the present invention relates to a method for treating a patient suffering from a cancer which expresses PD-L1 or PD-L2. The method comprises administering to the patient a therapeutically effective amount of the nanoparticle composition as described herein above, and an immunotherapy comprising a second binding agent, wherein the binding agents of the nanoparticles are capable of binding to PD-L1, PD-L2, PD-1, wherein the second binding agent of the immunotherapy is capable of binding to the same one of PD-L1, PD-L2, PD-1 as the binding agents of the nanoparticles In some aspects, the amount of the nanoparticles is of an effective amount of the nanoparticle composition. In some aspect, the amount of the nanoparticles is of an amount less than the effective amount of the nanoparticle composition when administered to the patient alone.

In some aspects, the second binding agents are of an effective amount. In some aspects, the second binding agents are of an amount less than the effective amount when administered to the patient alone.

In one embodiment, the therapeutically effective amount of the nanoparticles described herein comprises about 1 mg/m² to about 200 mg/m² antibody, about 2 mg/m² to about 150 mg/m², about 5 mg/m² to about 100 mg/m², about 10 mg/m² to about 85 mg/m², about 15 mg/m² to about 75 mg/m², about 20 mg/m² to about 65 mg/m², about 25 mg/m² to about 55 mg/m², about 30 mg/m² to about 45 mg/m², or about 35 mg/m² to about 40 mg/m² antibody. In other embodiments, $^{the}$ therapeutically effective amount comprises about 20 mg/m² to about 90 mg/m² antibody. In one embodiment, the therapeutically effective amount comprises 30 mg/m² to about 70 mg/m² antibody. In one embodiment, the therapeutically effective amount of the nanoparticles described herein comprises about 50 mg/m² to about 200 mg/m² carrier protein or carrier protein and therapeutic agent. In a preferred embodiment, the therapeutically effective amount comprises about 75 mg/m² to about 175 mg/m² carrier protein or carrier protein and therapeutic agent. Contemplated values include any value, subrange, or range within any of the recited ranges, including endpoints.

In one embodiment, the therapeutically effective amount of the nanoparticle composition comprises about 20 mg/m² to about 90 mg/m² binding agent, e.g., antibody, aptamer or Fc fusion. In a preferred embodiment, the therapeutically effective amount comprises 30 mg/m² to about 70 mg/m² binding agent, e.g., antibody, aptamer or Fc fusion. Contemplated values include any value, subrange, or range within any of the recited ranges, including endpoints.

Cancers or tumors that can be treated by the compositions and methods described herein include, but are not limited to: biliary tract cancer; brain cancer, including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors include breast cancer, lymphoma, multiple myeloma, and melanoma.

In general, the compounds of this invention will be administered in a therapeutically effective amount by any of the accepted modes of administration for agents that serve similar utilities. The actual amount of the compound of this invention, i.e., the nanoparticles, will depend upon numerous factors such as the severity of the disease to be treated, the age and relative health of the subject, the potency of the compound used, the route and form of administration, and other factors well known to the skilled artisan.

An effective amount of such agents can readily be determined by routine experimentation, as can the most effective and convenient route of administration, and the most appropriate formulation. Various formulations and drug delivery systems are available in the art. See, e.g., Gennaro, A. R., ed. (1995) *Remington's Pharmaceutical Sciences,* 18th ed., Mack Publishing Co.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

Examples

The present disclosure is illustrated using nanoparticles composed of albumin-bound paclitaxel (i.e., ABRAXANE®) or cisplatin as core, and antibodies that recognize PD-L1 (e.g., atezolizumab). One skilled in the art would understand that making and using the nanoparticles of the Examples are for the sole purpose of illustration, and that the present disclosure is not limited by this illustration.

Any abbreviation used herein, has normal scientific meaning. All temperatures are ° C. unless otherwise stated. Herein, the following terms have the following meanings unless otherwise defined:

| | |
|---|---|
| ABX | = ABRAXANE ® (albumin-bound paclitaxel) |
| ADC | = antibody dependent chemotherapy |
| BEV | = bevacizumab |
| BSA | = bovine serum albumin |
| dH$_2$O | = distilled water |
| nM | = nanomolar |
| EdU | = 5-ethynyl-2'-deoxyuridine |
| FITC | = Fluorescein isothiocyanate |
| kD | = kilo-dalton |
| Kd | = dissociation constant |
| kg | = kilogram |
| M | = molar |
| mg | = milligram |
| ml or mL | = milliliter |
| m$^2$ | = square meters |
| mm$^3$ | = cubic millimeter |
| μg | = microgram |
| μl | = microliter |
| μm | = micrometer/micron |
| PBS | = Phosphate buffered saline |
| pK | = pharmacokinetics |
| RT | = room temperate |
| rpm | = rotations per minute |

Example 1: Antigen Binding of Lyophilized AR160

CD20 positive Daudi lymphoma cells were labeled with fluorescent tagged anti-human CD20 or isotype matched control in panel F and A, respectively, and analyzed by flow cytometry. In the other panels, the Daudi cells were pre-treated with ABX, AR160, AR160L (AR160 lyophilized and resuspended into a solution suitable for injection), or Rituxan prior to CD20 labeling. FIG. 1 demonstrates that CD20 binding was specifically blocked by the AR particles and Rituxan, but not ABX alone. These results suggest that the AR binds to its CD20 ligand on these cells blocking binding of the fluorescent anti-CD20.

FIG. 2 is a histogram overlay of the data presented in FIG. 1.

Figure 3A:
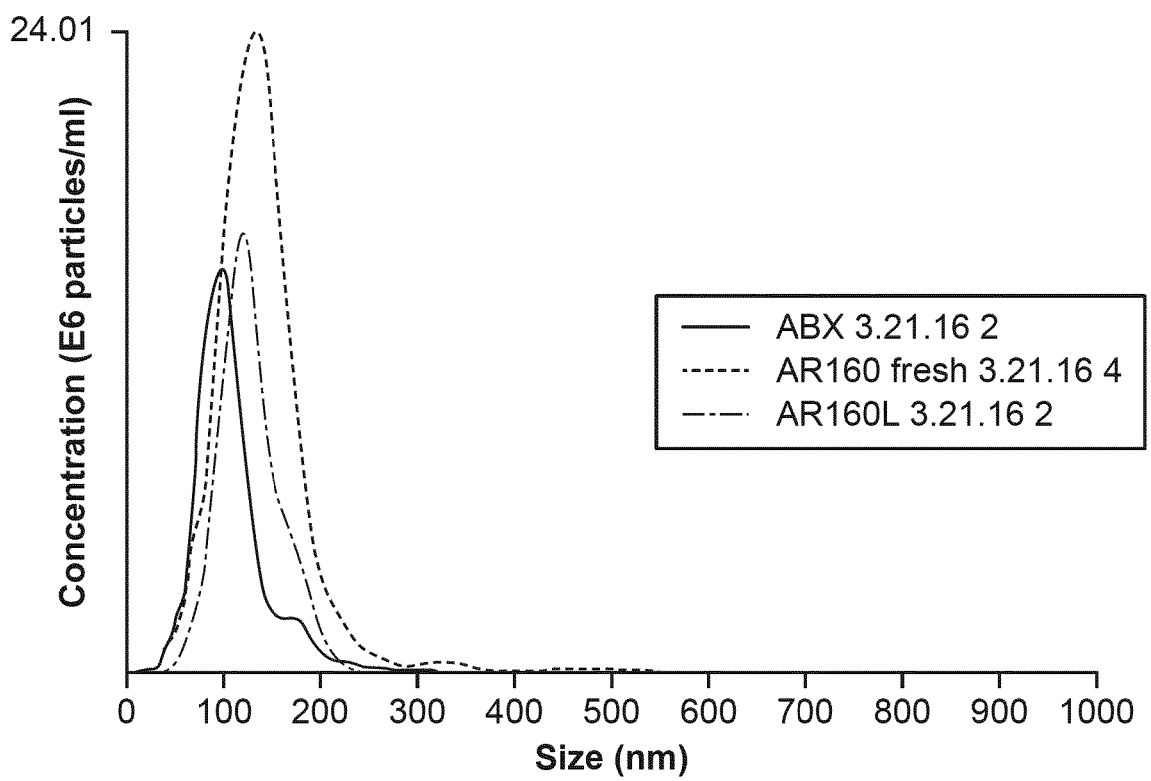
FIGS. 3A-B depict particle size comparisons of ABX alone relative to ABX/rituximab nanoparticles (AR.
Figure 3B:
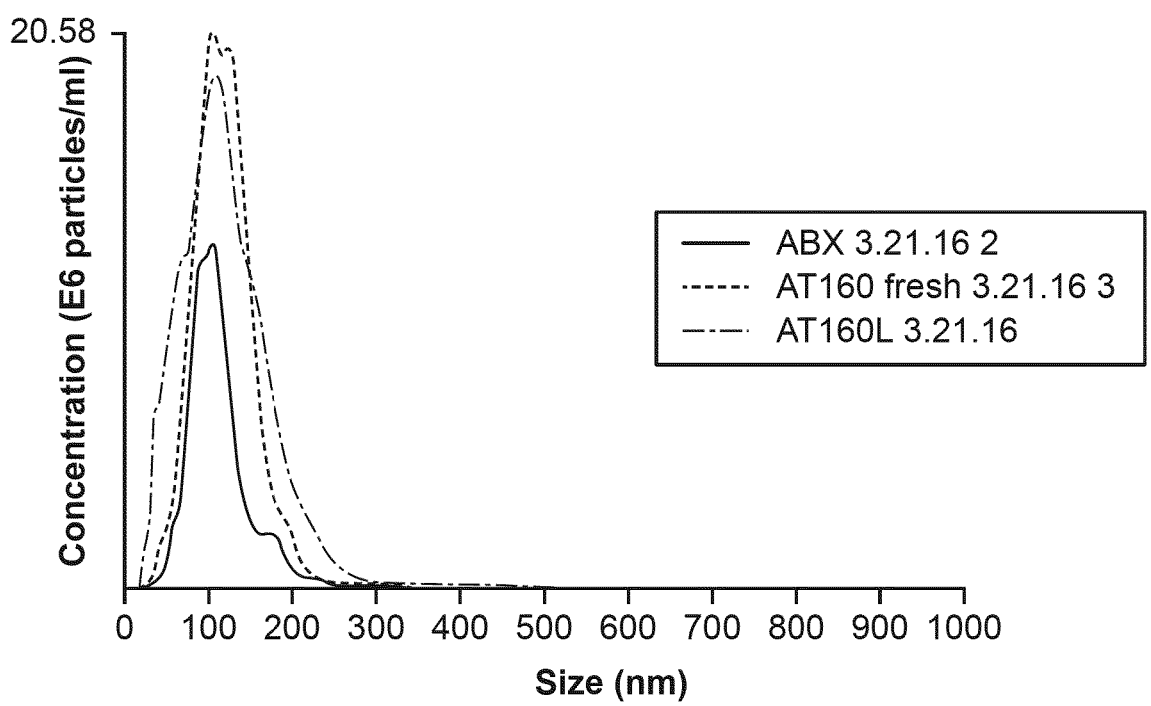

FIGS. 3A and 3B depict the particle size comparisons of ABX alone relative to AR (FIG. 3A) and AT (FIG. 3B) freshly made and lyophilized.

Figure 4:
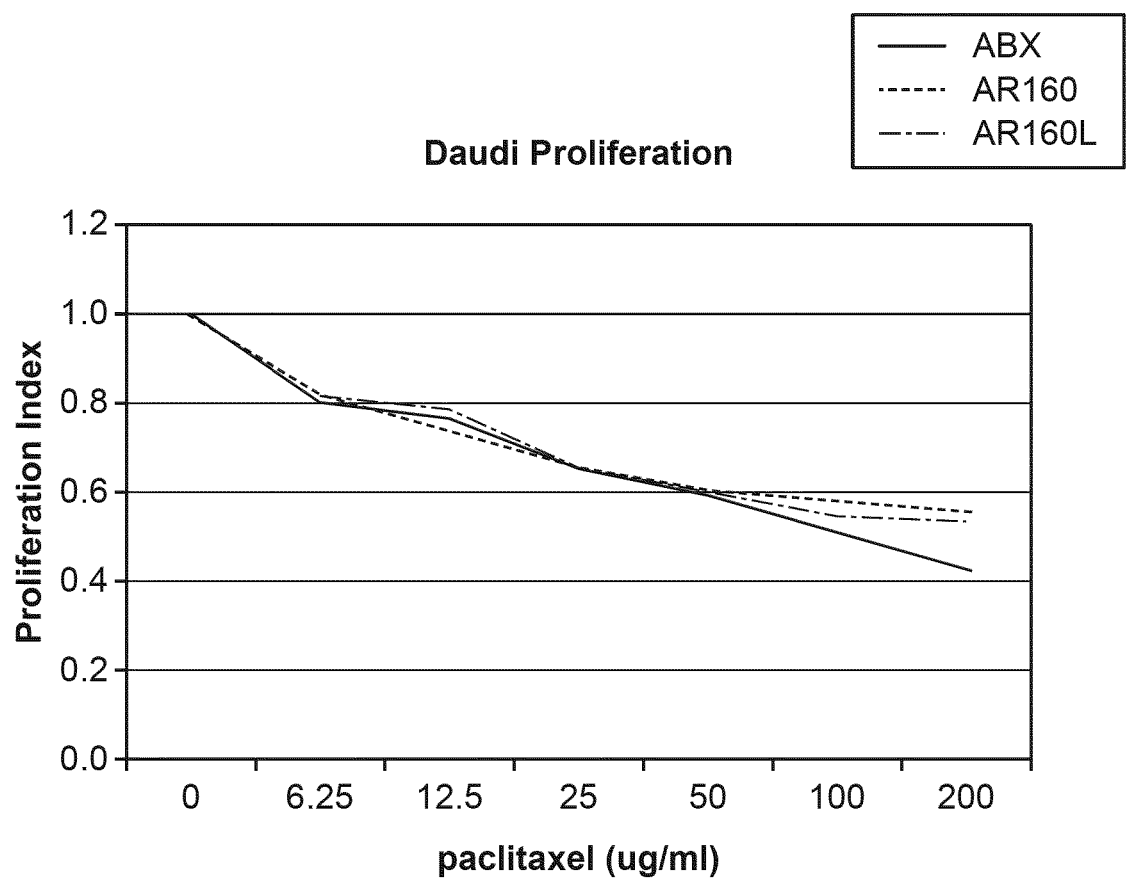
FIG. 4 compares the toxicity of ABX and AR particles in a Daudi cell proliferation assay.

FIG. 4 presents the results of a Daudi proliferation assay comparing the toxicity of ABX and the AR particles. The data demonstrates the lyophilized and non-lyophilized nanoparticles have essentially the same toxicity in the Daudi assay.

Figure 5A:
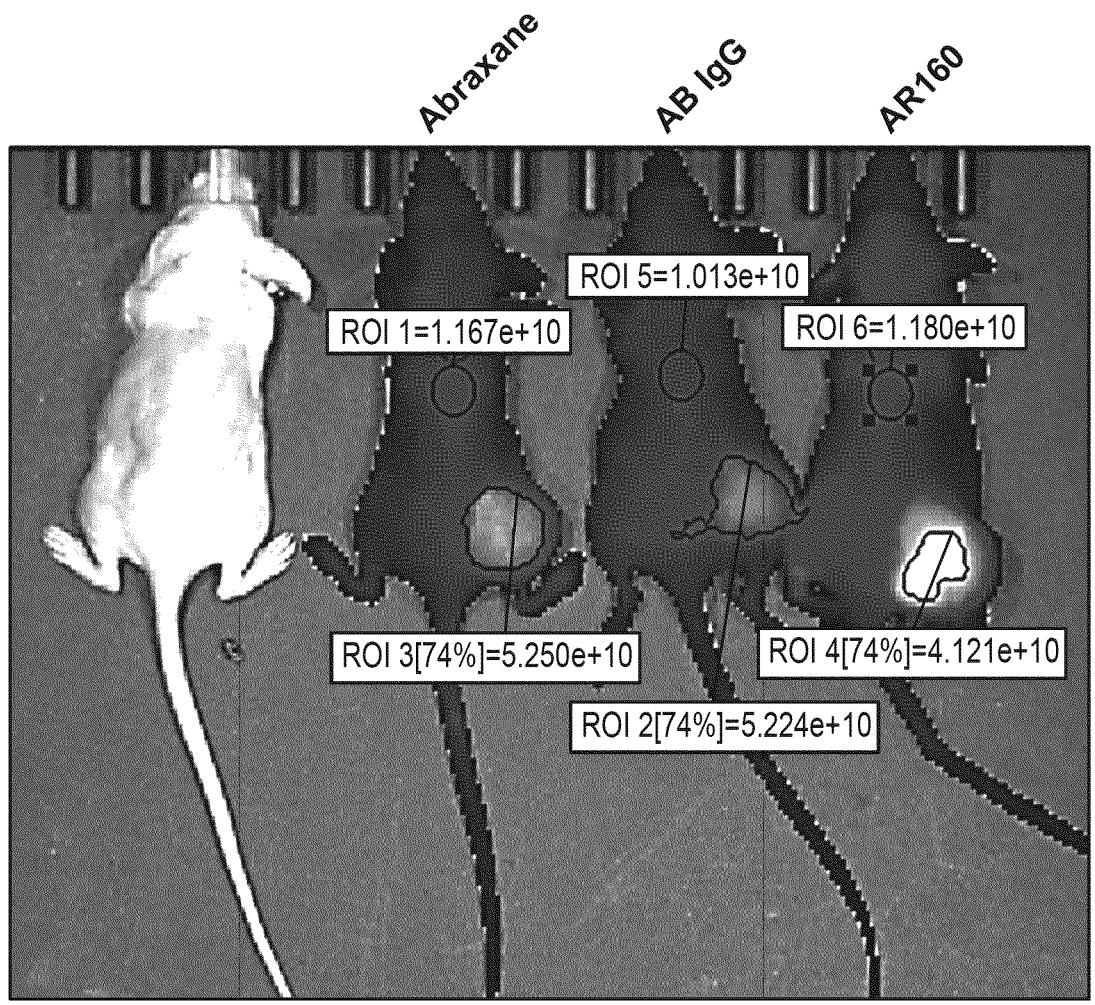
FIGS. 5A-5C depict the results obtained in mice treated with either labeled ABRAXANE®, labeled ABRAXANE® coated with non-specific (bevacizumab) antibodies (AB IgG), or labeled ABRAXANE® coated with Rituximab (AR160).
Figure 5B:
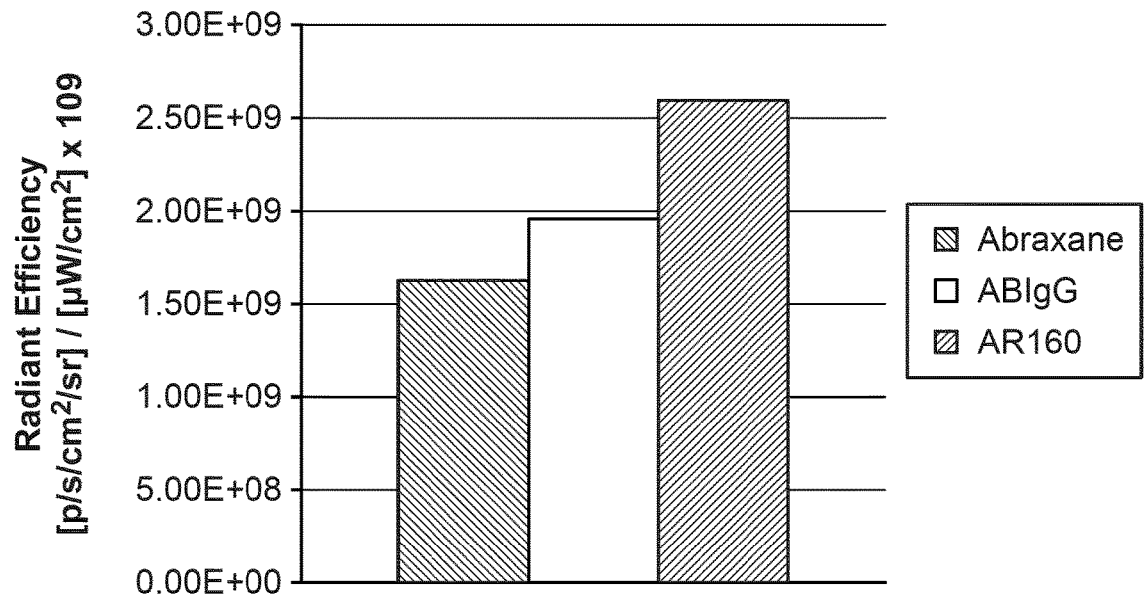
Figure 5C:
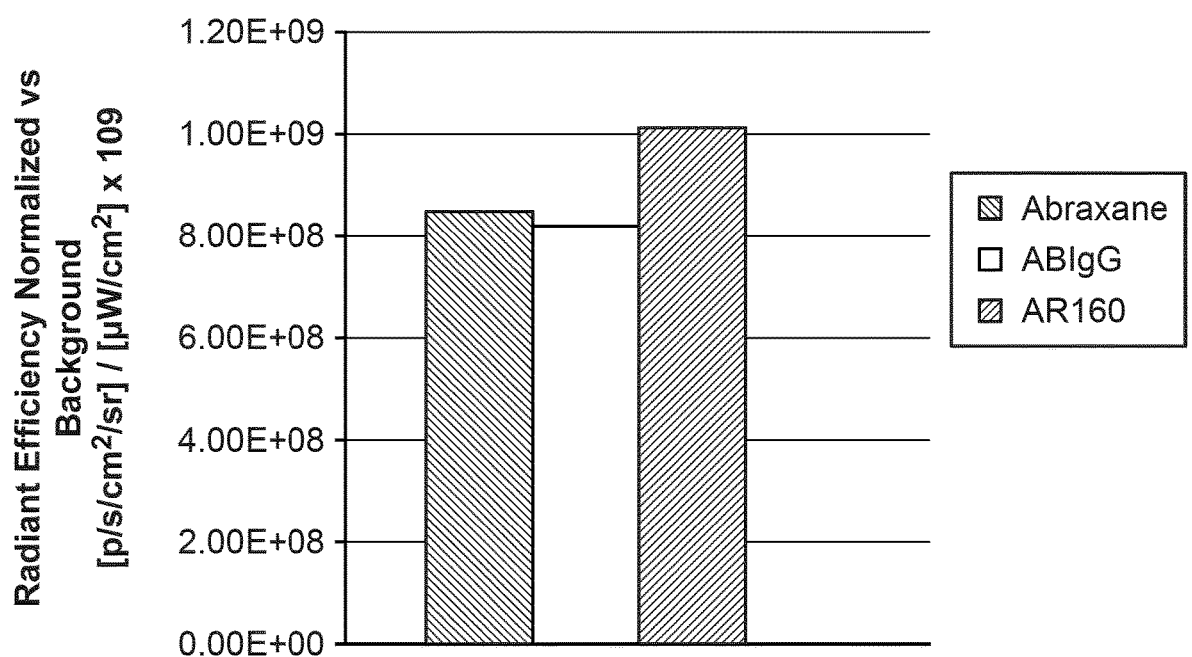

Example 2: Fluorescent Analysis of Tumor Accumulation of AlexaFluor 750 Labeled Nanoparticles Mice received intravenous (IV) injections of equal amounts of either labeled ABRAXANE®, labeled ABRAXANE® coated with non-specific antibodies (AB IgG), or labeled ABRAXANE® coated with Rituximab (AR160). Regions of interest (ROI) 2, 3, and 4 (FIG. 5A) track tumor accumulation based on a fluorescence threshold; ROI 1, 5, and 6 (FIG. 5A) serve as background references. Fluorescence was determined in the ROIs 24 hours post injection. FIG. 5B is a bar graph of the average fluorescence per unit of tumor area of mice in all three treatment groups were determined to provide the gross tumor delivery. FIG. 5C is a bar graph of the average fluorescence per unit of tumor area normalized by background ROI to give proportion of drug delivered to tumor versus body. The data demonstrate that administration of AR160 nanoparticles results in an increased fluorescence as compared to ABRAXANE® alone or ABRAXANE® coated with non-specific antibodies.

Figure 6:
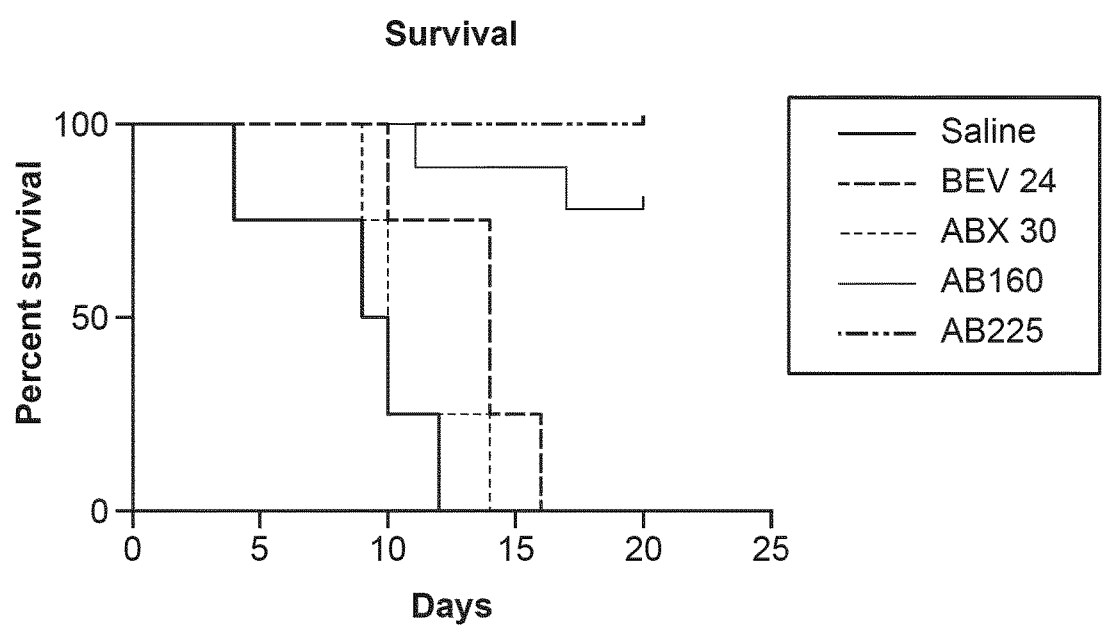
FIG. 6 depicts the survival of the mice treated with a single dose of saline, BEV24 (bevacizumab at 24 mg/kg), ABX30 (ABX at 30 mg/kg), AB160 (12 mg/kg BEV and 30 mg/kg ABX) and AB225 (24 mg/kg BEV and 30 mg/kg ABX). At 30 days post-administration, the survival of mice treated with AB225 and with AB160 far exceeds the survival of mice treated with BEV alone or ABRAXANE® alone.

Example 3: In Vivo Efficacy of ABX-Rituximab Nanoparticles Having a Size of 225 nm To make a nanoparticle having a size of 225 nm, the particles were prepared as described in PCT Pub. No. WO2017/031368 (incorporated herein by reference in its entirety), but the ratio of BEV to ABRAXANE® was 4:5, i.e., 4 parts BEV and 5 parts ABRAXANE. This ratio produced nanoparticles having a size of 225 nm (AB225). The effect of AB225 was assayed in animals as described in PCT Pub. No. WO2017/031368. FIG. 6 depicts the survival of the mice treated with a single dose of saline, BEV, ABX, AB160 and AB225 and with AB160 with a BEV pretreatment. At 30 days post-administration the survival of mice treated with AB225, and with AB160 with or without pretreatment with BEV far exceeds the survival of mice treated with BEV alone of ABRAXANE® alone.

Example 4: Making Atezolizumab-ABRAXANE® Nanoparticles

Atezolizumab and ABRAXANE® (ABX) were co-incubated at room temperature for 30 minutes at a concentration of 4 mg/mL and 10 mg/mL, respectively to form the nanoparticle, AA130.

Figure 7:
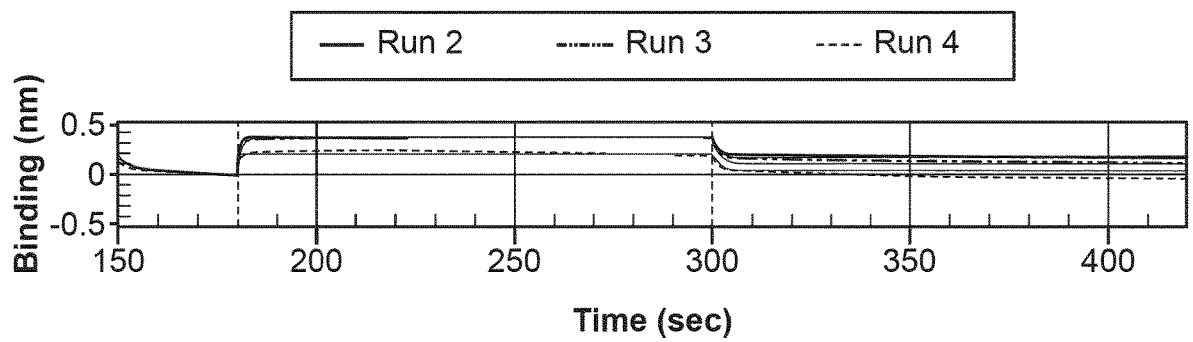
FIG. 7 shows the binding affinity between atezolizumab and ABX. The Kd was determined to be $1.462 \times 10^{-9}$. Biolayer interferometry (BLItz) (Forte Bioscience) was performed using streptavidin probes.

To determine whether atezolizumab and ABX are capable of interacting to form nanoparticle complexes, Biolayer interferometry (BLItz) (Forte Bioscience) was performed using streptavidin probes. 100 ug/ml of biotinylated atezolizumab in 1×PBS was bound to the streptavidin probe. After washing unbound atezolizumab from the probe, the antibody-bound probe was exposed to ABX at concentrations of 100, 500, 1000 μg/mL in 1×PBS. An antibody probe exposed to PBS was used as background and background was subtracted. BLItz software was used to calculate dissociation constants (FIG. 7). The Kd was determined to be $1.462 \times 10^{-9}$.

Example 5: Size Determination of Atezolizumab-ABRAXANE® Nanoparticles

Mastersizer NS300 was employed to determine the particle size of atezolizumab bound ABX relative to ABX alone. Nanosight uses dynamic light scattering and Brownian motion to calculate particle size.

Figure 8A:
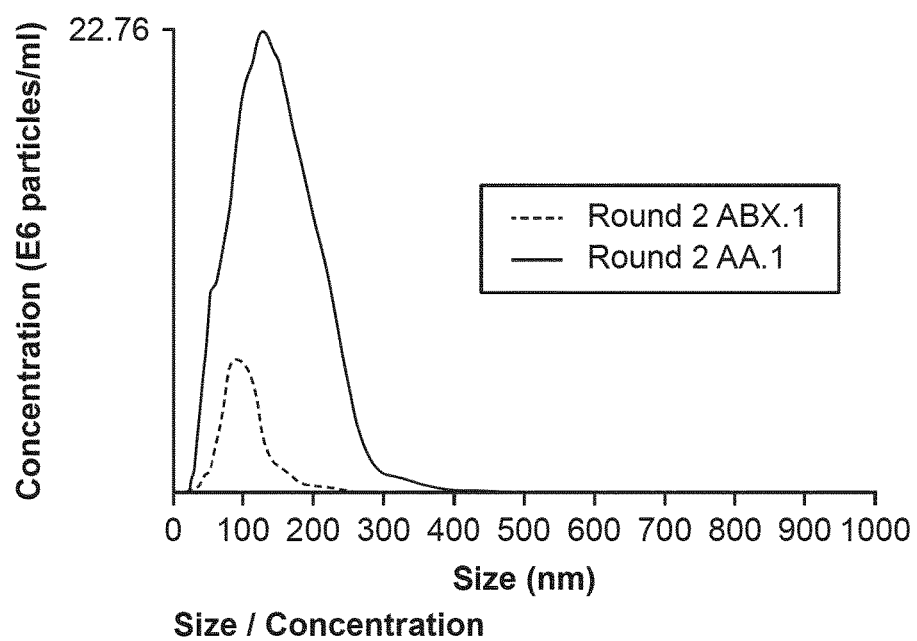
FIG. 8A shows the particle size distribution for ABX alone (average size of 90 nm) and ABX-atezolizumab nanoparticles (AA; average size of 129 nm), as determined by Mastersizer NS300.
Figure 8B:
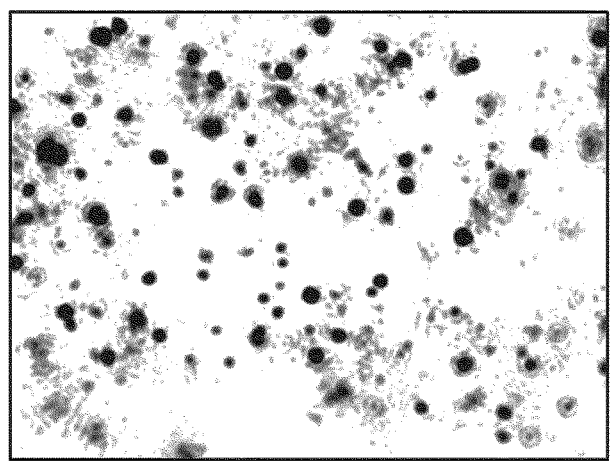
FIG. 8B is a photograph of the ABX-atezolizumab nanoparticles from FIG. 8A.

Atezolizumab and ABX were co-incubated to form the nanoparticle, AA130, as described above. ABX was diluted 1:200 and atezolizumab-bound ABX was diluted 1:800; three 30-second video clips were captured and analyzed to determine particle size (FIG. 8A). FIG. 8B is a still image from one of the video clips of AA130. The average particle size of the atezolizumab-ABX nanoparticles was determined to be about 129 nm; average size of ABX alone is about 90 nm.

Example 6: AA130 Binds PD-L1

Flow cytometry was performed to access binding of atezolizumab and atezolizumab bound Abraxane to the ligand, PD-L1. The PD-L1 positive melanoma cell line, C8161 was used for this experiment. AA130 was made as described above and an aliquot of the nanoparticles was spun at 6000 rpm for 10 minutes to remove any unbound atezolizumab. C8161 cells were stained with FITC labeled isotype control and anti-human PD-L1 as negative and positive controls, respectively. The C8161 cells were incubated for 30 minutes with ABX and atezolizumab alone and the AA130 nanoparticle. After the incubation the cells were labeled with FITC labeled anti-human PD-L1 for 30 minutes and washed with FACS buffer (1×PBS+0.5% BSA and 0.05% Na azide). After washing, the cells were analyzed by flow cytometer on the Guava 8HT and data analysis performed with Gauvasoft software (Millipore).

Figure 9A:
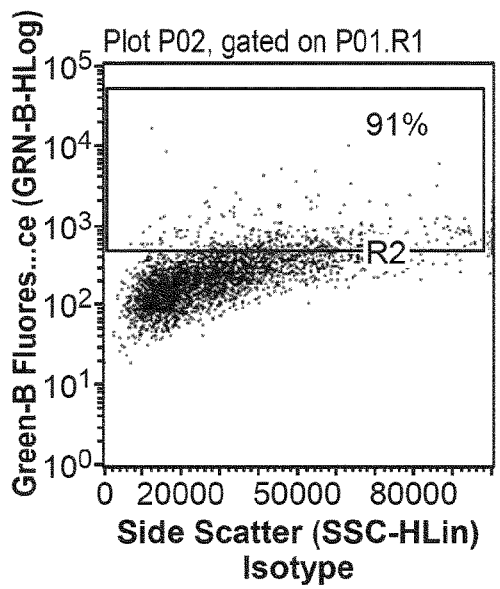
FIGS. 9A-9E show flow cytometry of ABX-atezolizumab nanoparticles (AA130) competing with labeled anti-PD-L1 antibody for binding to a PD-L1 positive human melanoma cell line, C8161. C8161 cells were pre-treated with isotype control antibody (FIG. 9A), no treatment (FIG. 9B), ABRAXANE® (FIG. 9C), atezolizumab (FIG. 9D), or AA130 (FIG. 9E), then labeled with fluorescently-labeled anti-PD-L1 antibody.
Figure 9B:
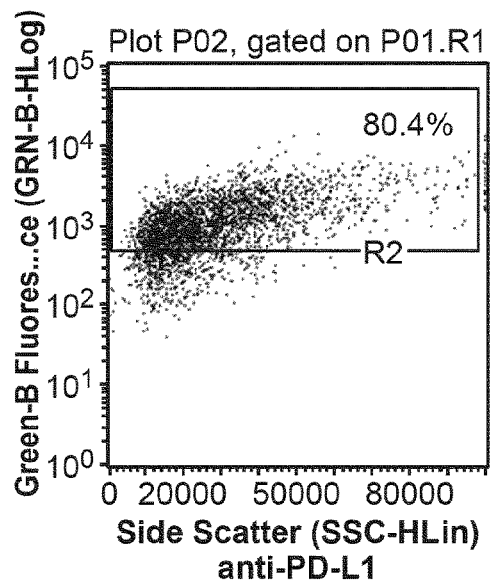
Figure 9C:
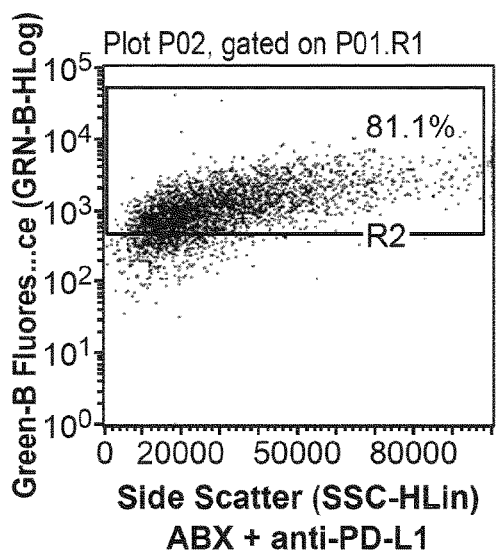
Figure 9D:
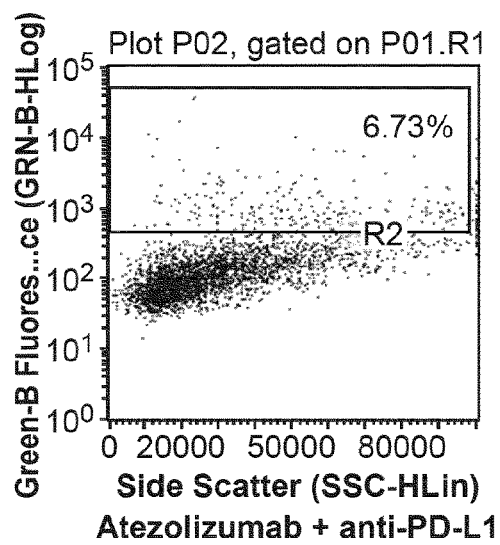
Figure 9E:
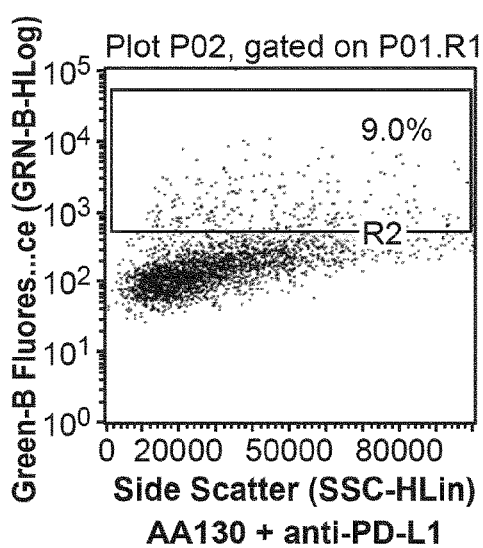

C8161 cells were pre-treated with isotype control antibody (FIG. 9A), no treatment (FIG. 9B), ABRAXANE® (FIG. 9C), atezolizumab (FIG. 9D), or AA130 (FIG. 9E), then labeled with fluorescently-labeled anti-PD-L1 antibody. The atezolizumab in the context of the 130 nm particle retains its ability to bind its ligand, PD-L1.

Example 7: AA130 Cellular Toxicity

C8161 melanoma cells were exposed to ABX and AA130 at paclitaxel concentrations from 0 to 200 μg/mL overnight to determine cell toxicity. The cells were also incubated with EdU, a thymidine analog. The next day the cells were harvested, fixed with 2% paraformaldehyde and permeabolized with 1% saponin. After permeabolization the cells were incubated for 30 minutes with a FITC labeled anti-EdU antibody to determine the percentage of cells proliferating. After washing, the cells were analyzed by flow cytometer on the Guava 8HT and data analysis performed with Gauvasoft software (Millipore). The proliferation index was calculated by normalization to an untreated positive control.

Figure 10:
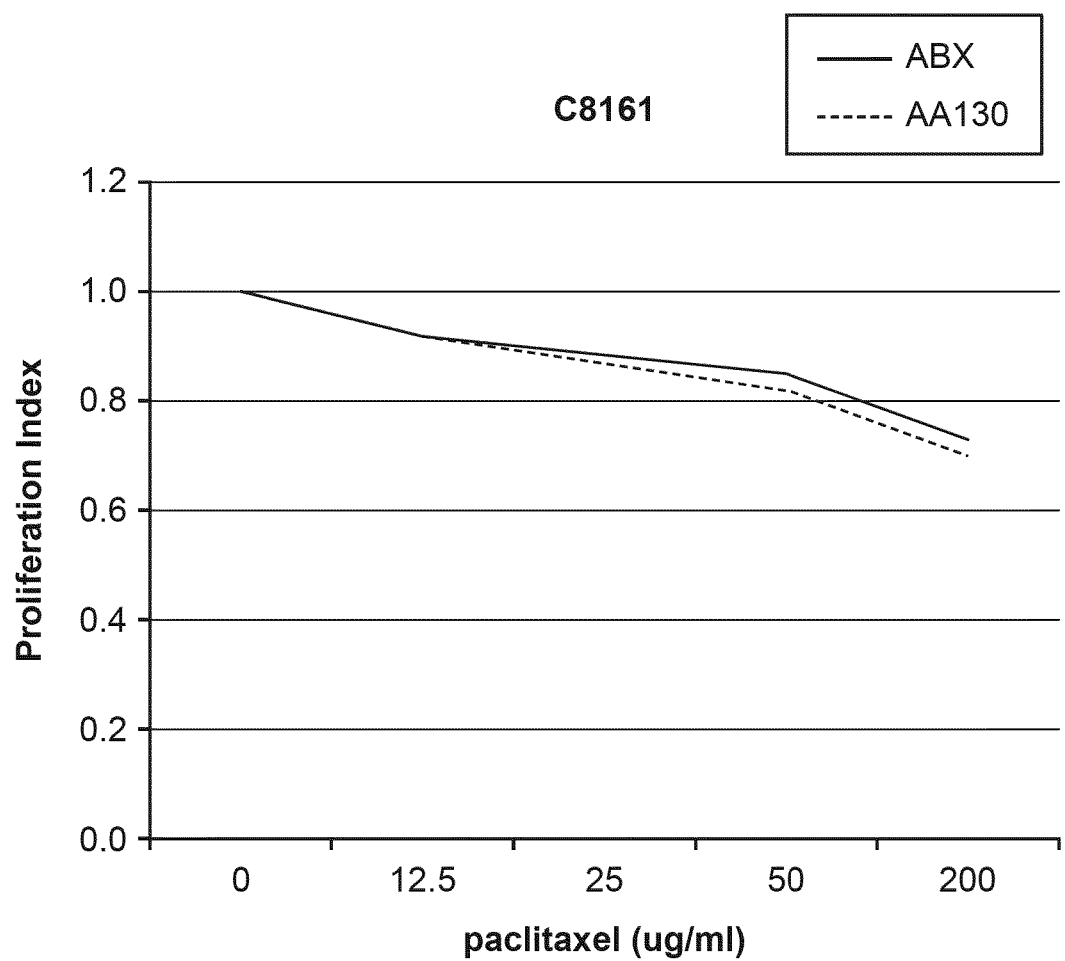
FIG. 10 shows the dose-dependent toxicity of ABX (solid line) and AA130 (broken line) on C8161 cells.
Figure 11A:
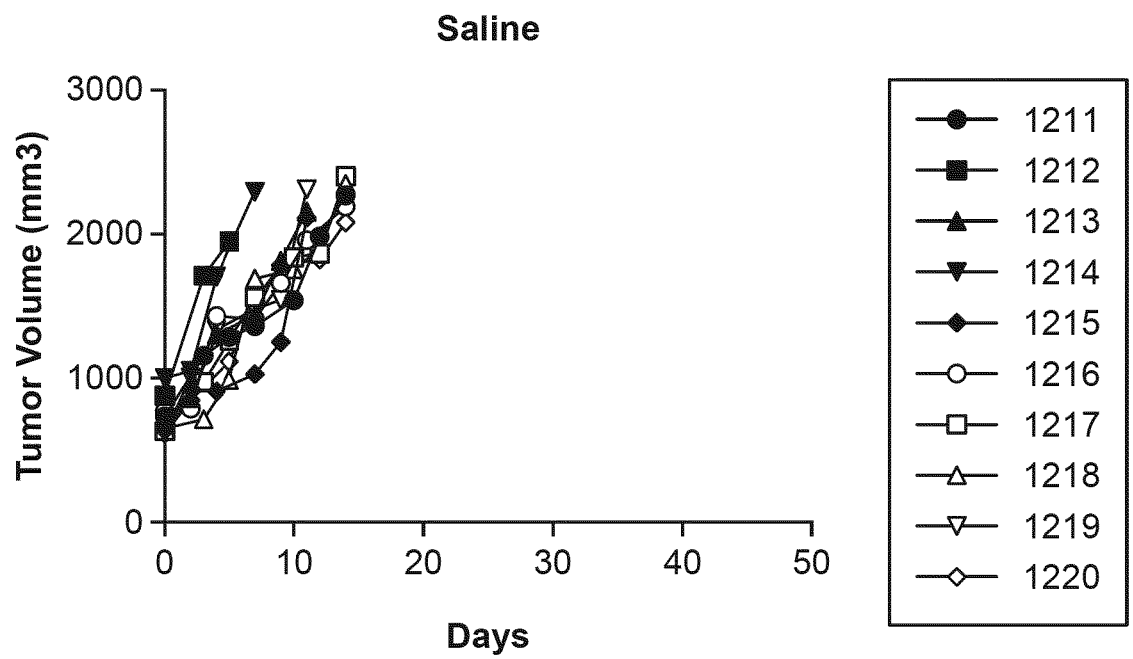
FIGS. 11A-11D show the change in tumor volume over time in mice that were injected with $2 \times 10^6$ PD-L1 positive C8161 melanoma tumor cells, then treated by 100 ul IV tail vein injection with saline (FIG. 11A), atezolizumab alone (18 mg/kg.
Figure 11B:
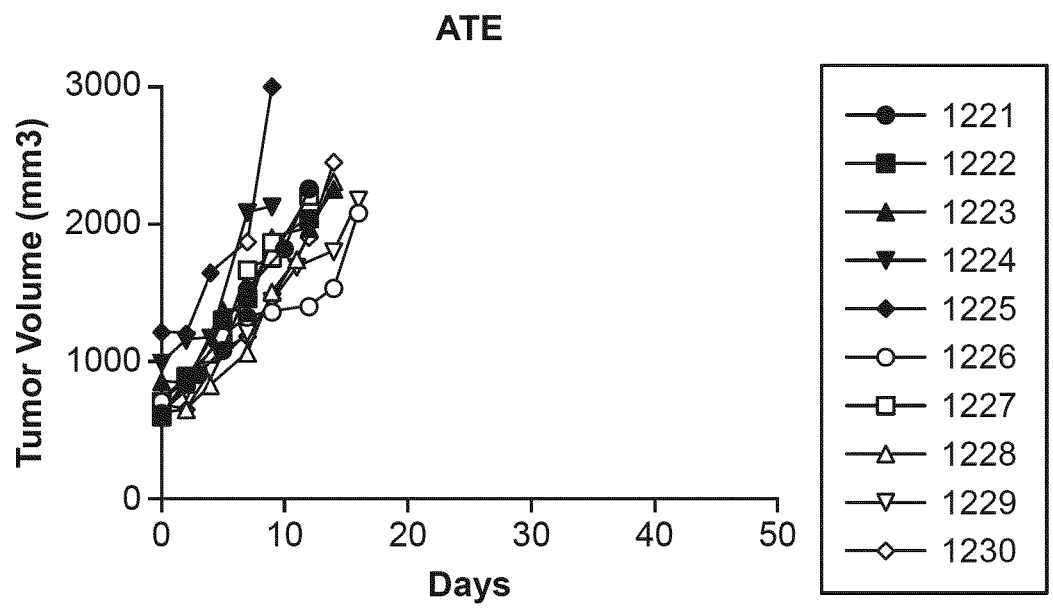
Figure 11C:
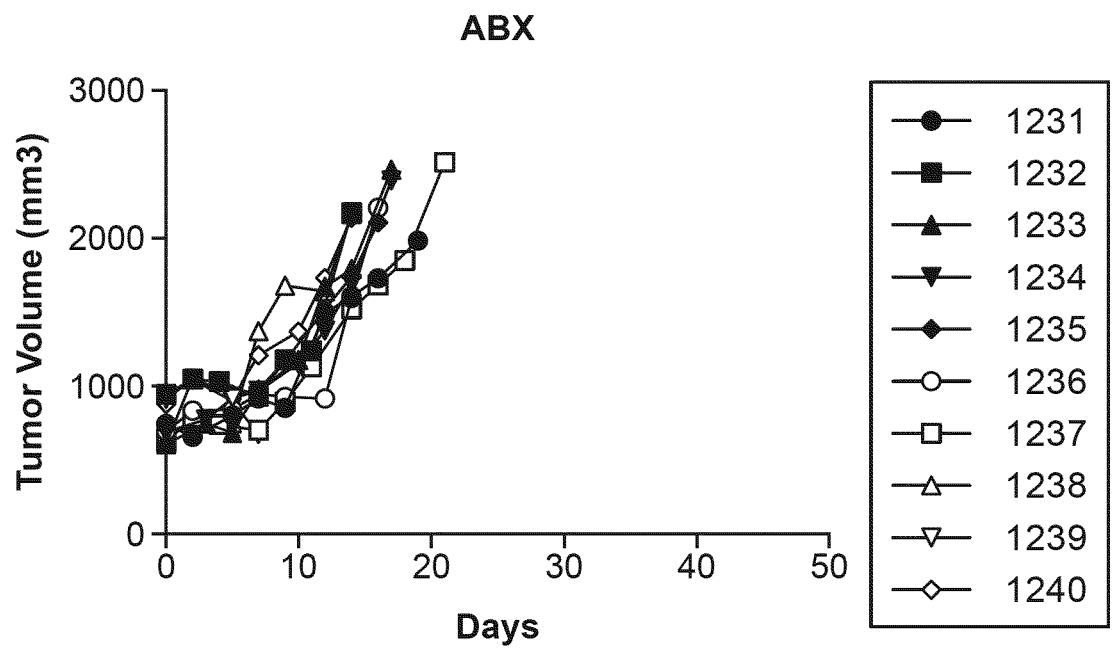
Figure 11D:
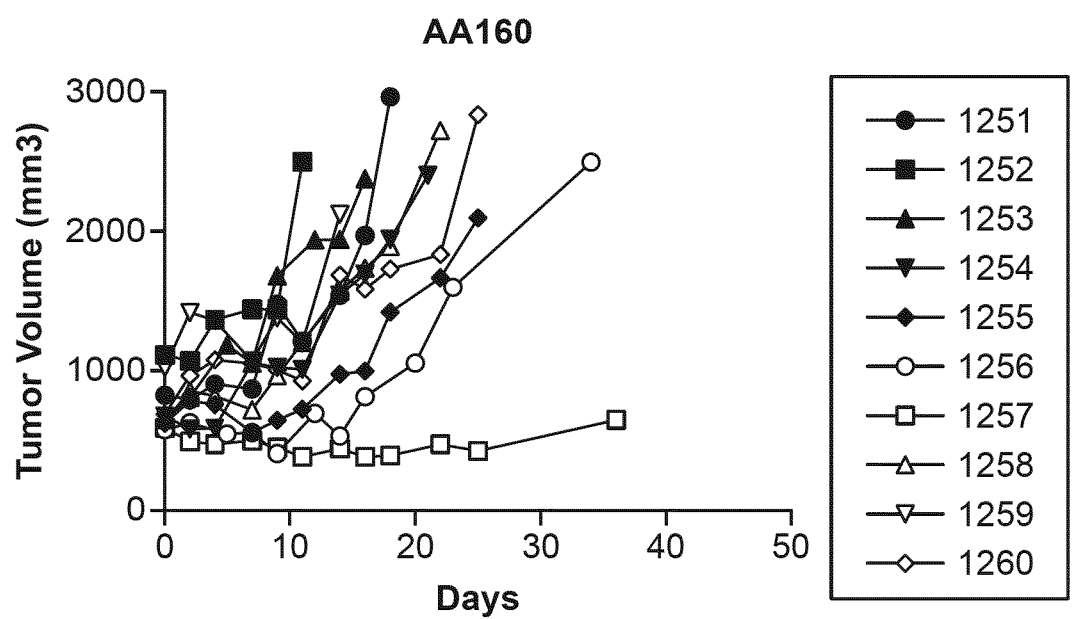

FIG. 10 shows the dose-dependent toxicity of ABX (solid line) and AA130 (broken line) on C8161 cells. The AA130 has cellular toxicity similar to ABX alone.

Example 8: In Vivo Efficacy of AA130 Nanoparticles

Athymic nude mice (Harlan Sprague Dawley) were injected with $2 \times 10^6$ PD-L1 positive C8161 melanoma tumor cells. The tumors were allowed to grow until about 600 mm³ and were treated by 100 μl IV tail vein injection with saline, atezolizumab alone (18 mg/kg), ABX alone (45 mg/kg) and AA130 (18 mg/kg atezolizumab and 45 mg/kg ABX) one time (FIGS. 11A-11D). Tumor growth was monitored 3 times/week. Tumor size was calculated with the equation: (length×width²)/2.

Figure 12:
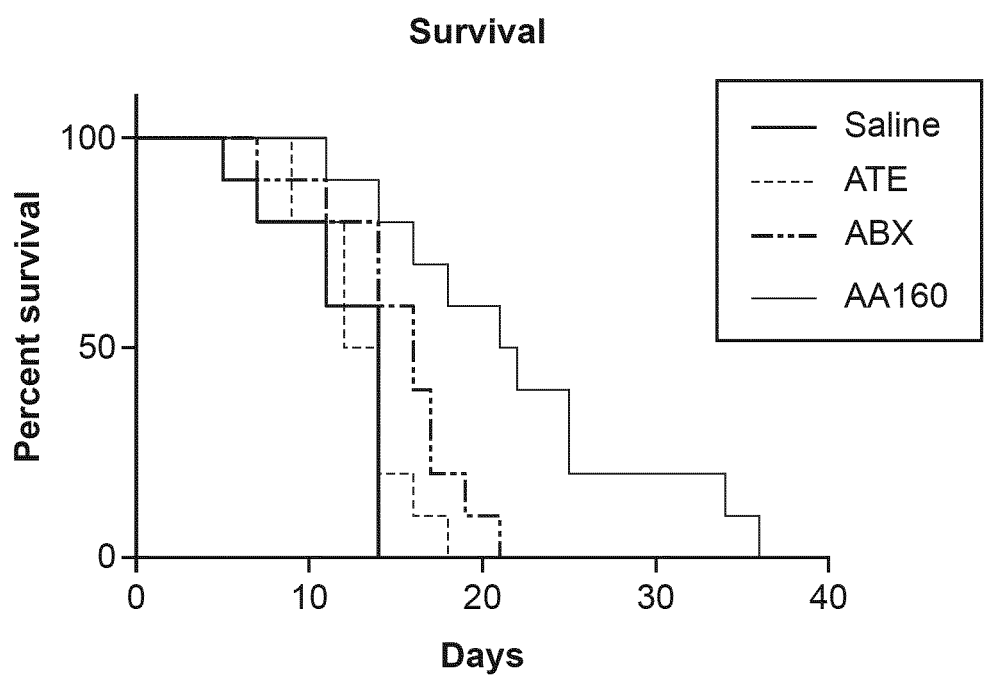
FIG. 12 depicts the survival of the mice from the experiment shown in FIGS. 11A-11D. Kaplan Meier curves were generated using Graph Pad software. The median survival for each group was 14, 13, 16, and 21.5 days for saline, atezolizumab, Abraxane and AA130, respectively. Survival differences between AA130 and all other groups were significant, with p-values of 0.0008 for saline, 0.0015 for atezolizumab, and 0.0113 for ABX.

Tumor growth curves (FIG. 12) show slowed tumor growth in the mice treated with AA130 relative to saline and the individual drugs alone. Kaplan Meier curves were generated using Graph Pad software. The median survival for each group was 14, 13, 16, and 21.5 days for saline, atezolizumab, ABX and AA130, respectively. Survival differences between AA130 and all other groups were significant with p-values of 0.0008 for saline, 0.0015 for atezolizumab, and 0.0113 for Abraxane.

What is claimed is:

1. A nanoparticle comprising:
   a. albumin,
   b. between about 100 to about 1000 antibodies non-covalently bound to a surface of the nanoparticle, wherein the antibodies are capable of binding to PD-L1, and
   c. paclitaxel,
   such that said nanoparticle is capable of binding to PD-L1.

2. The nanoparticle of claim 1, wherein the antibodies are selected from atezolizumab, avelumab, durvalumab, BMS 936559 (MDX1105), or biosimilars thereof.

3. A nanoparticle composition comprising the nanoparticle of claim 1.

4. The nanoparticle composition of claim 3 which is lyophilized, wherein upon reconstitution with an aqueous solution the nanoparticle is capable of binding to PD-L1.

5. The nanoparticle of claim 1, further comprising an additional therapeutic agent selected from abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idambicin, imatinib, hydroxyurea, imatinib, lapatinib, leuprorelin, melphalan, methotrexate, mitoxantrone, nedaplatin, nilotinib, oxaliplatin, pazopanib, pemetrexed, picoplatin, romidepsin, satraplatin, sorafenib, vemurafenib, sunitinib, teniposide, triplatin, vinblastine, vinorelbine, vincristine, or cyclophosphamide.

6. A kit comprising the nanoparticle composition of claim 3 and a PD-1 immunotherapy agent.

7. A method for treating a patient suffering from a cancer which expresses PD-L1, said method comprising administering to the patient:
   (a) a composition comprising the nanoparticle of claim 1; and
   (b) a PD-1 immunotherapy.

8. The method of claim 7, wherein the PD-1 immunotherapy comprises a second antibody capable of binding to PD-1.

9. The method of claim 8, wherein the second antibody is integrated onto and/or into the nanoparticle, and optionally a second therapeutic agent.

10. The method of claim 8, wherein the second antibody is nivolumab, pembrolizumab, pidilizumab, PDR001, or biosimilar thereof.

11. The method of claim 7, wherein the antibodies of the nanoparticle comprise atezolizumab, avelumab, durvalumab, BMS 936559 (MDX1105), or biosimilars thereof.

12. The method of claim 7, wherein the nanoparticle composition is lyophilized, the method further comprising reconstituting the nanoparticle composition in an aqueous solution prior to administration.

13. The method of claim 1, further comprising administering to the patient an additional therapeutic agent selected from abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, pazopanib, pemetrexed, picoplatin, romidepsin, satraplatin, sorafenib, vemurafenib, sunitinib, teniposide, triplatin, vinblastine, vinorelbine, vincristine, or cyclophosphamide.

14. A method for increasing the therapeutic effectiveness of an immunotherapy treatment of a patient suffering from a cancer which expresses PD-L1, comprising administering to the patient
   (a) a therapeutically effective amount of a composition comprising the nanoparticle of claim 1, and
   (b) a PD-1 immunotherapy.

* * * * *